US012767962B2

(12) United States Patent
Pavel-Dinu et al.

(10) Patent No.: US 12,767,962 B2
(45) Date of Patent: Oct. 20, 2026

(54) GENE CORRECTION FOR SCID-X1 IN LONG-TERM HEMATOPOIETIC STEM CELLS

(71) Applicant: The Board of Trustees of the Leland Stanford Junior University, Stanford, CA (US)

(72) Inventors: Mara Pavel-Dinu, Stanford, CA (US); Matthew H. Porteus, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 803 days.

(21) Appl. No.: 18/007,439

(22) PCT Filed: Aug. 3, 2021

(86) PCT No.: PCT/US2021/044401
§ 371 (c)(1),
(2) Date: Jan. 30, 2023

(87) PCT Pub. No.: WO2022/031746
PCT Pub. Date: Feb. 10, 2022

(65) Prior Publication Data

US 2024/0093242 A1 Mar. 21, 2024

Related U.S. Application Data

(60) Provisional application No. 63/060,586, filed on Aug. 3, 2020.

(51) Int. Cl.
*A61K 35/28* (2015.01)
*C12N 5/0789* (2010.01)
(Continued)

(52) U.S. Cl.
CPC ............ *C12N 15/907* (2013.01); *A61K 35/28* (2013.01); *C12N 5/0647* (2013.01); *C12N 9/22* (2013.01);
(Continued)

(58) Field of Classification Search
CPC .............................. C12N 15/907; A61K 35/28
See application file for complete search history.

(56) References Cited

U.S. PATENT DOCUMENTS

| | | | | |
|---|---|---|---|---|
| 11,193,141 | B2 * | 12/2021 | Dever | A61K 35/28 |
| 2019/0032091 | A1 * | 1/2019 | Dever | A61K 35/28 |
| 2020/0009266 | A1 * | 1/2020 | Chan | A61K 45/06 |

FOREIGN PATENT DOCUMENTS

| | | | |
|---|---|---|---|
| WO | 2016/164356 | A1 | 10/2016 |
| WO | 2017/214460 | A1 | 12/2017 |

(Continued)

OTHER PUBLICATIONS

International Patent Application No. PCT/US2021/044401, International Preliminary Report on Patentability, Feb. 16, 2023, 7 pages.

(Continued)

*Primary Examiner* — James D Schultz
*Assistant Examiner* — Keenan A Bates
(74) *Attorney, Agent, or Firm* — Kilpatrick Townsend & Stockton LLP

(57) ABSTRACT

The present disclosure provides methods and compositions for treating SCID-X1 in subjects, comprising genetically modifying cells from the subjects ex vivo by integrating a full-length, codon-optimized IL2RG cDNA at the endogenous IL2RG locus.

14 Claims, 23 Drawing Sheets

Specification includes a Sequence Listing.

(51) Int. Cl.

| | |
|---|---|
| ***C12N 9/22*** | (2006.01) |
| ***C12N 15/113*** | (2010.01) |
| ***C12N 15/90*** | (2006.01) |

(52) U.S. Cl.

CPC ...... *C12N 15/1138* (2013.01); *C12N 2310/20* (2017.05); *C12N 2310/315* (2013.01); *C12N 2310/344* (2013.01); *C12N 2510/00* (2013.01); *C12N 2800/80* (2013.01)

(56) References Cited

FOREIGN PATENT DOCUMENTS

| | | | |
|---|---|---|---|
| WO | 2018/152371 | A1 | 8/2018 |
| WO | 2020/123871 | A1 | 6/2020 |
| WO | 2022/031746 | A1 | 2/2022 |

OTHER PUBLICATIONS

International Patent Application No. PCT/US2021/044401, International Search Report and Written Opinion, Nov. 18, 2021, 11 pages.

Pereira, M. et al., "2018 CIS Annual Meeting: Immune Deficiency & Dysregulation North American Conference," Journal of Clinical Immunology, 38:330-444, Apr. 23, 2018.

* cited by examiner

FIG. 1A
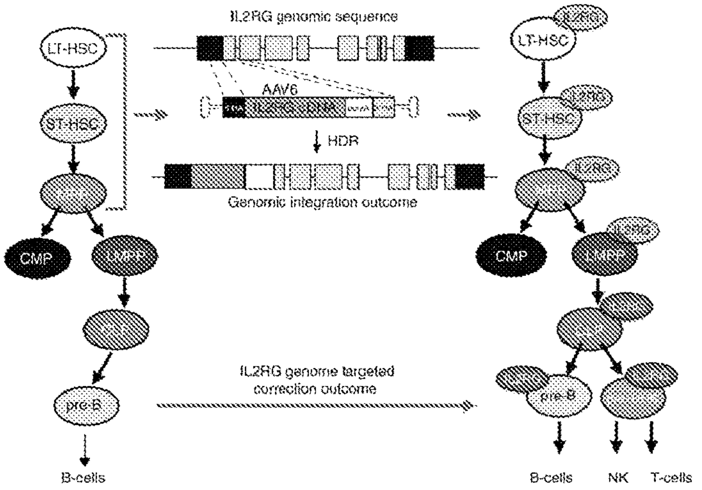
FIG. 1B
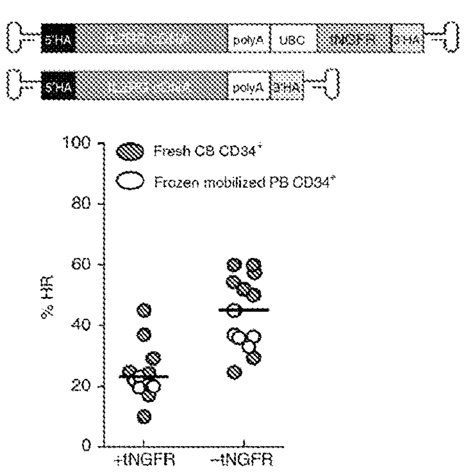
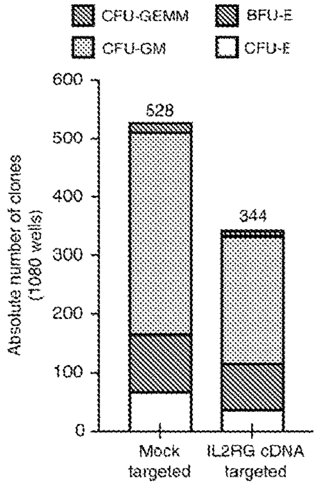
FIG. 1C
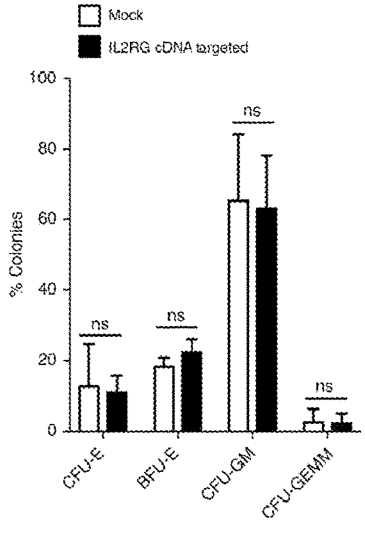
FIG. 1D
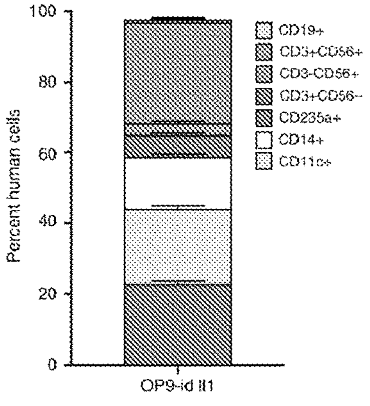
FIG. 1E FIG. 2A
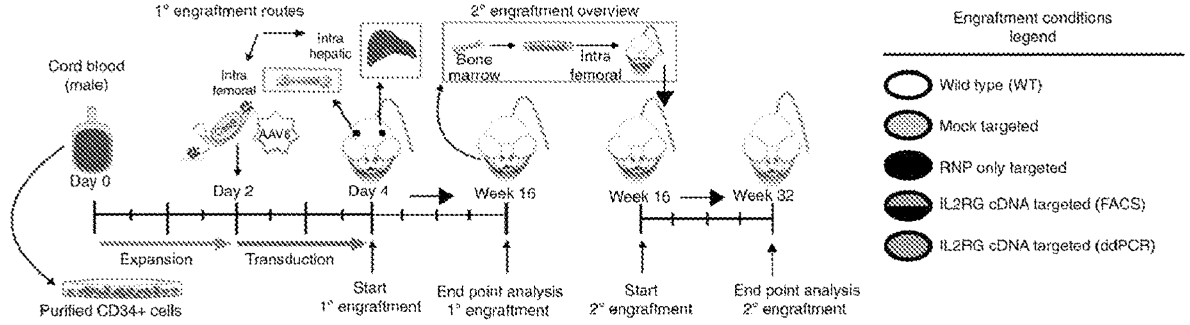
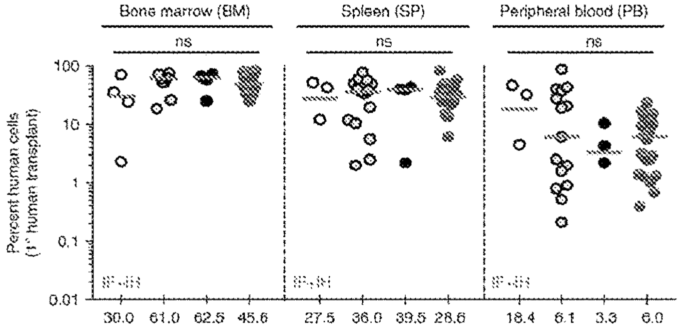
FIG. 2B
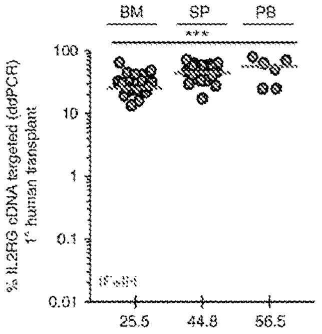
FIG. 2C
FIG. 2D
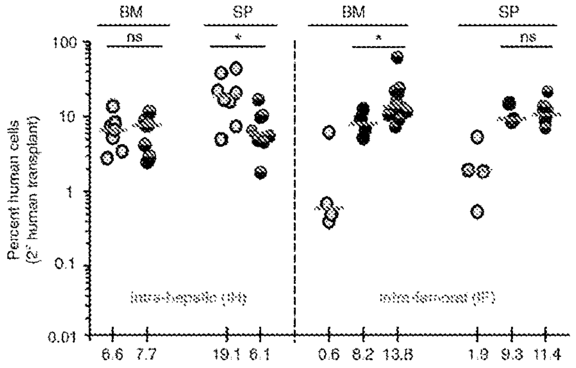
FIG. 2E
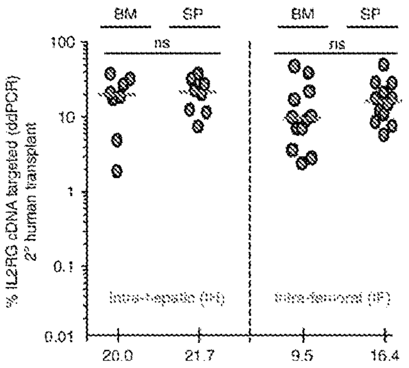

FIG. 4A
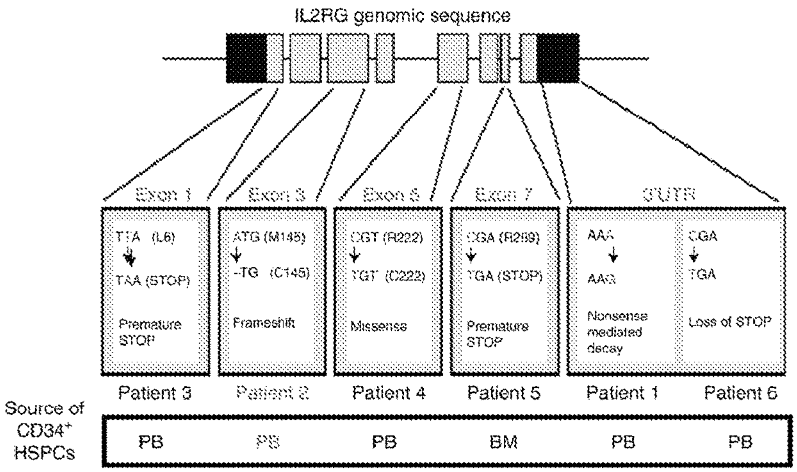
FIG. 4B
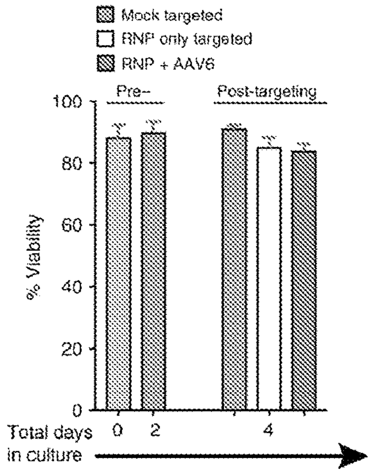
FIG. 4C
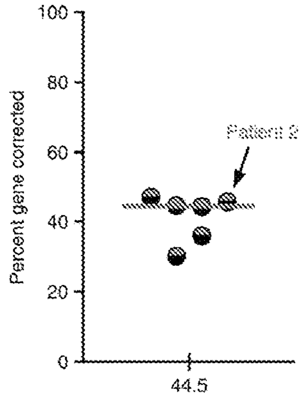
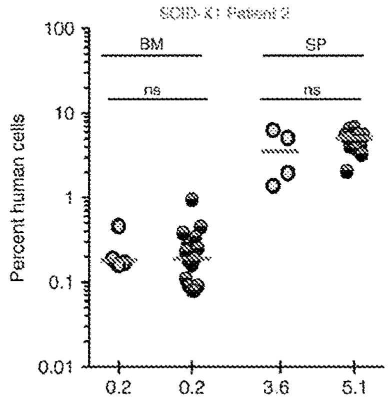
FIG. 4D
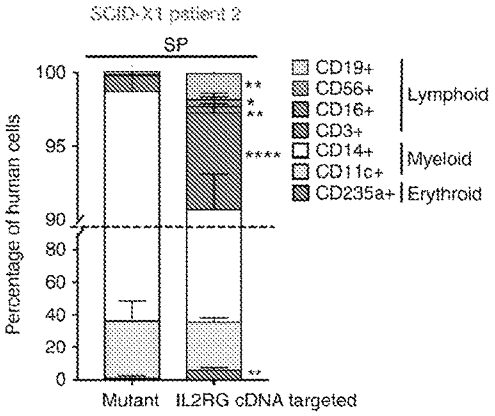
FIG. 4E
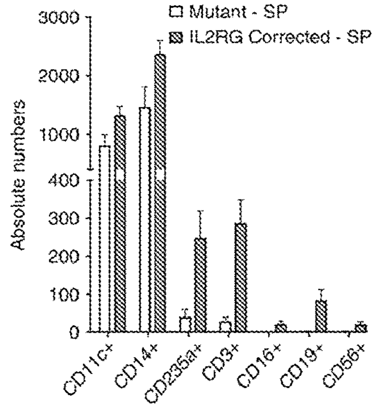
FIG. 4F FIG. 5A
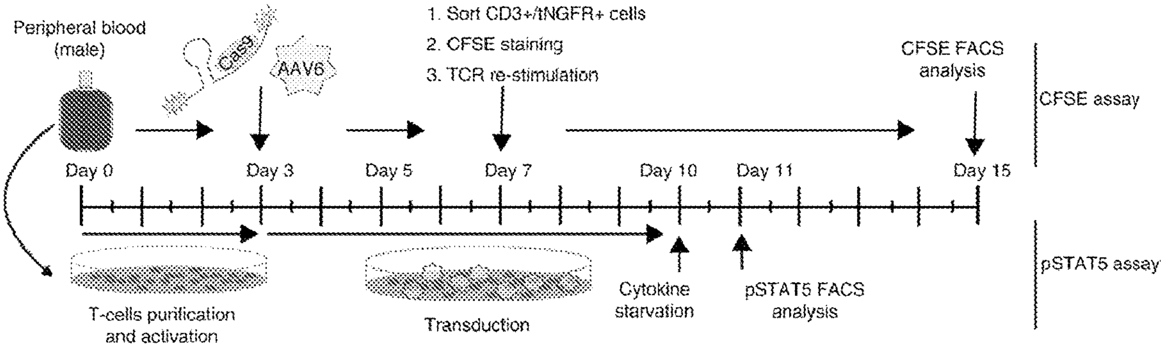
FIG. 5B
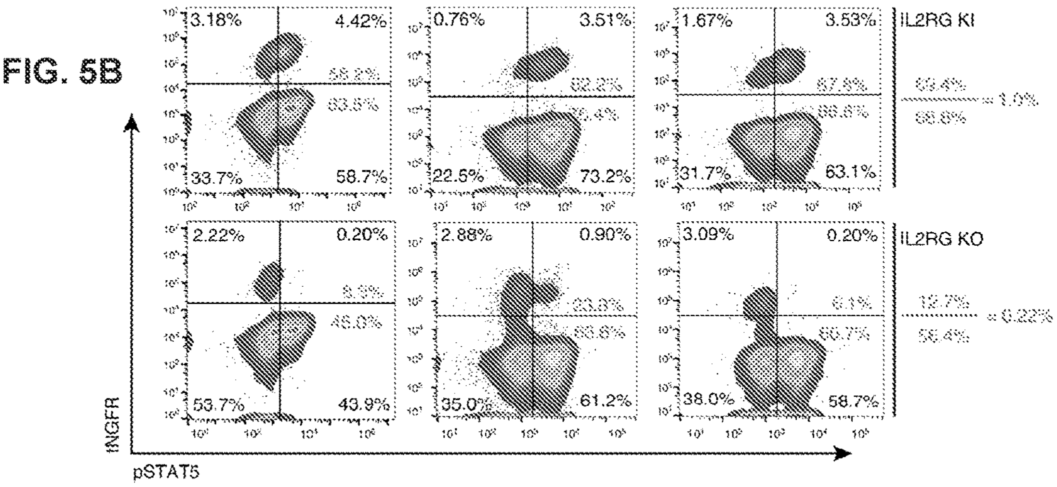
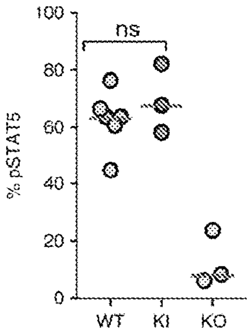
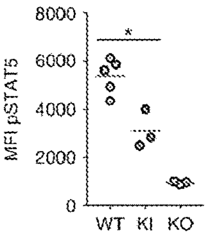
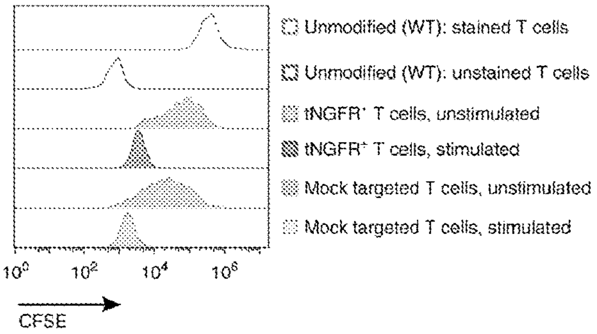
FIG. 5C FIG. 5D FIG. 5E FIG. 6A
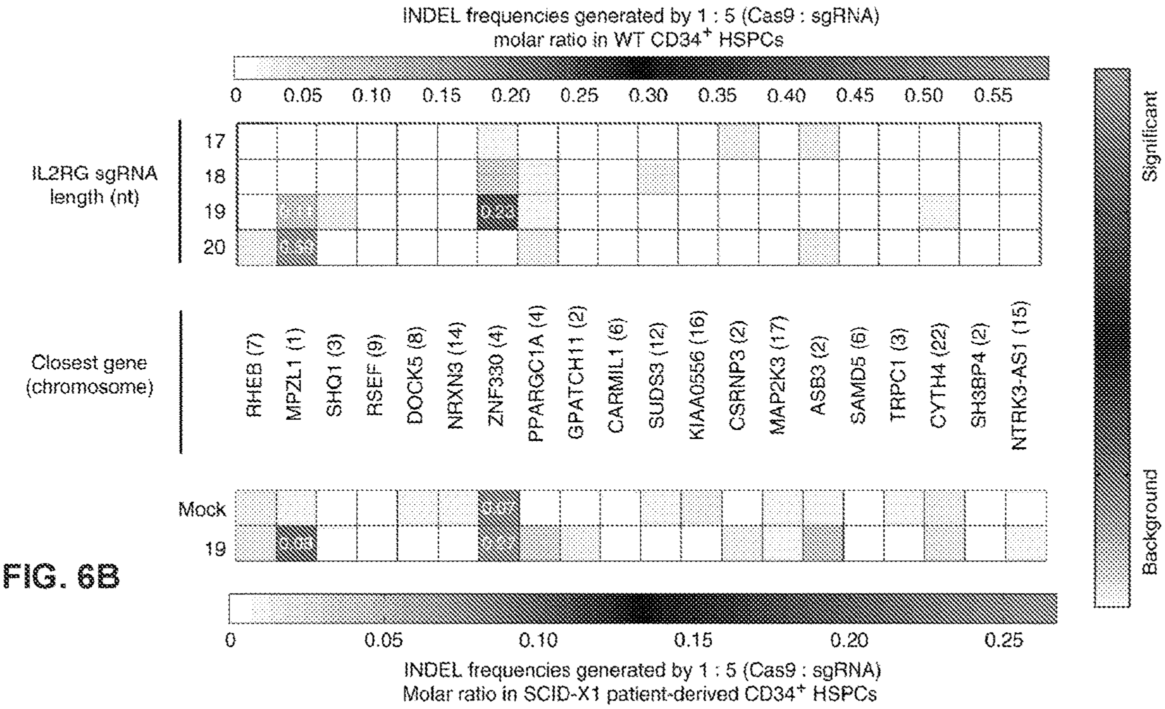
FIG. 6B
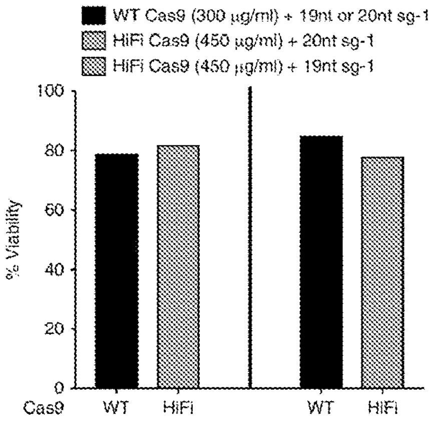
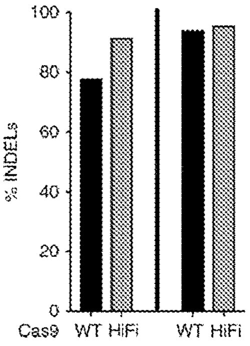
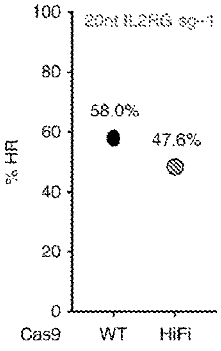
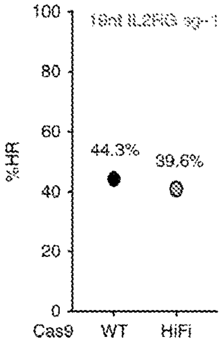
FIG. 6C FIG. 6D FIG. 6E FIG. 6F

| Nucleofection Programs | EO100 | | EO102 | | EO104 | | DZ100 | | AAV6 Donor Only | |
|---|---|---|---|---|---|---|---|---|---|---|
| Days Post Nucleofection | Total Live Cells | Total GFP+ Cells | Total Live Cells | Total GFP+ Cells | Total Live Cells | Total GFP+ Cells | Total Live Cells | Total GFP+ Cells | Total Live Cells | Total GFP+ Cells |
| Day 4 | 101,001 | 765 | 116,300 | 839 | 74,231 | 1,368 | 93,616 | 3,664 | 102,478 | 65 |
| Day 8 | 83,050 | 528 | 83,755 | 488 | 81,685 | 1,034 | 77,028 | 2,377 | 81,245 | 119 |
| Day 12 | 54,950 | 236 | 54,982 | 215 | 55,818 | 491 | 53,003 | 1,062 | 57,762 | 65 |
| Day 16 | 53,801 | 158 | 57,730 | 186 | 55,935 | 446 | 55,935 | 938 | 53,512 | 54 |

FIG. 11A
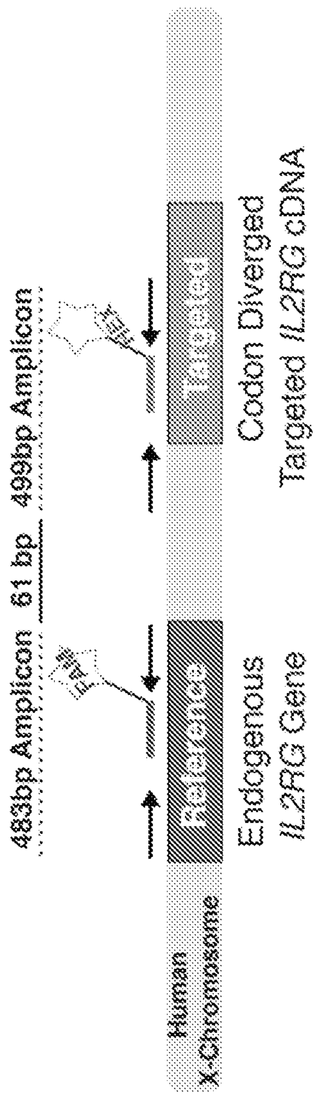
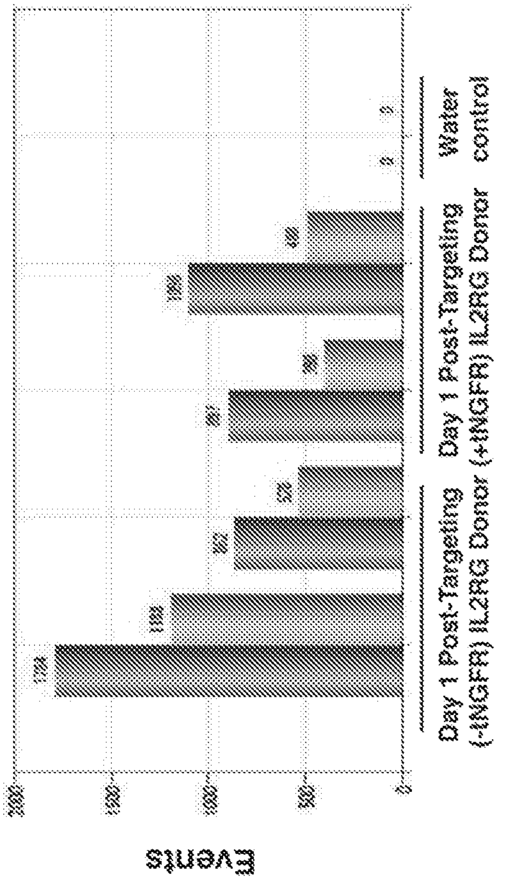
FIG. 11B
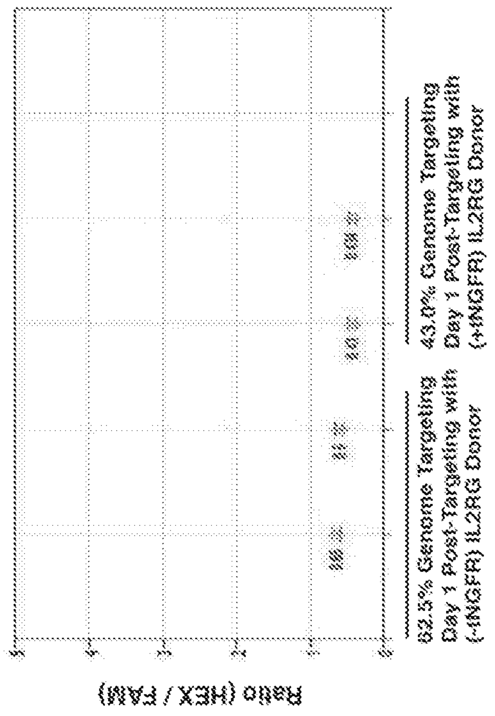
FIG. 11C

FIG. 11D
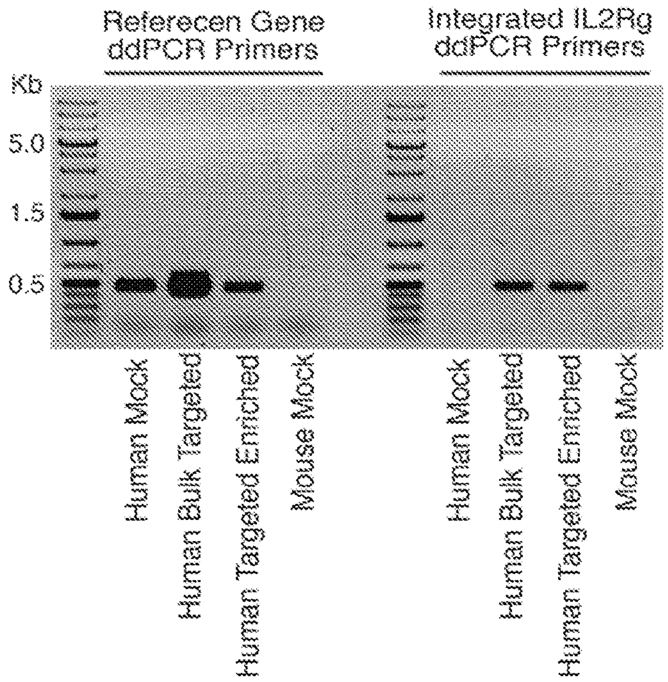
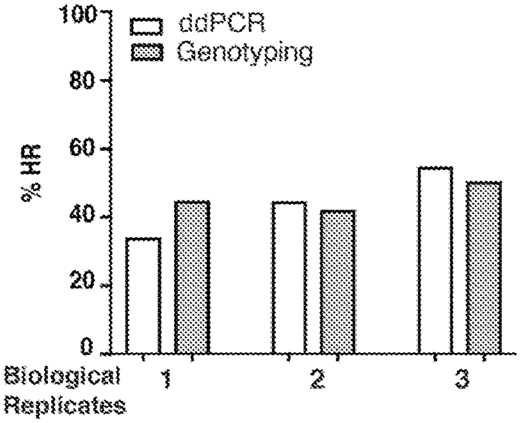
FIG. 11E
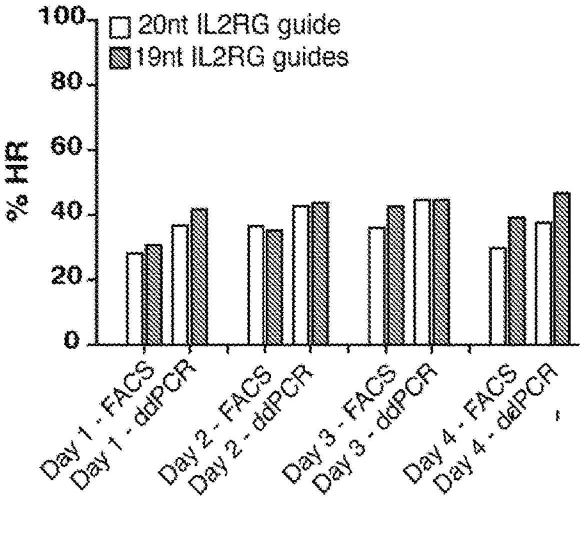
FIG. 11F

FIG. 21A
WT CD34+ HSPCs
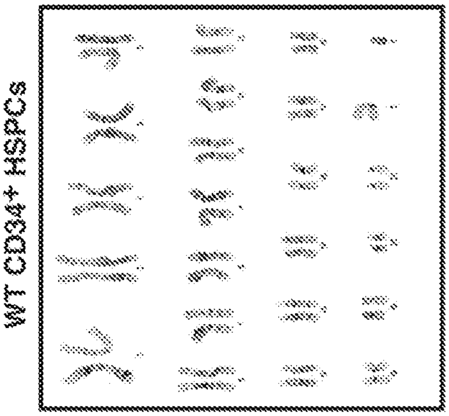
FIG. 21B
Mock CD34+ HSPCs
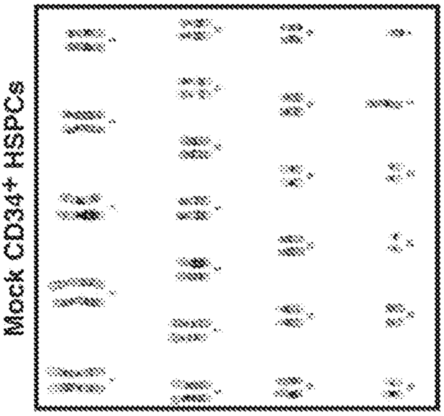
FIG. 21C
RNP only CD34+ HSPCs
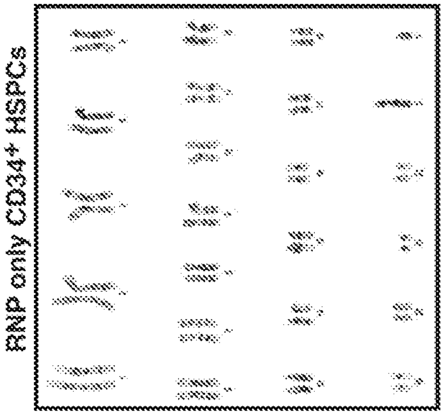
AAV6 + RNP CD34+ HSPCs
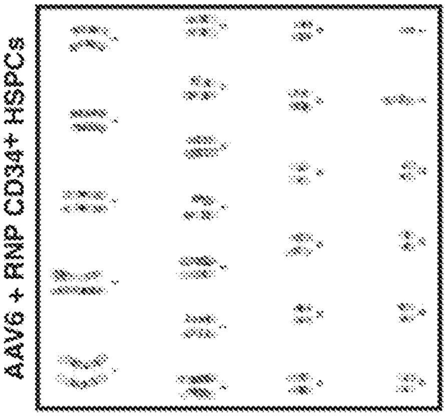
FIG. 21D
AAV6 only CD34+ HSPCs
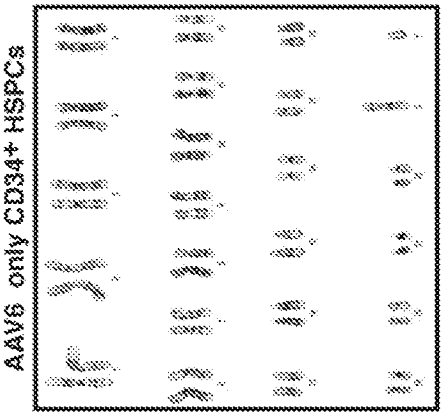
FIG. 21E FIG. 22A
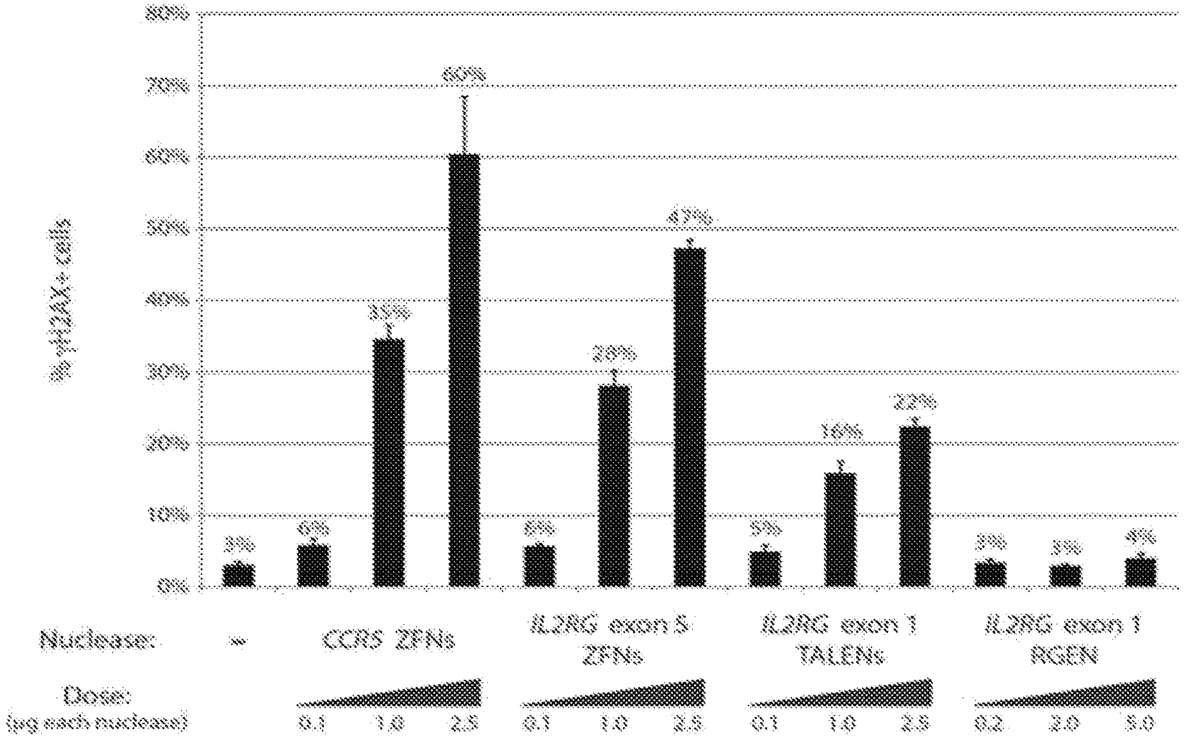
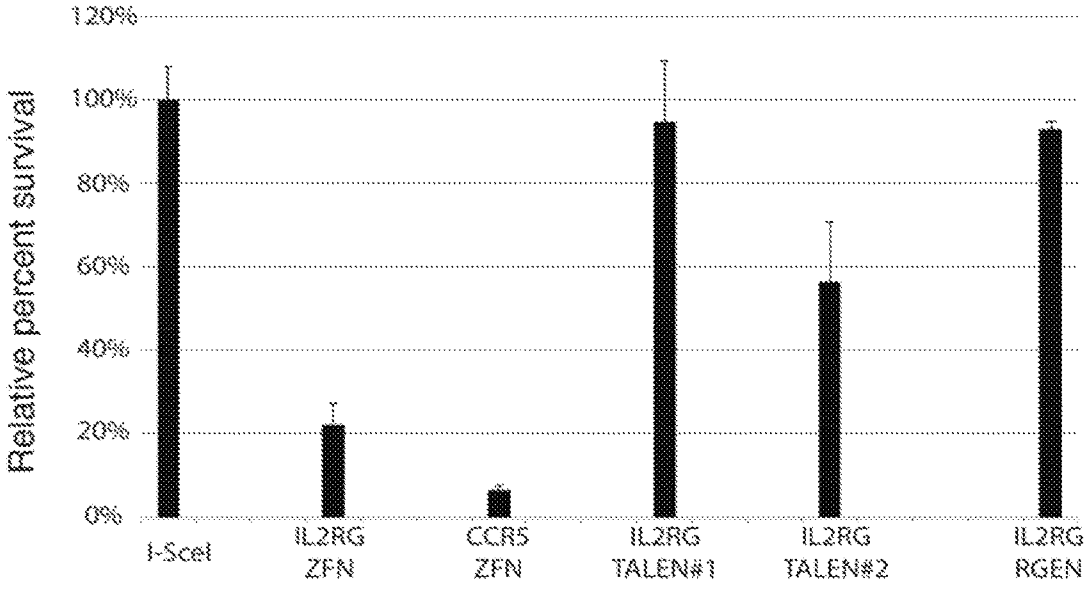
FIG. 22B

GENE CORRECTION FOR SCID-X1 IN LONG-TERM HEMATOPOIETIC STEM CELLS

CROSS REFERENCE TO RELATED APPLICATIONS

The present application is a U.S. National Phase 371 of PCT/US2021/044401, filed on Aug. 3, 2021, which claims priority to U.S. Provisional Pat. Appl. No. 63/060,586, filed on Aug. 3, 2020, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant No. R01 AI097320-01 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 22, 2021, is named 079445-1254395-004510PC_SL.txt and is 11,558 bytes in size.

BACKGROUND

X-linked Severe Combined Immunodeficiency (SCID-X1) is a primary immune deficiency disorder (PID) caused by mutations in the IL2RG gene on the X chromosome. The gene encodes a shared subunit of the receptors for interleukin-2 (IL-2), IL-4, IL-7, IL-9, IL-15, and IL-21. Without early treatment, affected male infants die in the first year of life from infections. Although allogeneic hematopoietic cell transplant (allo-HCT) is considered the standard of care for SCID-X1, it holds significant risks due to potential incomplete immune reconstitution, graft versus host disease (GvHD) and a decreased survival rate in the absence of a human leukocyte antigen (HLA)-matched sibling donor (1). Because of the selective advantage of lymphoid progenitors expressing normal IL2RG, however, only a small number of genetically corrected hematopoietic stem and progenitor cells (HSPCs) are needed to reconstitute T-cell immunity (2,3). The importance of achieving gene correction in long-term hematopoietic stem cells (LT-HSCs) to achieve sustained clinical benefit is demonstrated by the waning of a functional immune system in patients who do not derive their immune system from LT-HSCs with a wild-type IL2RG gene.

Gene therapy is an alternative therapy to allo-HSCT. Using integrating viral vectors, such as gamma-retroviral and lentiviral vectors, extra copies of a functional IL2RG gene are semi-randomly integrated into the genome of SCID-X1 patient-derived $CD34^+$ HSPCs. This strategy has resulted in both successes and setbacks. While most patients treated with first generation of gene therapy survived and benefited from the therapy, a substantial fraction (>25%) of patients developed leukemia from insertional oncogenesis (4-6). It is concerning that patients developed leukemia from insertional oncogenesis both early and late, 15 years after transplantation of retroviral-based engineered cells (7). Constitutive activation of the transgene (8), the choice of vectors (9), and specific details of the gene therapy procedure have all been proposed as factors contributing to the risk of leukemia and myelodysplastic syndrome that occurred in several trials for primary immunodeficiency disorders (PIDs) including SCID-X1 (10,11), chronic granulomatous disease (CGD) (12,13) and Wiskott-Aldrich Syndrome (WAS) (14). With second-generation self-inactivating (SIN) vectors, multiple SCID-X1 patients have successfully reconstituted T-cell immunity in the absence of early leukemic events (15-17) with a follow-up of up to 7 years. However, the follow-up of these therapies remains too short to assess the long-term genotoxicity risk of the newer generation vectors, as transformation of T cell growth can take >10 years to manifest (7).

A potential alternative to the semi-random delivery of the complementary DNA (cDNA) is to use a targeted genome editing (GE) approach. GE is a means to alter the DNA sequence of a cell, including somatic stem cells, with nucleotide precision. Using homologous recombination-mediated GE (HR-GE), the approach can target a cDNA transgene into its endogenous locus, thereby preserving normal copy number and upstream and downstream non-coding elements that regulate expression (18-20). The highest frequencies of GE are achieved using an engineered nuclease to create a site-specific double-strand break (DSB) in the cell's genomic DNA (21,22). When the DSB is repaired by non-homologous end joining (NHEJ), small insertions and deletions (INDELs) can be created at a specific genomic target site—an outcome that is not generally useful for correcting mutant genes (23,24). In contrast, when the DSB is repaired by either HR (using a classic gene-targeting donor vector) or by single-stranded template repair (using a single-stranded oligonucleotide (ssODN)), precise sequence changes can be introduced, thereby providing a method to precisely revert disease-causing DNA variants (25).

Among the multiple GE platforms that use artificial nucleases to generate DSBs (18, 26-29), the CRISPR-Cas9 system has accelerated the field of GE because of its ease of use and high activity in a wide variety of cells. When CRISPR-Cas9 is delivered into primary human cells, including human $CD34^+$ HSPCs as a ribonucleoprotein (RNP) complex using fully synthesized single-guide RNA molecules (sgRNAs) with end modifications to protect the guide from exonuclease degradation, high frequencies of INDELs are achieved (30). Moreover, when the delivery of an RNP complex is combined with delivery of the gene-targeting donor molecule in a recombinant AAV6 (rAAV6) viral vector, high frequencies of homologous-mediated editing in human HSPCs can be obtained (25). The use of rAAV6 donor vectors have been successfully used with other nuclease systems as well, including zinc-finger nucleases (ZFNs) and in other cell types, such as primary human T cells (19, 31-32). Therefore, this HR-GE approach could transform the semi-random nature of viral-based gene therapy to a more controlled and precise strategy. By using AAV6 as a classic gene-targeting donor, in contrast to ssODNs, a full cDNA can be introduced at the endogenous target.

However, key challenges remain for translating GE into medical therapies for SCID-X1, including attaining clinically relevant targeted integration frequencies into LT-HSCs, attaining functional levels of protein expression, and establishing lack of toxicity. There is therefore a need for new methods that allow for the successful treatment of SCID-X1 by overcoming such challenges. The present disclosure satisfies this need and provides other advantages as well.

BRIEF SUMMARY

The present disclosure provides methods and compositions for treating X-linked Severe Combined Immunodeficiency (SCID-X1) in subjects, in particular through the genetic modification of cells taken from the subjects by integrating a full-length, functional copy of a IL2RG cDNA at the endogenous IL2RG locus in the cells, and subsequently reintroducing the modified cells back into the subject. In particular, the present methods and compositions involve the homologous-recombination-mediated introduction of functional, codon-optimized IL2RG cDNAs into the genomes of cells at the IL2RG locus, such that the functional IL2RG cDNA is expressed in the cells under the control of the endogenous IL2RG promoter and other regulatory elements.

In one aspect, the present disclosure provides a method of genetically modifying a cell from a subject with X-linked Severe Combined Immunodeficiency (SCID-X1), the method comprising: introducing into a cell isolated from the subject a single guide RNA (sgRNA) targeting the interleukin 2 receptor subunit gamma (IL2RG) gene, an RNA-guided nuclease, and a homologous donor template comprising a functional IL2RG cDNA, flanked by a first and a second IL2RG homology region; where the sgRNA binds to the nuclease and directs it to a target sequence within exon 1 of the IL2RG gene, whereupon the nuclease cleaves the gene at the target sequence, and where the cDNA is integrated by homology directed recombination (HDR) at the site of the cleaved IL2RG locus, such that the cDNA replaces the translational start site of the endogenous IL2RG gene and is expressed under the control of the endogenous IL2RG promoter, thereby providing functional IL2RG protein product in the cell. In some embodiments, the functional IL2RG cDNA comprises a nucleotide sequence having at least 80% identity to SEQ ID NO:11

In some embodiments of the method, the method further comprises isolating the cell from the subject prior to the introducing of the sgRNA, RNA-guided nuclease, and homologous donor template. In some embodiments, the sgRNA comprises a nucleotide sequence complementary to a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In some embodiments, the sgRNA comprises a nucleotide sequence complementary to SEQ ID NO:4. In some embodiments, the sgRNA comprises 2'-O-methyl-3'-phosphorothioate (MS) modifications at one or more nucleotides. In some such embodiments, the 2'-O-methyl-3'-phosphorothioate (MS) modifications are present at the three terminal nucleotides of the 5' and 3' ends. In some embodiments, the RNA-guided nuclease is Cas9. In some embodiments, the sgRNA and the RNA-guided nuclease are introduced into the cell as a ribonucleoprotein (RNP). In some embodiments, the RNP is introduced into the cell by electroporation.

In some embodiments, the IL2RG cDNA comprises a nucleotide sequence having at least 85%, 90%, 95%, 96%, 97%, 98%, 99%, 99.5%, 99.7%, 99.9% or more identity to SEQ ID NO:11. In some embodiments, the IL2RG cDNA comprises the nucleotide sequence of SEQ ID NO:11. In some embodiments, the homologous donor template further comprises a polyadenylation signal at the 3' end of the cDNA, where both the cDNA and the polyadenylation signal are flanked by the first and the second IL2RG homology regions on the template. In some such embodiments, the polyadenylation signal is a bovine growth hormone polyadenylation signal.

In some embodiments, the first and/or second IL2RG homology region comprises the nucleotide sequence of SEQ ID NO:1 or SEQ ID NO:2, or a fragment of SEQ ID NO:1 or SEQ ID NO:2. In some embodiments, the first and second IL2RG homology regions comprise the nucleotide sequences of SEQ ID NO:1 and SEQ ID NO:2. In some embodiments, the homologous donor template comprises the sequence of SEQ ID NO:12. In some embodiments, the homologous donor template is introduced into the cells using a recombinant adeno-associated virus (rAAV) serotype 6 vector.

In some embodiments, the homologous donor template further comprises a selectable marker. In some embodiments, the selectable marker is nerve growth factor receptor (NGFR) or a truncated form thereof (tNGFR). In some embodiments, the cell is a $CD34^+$ hematopoietic stem and progenitor cell (HSPC). In some such embodiments, the $CD34^+$ HSPC is isolated from the bone marrow or peripheral blood.

In another aspect, the present disclosure provides a method of treating a subject with SCID-X1, comprising (i) genetically modifying a cell from the subject using any of the herein-described methods, and (ii) reintroducing the cell into the subject.

In some embodiments of the method, the cell is reintroduced into the subject by systemic transplantation. In some embodiments, the systemic transplantation comprises intravenous administration. In some embodiments, the cell is reintroduced into the subject by local transplantation. In some embodiments, the local transplantation comprises intrafemoral or intrahepatic administration. In some embodiments, the cell is cultured and/or selected prior to being reintroduced into the subject.

In another aspect, the present disclosure provides an sgRNA that specifically targets exon 1 of the IL2RG gene, wherein the sgRNA comprises a nucleotide sequence complementary to the sequence of SEQ ID NO:4.

In some embodiments, the sgRNA comprises 2'-O-methyl-3'-phosphorothioate (MS) modifications at one or more nucleotides. In some such embodiments, the 2'-O-methyl-3'-phosphorothioate (MS) modifications are present at the three terminal nucleotides of the 5' and 3' ends.

In another aspect, the present disclosure provides a homologous donor template comprising: (i) an IL2RG cDNA comprising a nucleotide sequence comprising at least 80% identity to SEQ ID NO:11; (ii) a first IL2RG homology region located to one side of the cDNA within the donor template; and (iii) a second IL2RG homology region located to the other side of the cDNA within the donor template.

In some embodiments of the donor template, the first IL2RG homology region comprises the nucleotide sequence shown as SEQ ID NO:1, or a fragment thereof, and the second IL2RG homology region comprises the nucleotide sequence shown as SEQ ID NO:2, or a fragment thereof. In some embodiments, the IL2RG cDNA comprises a nucleotide sequence having at least 85%, 90%, 95%, 96%, 97%, 98%, 99%, 99.5%, 99.7%, 99.9%, or more identity to SEQ ID NO:11. In some embodiments, the IL2RG cDNA comprises the nucleotide sequence of SEQ ID NO:11. In some embodiments, the donor template further comprises a polyadenylation signal at the 3' end of the IL2RG cDNA, wherein both the cDNA and the polyadenylation signal are flanked by the first and second IL2RG homology regions on the template. In some embodiments, the template comprises the sequence of SEQ ID NO:12. In some embodiments, the donor template further comprises a selectable marker. In some such embodiments, the selectable marker is NGFR or a truncated form thereof (tNGFR).

In another aspect, the present disclosure provides an isolated HSPC comprising any of the herein-described sgRNAs and/or homologous donor templates.

In another aspect, the present disclosure provides an isolated, genetically modified HSPC comprising an exogenous, codon-optimized IL2RG cDNA integrated at the translation start site of the endogenous IL2RG gene, wherein the integrated cDNA comprises a nucleotide sequence having at least 80% identity to SEQ ID NO:11.

In some embodiments, the IL2RG cDNA comprises a nucleotide sequence having at least 85%, 90%, 95%, 96%, 97%, 98%, 99%, 99.5%, 99.7%, 99.9%, or more identity to SEQ ID NO:11. In some embodiments, the IL2RG cDNA comprises the nucleotide sequence of SEQ ID NO:11. In some embodiments, the HSPC was modified using any of the herein-described methods.

In another aspect, the present disclosure provides a pharmaceutical composition comprising a plurality of genetically modified autologous HSPCs comprising an exogenous, codon-optimized IL2RG cDNA integrated at the translation start site of the endogenous IL2RG gene, wherein the integrated cDNA comprises a nucleotide sequence having at least 80% identity to SEQ ID NO:11.

In some embodiments, the composition further comprises non-genetically modified autologous HSPCs and/or HSPCs comprising INDELS at the IL2RG locus. In some embodiments, the composition is comprised of at least 5% of genetically modified autologous HSPCs comprising the integrated IL2RG cDNA. In some embodiments, the composition is comprised of 9% to 50% of genetically modified autologous HSPCs comprising the integrated IL2RG cDNA.

BRIEF DESCRIPTION OF THE DRAWINGS

FIGS. 1A-1E. In vitro, medium scale genome targeting at IL2RG locus. FIG. 1A: Diagram of genomic integration and correction outcomes. FIG. 1B: Top: schematic of IL2RG corrective donors containing (+tNGFR) or not (—tNGFR) selectable marker. Bottom: IL2RG cDNA targeting frequencies of frozen mobilized peripheral blood $CD34^+$ HSPCs (white circles) or freshly purified cord blood male-derived $CD34^+$ HSCPs (red circles) derived from medium scale ($1.0\times10^6$) genome targeting and measured at day 4. Absolute targeting frequencies measured by ddPCR. Median: 23.2% (+tNGFR, n=11 biological replicates), median 45% (−tNGFR, n=13 biological replicates). FIG. 1C: Single cell-based methylcellulose assay from mock targeted (nucleofected only) or IL2RG cDNA targeted (−tNGFR donor) $CD34^+$ HSPCs. Absolute number of clones are shown (n=3 biological replicates). FIG. 1D: Fraction of the total for each type of colony scored. FIG. 1E: Gene correction outcome of SCID-X1 patient 2 derived $CD34^+$ HSPCs. Shown is the multi-lineage differentiation using OP9-idll1 In vitro system (n=23 wells). No growth was derived from uncorrected $CD34^+$ cells. LT-HSPCs long-term hematopoietic stem cells, ST-HSC short term hematopoietic stem cells, MPP multi-potent progenitor, CMP common myeloid progenitor, LMPP lymphoid multi-potent progenitor, CLP common lymphoid progenitor, HSPCs hematopoietic stem and progenitor cells, ddPCR droplet digital digital droplet PCR. Mean±s.e.m.; ns not specific (Welch's t-test).

FIGS. 2A-2E. Normal hematopoietic reconstitution from IL2RG cDNA targeted $CD34^+$ HSPCs. FIG. 2A: Timeline of primary (1°) and secondary (2°) human transplants into sub-lethally irradiated NSG mice. $CD34^+$ HSPCs are derived from umbilical cord blood of healthy male donors. Adult mice transplanted intra-femoral (IF) with either WT $CD34^+$ HSPCs (white circles) or mock targeted (yellow circles) or RNP only (black circles) or un-selected IL2RG cDNA targeted (blue-black circles) HSPCs. Three-4 days old NSG pups transplanted intra-hepatic (IH) with either mock or IL2RG targeted HSPCs. FIG. 2B: Combined IF and IH human cells engraftment ($hCD45^+$ HLA A-B-$C^+$) 16 weeks after 1° human transplant into indicated organs. FIG. 2C: % IL2RG cDNA targeted HSPCs within human graft in indicated organs, quantified by ddPCR. BM (n=24 mice), SP (n=24 mice), PB (n=6 mice) (*p=0.0008, one-way ANOVA). FIG. 2D: Percent human engraftment in indicated organs as in (FIG. 2**B) 16 weeks post 2° human $CD34^+$ HSPCs transplant into adult NSG mice. *p-value SP-IH=0.025, *p-value BM-IF=0.043 (Welch's t-test). FIG. 2E: % IL2RG targeted HSPCs quantied by ddPCR 32 weeks after engraftment. Median shown. BM bone marrow, SP spleen, PB peripheral blood.

FIG. 3A: Percent cellular composition of the lymphoid, myeloid and erythroid lineage derived from IH 1° human engraftment, shown in indicated organs and targeting conditions. $CD3^+$ BM: p=0.0017, $CD3^+$ SP: p=0.007 (Welch's t-test). FIG. 3B: Same as (FIG. 3A) but IF transplant analysis. $CD3^+$ SP: *p=0.023, $CD56^+$ BM: *p=0.015 (Kruskal-Wallis test). FIG. 3C: Percent cellular composition of the lymphoid, myeloid and erythroid lineage derived from secondary transplants. Data shown are combined IH and IF primary transplants. $CD3^+$ BM: *p=0.015, $CD56^+$: *p=0.025, $CD19^+$ SP: ***p=0.0002, $CD14^+$ SP: *p=0.0112, $CD11c^+$ SP: ***p=0.0004. LT long term. Error bars: mean±s.e.m.

FIGS. 4A-4F. In vivo rescue of SCID-X1 mutation. FIG. 4A: Genomic mapping and description of SCID-Xl mutations. FIG. 4B: Percent viability determined at indicated days pre- and post-targeting. Mock (nucleofected only), RNP (nucleofected with RNP only), RNP+AAV6 (nucleofected with RNP and transduced with AAV6-based IL2RG corrective donor). Shown is data for mobilized peripheral blood $CD34^+$ HSPCs (n=5). FIG. 4C: Medium scale ($1.0\times10^6$ cells) ex vivo genome targeting frequencies of frozen mobilized peripheral blood SCID-X1, at day 2 (blue-black circles, n=6). Arrow shows 45% genome targeting of SCID-X1 patient 2 derived $CD34^+$ HSPCs. FIG. 4D: Human cells engraftment analysis at week 17 after intra-hepatic (IH) delivery of IL2RG cDNA targeted (blue-black circles, n=15) or mutant $CD34^+$ HSPCs (gray circles, n=4). FIG. 4E: Percent cellular composition of the lymphoid, myeloid, and erythroid lineage derived from IL2RG corrected or mutant $CD34^+$ HSPCs. $CD3^+$: ****p<0.0001, $CD56^+$: *p=0.0146, $CD16^+$: p=0.0013, $CD19^+$: p=0.0015, $CD235a^+$: p=0.0022 (Welch's t-test). RNP ribonuclearprotein. FIG. 4F: Absolute numbers derived from (FIG. 4**E).

FIGS. 5A-5E. Evaluation of IL-2 receptor function in IL2RG cDNA targeted T cells. FIG. 5A: Schematic of signaling (pSTAT5—bottom) and proliferation (CFSE—top) in vitro assays. FIG. 5B: pSTAT5 assay derived FACS plots. Top: healthy male-derived T cells genome targeted with IL2RG cDNA tNGFR (KI) or with $tNGFR^+$ only cassette integrated at the IL2RG endogenous locus (KO). In red are the percent of double positive IL2RG-$tNGFR^+$ $pSTAT5^+$[4.42%/(4/42%+3.18%)]×100. We compare 58.2% cells (IL2RG targeted T cells) with 58.7% (IL2RG from WT T cells), (n=3 biological replicates). FIG. 5C: Quantification of IL-2R signaling through phosphoSTAT5 pathway. FIG. 5D: pSTAT5 MFI for WT, KI, and KO experiments from (b) p=0.02, Welch's t-test. WT T cells (gray circles, n=6), IL2RG KI (blue circles, n=3) and IL2RG KO (orange circles, n=3). FIG. 5E: Proliferation profile of CFSE labeled, TCR stimulated IL2RG cDNA tNGFR$^+$ sorted or mock-targeted T cells. Mock-targeted T cells are WT T cells cultured for the same amount of time as the tNGFR$^+$ targeted cells and have been nucleofected in the absence of RNP or absence of transduction with AAV6. Shown FACS analysis at days 2, 4, 6, and 8. pSTAT5 phosphorylated STAT5, CFSE carboxyfluorescein succinimidyl ester, KI knocked in, KO knocked out, tNGFR truncated nerve growth factor receptor, IL-2 interleukin 2.

FIGS. 6A-6F. Genome specificity of IL2RG sgRNA guide. FIG. 6A: Heat map of on-target INDEL frequencies quantied by NexGen-Seq at COSMID identified putative on-target locations from healthy CD34$^+$ HSPCs. Levels of NHEJ induced by 20 nt IL2RG sgRNA and truncated 19 nt, 18 nt and 17 nt pre-complexed with WT Cas9 protein at 5:1 molar ratio. FIG. 6B: Heat map as in (FIG. 6A) of on-target INDEL frequencies derived from 19 nt IL2RG sg-1 in the genome of CD34$^+$ HSPCs SCID-X1 patient 1 derived cells. c Percent viability at day 4 of SCID-X1 patient-derived CD34$^+$ HSPCs nucleofected with either wild-type (WT) or high-fidelity (HiFi) SpCas9 protein pre-complexed with either the 20 nt or the 19 nt IL2RG sg-1 (n=1). FIG. 6D: Percent INDELs measured by TIDE at day 4 in cells as in (FIG. 6C) using WT or HiFi Cas9 protein pre-complexed with the 20 nt IL2RG sg-1 (green bars) or 19 nt IL2RG sg-1 (blue bars). FIG. 6E: Percent IL2RG cDNA targeting (% HR) as measured by ddPCR at day 4 in cells as in (FIG. 6C) generated by either WT or HiFi Cas9 protein pre-complexed with the 20 nt IL2RG sg-1 or (FIG. 6F) 19 nt IL2RG sg-1.

(FIG. 7A) Schematic of IL2RG sgRNAs for exon 1. (FIG. 7B) Percent INDELs and (FIG. 7C) Percent viability at day 4 for IL2RG sgRNAs 1-7 nucleofected as RNP in UCB derived CD34$^+$ HSPCs (n=1). (FIG. 7D) Comparing percent INDELs of WT (20 nt) sg-1 IL2RG sgRNA to truncated versions (19 nt, 18 nt and 17 nt) at 1:2.5 molar ratio (n=2). (FIG. 7E) Next generation sequencing (NGS) analysis of samples from FIG. 7D (n=1). (FIG. 7F) Time course of percent INDELs generated by WT sg-1 IL2RG sgRNA (white bars) and 19 nt truncated IL2RG sgRNA (blue bars) (shown n=1). UCB, umbilical cord blood. Mean±s.e.m.

(FIG. 9A) Heat map of TIDE analysis of various RNP molar ratios as determined at day 4 post genome editing. Shown is percent on target INDELs (n=3, biological replicates). (FIG. 9B) Cellular viability at day 4-post nucleofection of various molar ratio RNPs. Measurement is based on trypan blue staining. Mean±s.e.m; PB, peripheral blood.

(FIG. 10A) Schematics of various symmetric and asymmetric arms of homology flanking a SFFV GFP cassette. (FIG. 10B) Targeting integration frequencies (% HR) quantified by FACS analysis. Donor A vs Donor D *p-value=0.0204; Donor B vs Donor C *p-value=0.0226; Donor C vs Donor D **p-value=0.0055; Donor D vs Donor E *p-value=0.0361 (unpaired t-test). Median is shown. CD34$^+$ HSPCs used in this experiment were derived from two different fresh UCB or mPB donors. n=4 healthy, male donors. UCB, umbilical cord blood, mPB, mobilized peripheral blood.

FIGS. 11A-11F. IL2RG specific digital droplet PCR (ddPCR) assay. (FIG. 11A) Schematic representation of the IL2RG specific ddPCR primers-probe design. (FIG. 11B) Positive droplets generated for the reference (FAM labeled—blue) and integrate (HEX labeled—green) IL2RG PCR amplicons. Genome targeting results using −tNGFR or +tNGFR IL2RG cDNA targeted donors at 24 h post rAAV6 transduction. (FIG. 11C) Ratio of integrated (HEX) to reference (FAM). Male derived genomic DNA contains only one allele of the human X-chromosome allowing for the ratio of the fluorescence signal to be a direct measurement of the levels of genome targeting. (FIG. 11D) Specificity of the ddPCR primer-probe set. (FIG. 11E) Comparison of ddPCR analysis of bulk IL2RG cDNA targeted male derived CD34$^+$ HSPCs and genotype of single cell sorted methylcellulose assay from the bulk population; n=3 (biological replicates). (FIG. 11F) Comparison of ddPCR and FACS analysis of targeted SFFV-GFP cassette targeted into IL2RG locus of male derived CD34$^+$ HSPCs. Time course day 1 through 4-post targeting is shown for full length (20 nt) and truncated (19 nt) IL2RG guide.

(FIG. 12A) Quantification of percent allelic targeting. Genotyping results derived from day 2 post IL2RG genome targeting, n=3 biological replicates, male derived frozen mobilized PB CD34$^+$ HSPCs. (FIG. 12B) Representative genotyping gel images. Colonies obtained at 14 days from individual wells of methylcellulose plates are scored and genotypes using a 3-primer PCR approach. Shown are genotyping results of biological replicate #2 from (FIG. 12A). WT—wild type; NTC—no template control; PB—peripheral blood.

(FIG. 16A) $1.0\times10^5$ CD34$^+$ HSPCs derived from male, frozen mobilized PB source nucleofected with RNP system at 5:1 molar ratio. Percent INDELs determined by TIDE analysis at 8, 12 and 16 weeks post 1° IH engraftment into NSG pups. (FIG. 16B) INDEL spectrum characterization generated by truncated 19 nt IL2RG sg-1 at day 4-post nucleofection of male derived CD34$^+$ HSPCs. Analysis was carried out at clonal level: 96 clones obtained from TOPO cloning bulk RNP sample. IL2RG alleles obtained from each clone were sequenced and their INDELs' distribution determined by TIDE analysis.

(FIG. 19A) Human engraftment of mutant or IL2RG targeted HSPCs in bone marrow (BM, n=5) or spleen (SP, n=6) 20 weeks after transplant (median plotted). (FIG. 19B) ddPCR quantification of levels of IL2RG codon-optimized cDNA present in BM (n=2) and SP (n=1) samples. (FIG. 19C) Percent composition of lymphoid, myeloid and erythroid present in SP 20 weeks post-transplant. (FIG. 19D) Same as (FIG. 19A) using SCID-X1 patient 3 derived $CD34^+$ HSPCs mutant cells (n=4) and IL2RG targeted cells (n=7) 17 weeks after transplant. Multiple t-test, Holm-Sidak test, median plotted. (FIG. 19E) Same as (FIG. 19B), n=4. (FIG. 19F) Same as (FIG. 19C) **p-value=0.0073, ns, not significant.

FIGS. 21A-21E. Karyotype analysis of IL2RG cDNA genome edited and genome targeted cord blood derived $CD34^+$ HSPCs. $5.0\times10^5$ cells were nucleofected at day 2 post ex-vivo cell culturing with RNP at 5:1 molar ratio. Conditions (FIG. 21D) and (FIG. 21E) received rAAV6 with −tNGFR IL2RG clinical donor at an MOI of 200,000 vgc/ul. Day 2 post transduction, cells were collected and prepared the same day for karyotype analysis. 20 cells were analyzed per condition. Conditions (FIG. 21C) and (FIG. 21D) and conditions (FIG. 21D) and (FIG. 21E) show that a combined 40/40 cells treated with RNP or with rAAV6, respectively did not produced cells with chromosomal abnormalities. vgc: viral genome copies.

FIGS. 22A-22B. Genotoxicity of IL2RG exon 1 TALENs, IL2RG exon 5 ZFNs, CCR5 ZFNs, and an IL2RG exon 1 RGEN (CRISPR-Cas9). (FIG. 22A) yH2AX assay. Genotoxicity assay measuring DNA damage induced by different classes of engineered nucleases by assessing the phosphorylation of histone H2AX, a marker of DSB formation, in K562 cells. Percentage $yH2AX^+$ was measured by flow cytometry 48 h post-nucleofection. (FIG. 22B) Relative cell survival assay. Levels of genotoxicity induced by different classes of engineered nucleases in 293T cell line. Cells were nucleofected with GFP plasmid DNA and genome wide off-target activity of each nuclease was determined by FACS analysis as percent $GFP^+$ cells relative to I-SceI control. Bars: n=3, mean±s.d.

DETAILED DESCRIPTION

1. Introduction

Figures 3A, 3B, 3C:
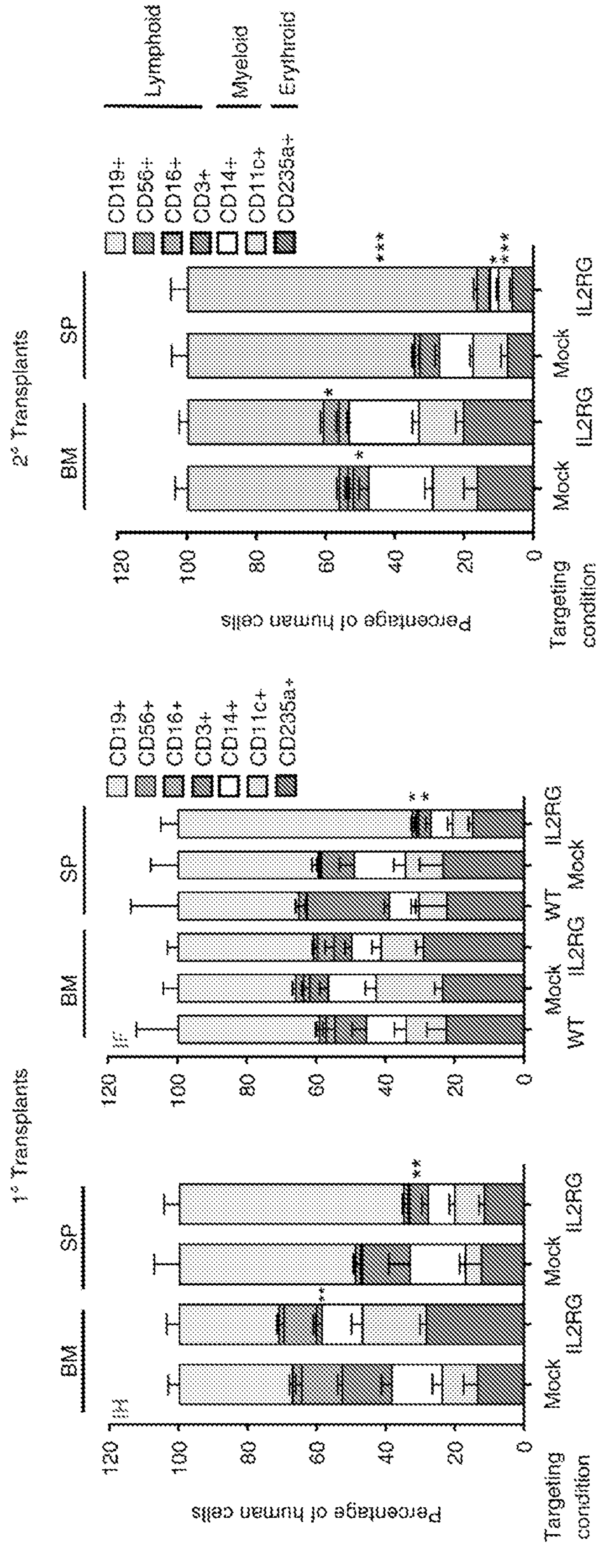
FIGS. 3A-3C. Normal multi-lineage development from IL2RG cDNA targeted in the LT-HSC population.

The present disclosure provides methods and compositions for the treatment of X-linked Severe Combined Immunodeficiency (SCID-X1) in subjects, through the introduction and integration at the endogenous IL2RG locus of functional, codon-optimized IL2RG cDNAs. The methods involve the introduction of ribonucleoproteins (RNPs) comprising single guide RNAs (sgRNAs) and RNA-guided nucleases (e.g., Cas9) into cells from the subject, as well as the introduction of homologous templates for repair. The cDNAs are integrated at the start site of the endogenous IL2RG gene, such that the cDNA is expressed under the control of the endogenous IL2RG promoter and other regulatory elements and functional protein is produced in the cell, thereby compensating for a genetic deficiency in the subject. In particular embodiments, the RNP complexes, e.g., comprising IL2RG sgRNA and Cas9 protein, are delivered to cells via electroporation, followed by the transduction of the homologous template using an AAV6 viral vector. The homologous templates for repair are constructed to have arms of homology centered around the cut site within the IL2RG locus, located on either side of the cDNA on the template. Transcription is terminated using an exogenous polyadenylation signal.

This system can be used to modify any human cell, and in particular embodiments $CD34^+$ HSPCs are used.

2. General

Practicing the present methods utilizes routine techniques in the field of molecular biology. Basic texts disclosing the general methods of use in this disclosure include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb), base pairs (bp), or nucleotides (nt). Sizes of single-stranded DNA and/or RNA can be given in nucleotides. These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

3. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The promoter can be a heterologous promoter.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. The promoter can be a heterologous promoter. In the context of promoters operably linked to a polynucleotide, a "heterologous promoter" refers to a promoter that would not be so operably linked to the same polynucleotide as found in a product of nature (e.g., in a wild-type organism).

As used herein, a polynucleotide or polypeptide is "heterologous" to an organism if the polynucleotide or polypeptide originates from a foreign species compared to the organism or, if from the same species, is modified from its original form. For example, when a promoter is said to be operably linked to a heterologous coding sequence, it means that the coding sequence is derived from one species whereas the promoter sequence is derived from another, different species; or, if both are derived from the same species, the coding sequence is not naturally associated with the promoter (e.g., is a genetically engineered coding sequence).

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "expression" and "expressed" refer to the production of a transcriptional and/or translational product, e.g., of an IL2RG cDNA or encoded protein. In some embodiments, the term refers to the production of a transcriptional and/or translational product encoded by a gene or a portion thereof. The level of expression of a DNA molecule in a cell may be assessed on the basis of either the amount of corresponding mRNA that is present within the cell or the amount of protein encoded by that DNA produced by the cell.

"IL2RG" or "interleukin 2 receptor subunit gamma", refers to a gene encoding the "cytokine receptor common subunit gamma," which is a common subunit of the receptors for a variety of interleukins (including IL-2, IL-4, IL-7, IL-9, IL-15, and IL-21). IL2RG is mutated in patients with SCID-X1, e.g., missense mutations, nonsense mutations, insertions, deletions, and splicing mutations, resulting in a lack of gene expression or the expression of nonfunctional protein. The full-length IL2RG cDNAs used in the present methods encode functional protein and thus restore protein activity in patients. The accession number for the human IL2RG gene is NCBI Gene ID 3561, and for the encoded protein it is UniProt P31785. A codon-optimized (or "codon diverged") version of the IL2RG cDNA, comprising 78% sequence homology to the endogenous, wild-type gene, is shown as SEQ ID NO:11. The present methods can be used with any patient with SCID-X1, with any IL2RG mutation, so long that the IL2RG locus retains a functional promoter and potentially other regulatory elements such that the integrated cDNA is expressed in cells from the patient.

SCID-X1 is an X-linked immunodeficiency disorder caused by mutations in IL2RG. Any of a variety of mutations in IL2RG, including missense mutations, nonsense mutations, insertions, deletions, and splicing mutations, can prevent the expression of functional encoded protein, resulting in an absence of mature T and NK lymphocytes and leaving the patient vulnerable to infection. The present methods can compensate for the deficiencies caused by such IL2RG mutations in patients, regardless of the nature or location of the mutations.

The term "treating" or "treatment" refers to any one of the following: ameliorating one or more symptoms of a disease or condition (e.g., SCID-X1); preventing the manifestation of such symptoms before they occur; slowing down or completely preventing the progression of the disease or condition (as may be evident by longer periods between reoccurrence episodes, slowing down or prevention of the deterioration of symptoms, etc.); enhancing the onset of a remission period; slowing down the irreversible damage caused in the progressive-chronic stage of the disease or condition (both in the primary and secondary stages); delaying the onset of said progressive stage; or any combination thereof.

As used herein, the terms “subject”, “individual” or “patient” refer, interchangeably, to a warm-blooded animal such as a mammal. In particular embodiments, the term refers to a human. A subject may have, be suspected of having, or be predisposed to, SCID-X1 as described herein. The term also includes livestock, pet animals, or animals kept for study, including horses, cows, sheep, poultry, pigs, cats, dogs, zoo animals, goats, primates (e.g. chimpanzee), and rodents. A “subject in need thereof” refers to a subject that has one or more symptoms of SCID-X1, that has received a diagnosis of SCID-X1, that is suspected of having or being predisposed to SCID-X1, that shows a deficiency of functional IL2RG or a polypeptide encoded by IL2RG as described herein, or that is thought to potentially benefit from increased expression of IL2RG as described herein.

An “effective amount” refers to an amount of a compound or composition, as disclosed herein effective to achieve a particular biological, therapeutic, or prophylatic result. Such results include, without limitation, the treatment of a disease or condition disclosed herein as determined by any means suitable in the art.

“Conservatively modified variants” applies to both amino acid and nucleic acid sequences. With respect to particular nucleic acid sequences, “conservatively modified variants” refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are “silent variations,” which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a “conservatively modified variant” where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. In some cases, conservatively modified variants of a protein can have an increased stability, assembly, or activity as described herein.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the N-terminal residue, which is numbered 1, in an unmodified wild-type polypeptide sequence.

As used in herein, the terms “identical” or percent “identity,” in the context of describing two or more polynucleotide or amino acid sequences, refer to two or more sequences or specified subsequences that are the same. Two sequences that are “substantially identical” have at least 60% identity, preferably 65%, 70%, 75%, 80%, 85%, 90%, 91%, 92%, 93%, 94%, 95%, 96%, 97%, 98%, 99%, 99.5%, 99.7%, 99.9%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. With regard to amino acid sequences, in some cases, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A “comparison window,” as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which is described in Altschul et al., (1990) *J. Mol. Biol.* 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra).

These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The "CRISPR-Cas" system refers to a class of bacterial systems for defense against foreign nucleic acids. CRISPR-Cas systems are found in a wide range of bacterial and archaeal organisms. CRISPR-Cas systems fall into two classes with six types, I, II, III, IV, V, and VI as well as many sub-types, with Class 1 including types I and III CRISPR systems, and Class 2 including types II, IV, V and VI; Class 1 subtypes include subtypes I-A to I-F, for example. See, e.g., Fonfara et al., *Nature* 532, 7600 (2016); Zetsche et al., *Cell* 163, 759-771 (2015); Adli et al. (2018). Endogenous CRISPR-Cas systems include a CRISPR locus containing repeat clusters separated by non-repeating spacer sequences that correspond to sequences from viruses and other mobile genetic elements, and Cas proteins that carry out multiple functions including spacer acquisition, RNA processing from the CRISPR locus, target identification, and cleavage. In class 1 systems these activities are effected by multiple Cas proteins, with Cas3 providing the endonuclease activity, whereas in class 2 systems they are all carried out by a single Cas, Cas9.

A "homologous repair template" refers to a polynucleotide sequence that can be used to repair a double stranded break (DSB) in the DNA, e.g., a CRISPR/Cas9-mediated break at the IL2RG locus as induced using the herein-described methods and compositions. The homologous repair template comprises homology to the genomic sequence surrounding the DSB, i.e., comprising IL2RG homology arms as described herein. In some embodiments, two distinct homologous regions are present on the template, with each region comprising at least 50, 100, 200, 300, 400, 500, 600, 700, 800, 900 or more nucleotides or more of homology with the corresponding genomic sequence. In particular embodiments, the templates comprise two homology arms comprising about 500 nucleotides of homology extending from either site of the sgRNA target site. The repair template can be present in any form, e.g., on a plasmid that is introduced into the cell, as a free floating doubled stranded DNA template (e.g., a template that is liberated from a plasmid in the cell), or as single stranded DNA. In particular embodiments, the template is present within a viral vector, e.g., an adeno-associated viral vector such as AAV6. The templates of the present disclosure also comprise a full-length, codon-optimized IL2RG cDNA, as well as, typically, a polyadenylation signal such as from bovine growth hormone.

As used herein, "homologous recombination" or "HR" refers to insertion of a nucleotide sequence during repair of double-strand breaks in DNA via homology-directed repair mechanisms. This process uses a "donor template" or "homologous repair template" with homology to nucleotide sequence in the region of the break as a template for repairing a double-strand break. The presence of a double-stranded break facilitates integration of the donor sequence. The donor sequence may be physically integrated or used as a template for repair of the break via homologous recombination, resulting in the introduction of all or part of the nucleotide sequence. This process is used by a number of different gene editing platforms that create the double-strand break, such as meganucleases, such as zinc finger nucleases (ZFNs), transcription activator-like effector nucleases (TALENs), and the CRISPR-Cas9 gene editing systems. In particular embodiments, HR involves double-stranded breaks induced by CRISPR-Cas9. In further embodiments, the CRISPR-Cas9 comprises high-fidelity Cas9 variants having improved on-target specificity and reduced off-target activity. Examples of high-fidelity Cas9 variants include but are not limited to those described in PCT Publication Nos. WO/2018/068053 and WO/2019/074542, each of which is herein incorporated by reference in its entirety.

As used herein, "functional IL2RG cDNA" refers to cDNA encoding an IL2RG protein having similar or equivalent protein function as wild-type IL2RG protein (UniProt P31785), which is referred to herein as "functional IL2RG protein." In some embodiments, functional IL2RG protein has at least 50%, 55%, 60%, 65%, 70%, 75%, 80%, 85%, 90%, 95%, 97%, 99%, 99.5%, 99.7%, 99.9% or 100% of the function of wild-type IL2RG protein, as determined by any method known in the art for assessing IL2RG protein function, including but not limited to assessment of signaling through IL-2R, and T and NK-cell development, proliferation and function, which are described in the Examples below.

4. CRISPR/CAS Systems Targeting the IL2RG Locus

The present disclosure provides methods and compositions for integrating functional IL2RG cDNAs into the endogenous IL2RG locus in cells from a subject with SCID-X1. In particular embodiments, the cells are hematopoietic stem and progenitor cells (HSPCs). The cells can be modified using the methods described herein and then reintroduced into the subject, wherein the expression of the cDNA in the modified cells in vivo can restore protein function and activity that is missing or deficient in the subject with SCID-X1.

The present disclosure is based in part on the identification of CRISPR guide sequences that specifically and effectively direct the cleavage of IL2RG, e.g., within exon 1 of IL2RG, by RNA-guided nucleases such as Cas9. In particular embodiments, the methods involve the introduction of ribonucleoproteins (RNPs) comprising an sgRNA targeting IL2RG and Cas9, as well as a template DNA molecule comprising IL2RG homology arms flanking a full-length, codon-optimized IL2RG cDNA. Using the present methods, high rates of targeted integration at the IL2RG locus and expression of the cDNA can be achieved, with the result that the transplantation and long-term engraftment of the modified cells can lead to a reduction or elimination of symptoms caused by the protein deficiency associated with SCID-X1.

sgRNAs

The single guide RNAs (sgRNAs) used in the present methods target the IL2RG locus. sgRNAs interact with a site-directed nuclease such as Cas9 and specifically bind to or hybridize to a target nucleic acid within the genome of a cell, such that the sgRNA and the site-directed nuclease co-localize to the target nucleic acid in the genome of the cell. The sgRNAs as used herein comprise a targeting sequence comprising homology (or complementarity) to a target DNA sequence at the IL2RG locus, and a constant region that mediates binding to Cas9 or another RNA-guided nuclease. The sgRNA can target any sequence within IL2RG adjacent to a PAM sequence. In some embodiments, the target sequence is within exon 1 of IL2RG. In particular embodiments, the target sequence of the sgRNA comprises one of the sequences s shown as SEQ ID NO:3 to SEQ ID NO:10, or a sequence having, e.g., at least 90%, 91%, 92%, 93%, 94%, 95%, 96%, 97%, 98%, 99%, or more identity to, e.g., comprising 1, 2, 3, or more nucleotide substitutions, additions or subtractions relative to, any one of SEQ ID NO:3 to SEQ ID NO:10. In particular embodiments, the sgRNA comprises the sequence shown as SEQ ID NO:4; in such embodiments, the target sequence is the truncated (19 nucleotide) sg-1 sequence s of SEQ ID NO:4, but not the full-length (20 nucleotide) sg-1 sequence of SEQ ID NO:3.

The targeting sequence of the sgRNAs may be, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or 15-25, 18-22, or 19-21 nucleotides in length, and shares homology with a targeted genomic sequence, in particular at a position adjacent to a CRISPR PAM sequence. The sgRNA targeting sequence is designed to be homologous to the target DNA, i.e., to share the same sequence with the non-bound strand of the DNA template or to be complementary to the strand of the template DNA that is bound by the sgRNA. The homology or complementarity of the targeting sequence can be perfect (i.e., sharing 100% homology or 100% complementarity to the target DNA sequence) or the targeting sequence can be substantially homologous (i.e., having less than 100% homology or complementarity, e.g., with 1-4 mismatches with the target DNA sequence).

Each sgRNA also includes a constant region that interacts with or binds to the site-directed nuclease, e.g., Cas9. In the nucleic acid constructs provided herein, the constant region of an sgRNA can be from about 70 to 250 nucleotides in length, or about 75-100 nucleotides in length, 75-85 nucleotides in length, or about 80-90 nucleotides in length, or 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length. The overall length of the sgRNA can be, e.g., from about 80-300 nucleotides in length, or about 80-150 nucleotides in length, or about 80-120 nucleotides in length, or about 90-110 nucleotides in length, or, e.g, 90, 91, 92, 93, 94, 95, 96, 97, 98, 99, 100, 101, 102, 103, 104, 105, 106, 107, 108, 109, or 110 nucleotides in length.

It will be appreciated that it is also possible to use two-piece gRNAs (cr:tracrRNAs) in the present methods, i.e., with separate crRNA and tracrRNA molecules in which the target sequence is defined by the crispr RNA (crRNA), and the tracrRNA provides a binding scaffold for the Cas nuclease.

In some embodiments, the sgRNAs comprise one or more modified nucleotides. For example, the polynucleotide sequences of the sgRNAs may also comprise RNA analogs, derivatives, or combinations thereof. For example, the probes can be modified at the base moiety, at the sugar moiety, or at the phosphate backbone (e.g., phosphorothioates). In some embodiments, the sgRNAs comprise 3' phosphorothiate internucleotide linkages, 2'-O-methyl-3'-phosphoacetate modifications, 2'-fluoro-pyrimidines, S-constrained ethyl sugar modifications, or others, at one or more nucleotides. In particular embodiments, the sgRNAs comprise 2'-O-methyl-3'-phosphorothioate (MS) modifications at one or more nucleotides (see, e.g., Hendel et al. (2015) Nat. Biotech. 33(9):985-989, the entire disclosure of which is herein incorporated by reference). In particular embodiments, the 2'-O-methyl-3'-phosphorothioate (MS) modifications are at the three terminal nucleotides of the 5' and 3' ends of the sgRNA.

The sgRNAs can be obtained in any of a number of ways. For sgRNAs, primers can be synthesized in the laboratory using an oligo synthesizer, e.g., as sold by Applied Biosystems, Biolytic Lab Performance, Sierra Biosystems, or others. Alternatively, primers and probes with any desired sequence and/or modification can be readily ordered from any of a large number of suppliers, e.g., ThermoFisher, Biolytic, IDT, Sigma-Aldritch, GeneScript, etc.

RNA-Guided Nucleases

Any CRISPR-Cas nuclease can be used in the method, i.e., a CRISPR-Cas nuclease capable of interacting with a guide RNA and cleaving the DNA at the target site as defined by the guide RNA. In some embodiments, the nuclease is Cas9 or Cpf1. In particular embodiments, the nuclease is Cas9. The Cas9 or other nuclease used in the present methods can be from any source, so long that it is capable of binding to an sgRNA as described herein and being guided to and cleaving the specific IL2RG sequence targeted by the targeting sequence of the sgRNA. In particular embodiments, the Cas9 is from *Streptococcus pyogenes.*

Also disclosed herein are CRISPR/Cas or CRISPR/Cpf1 systems that target and cleave DNA at the IL2RG locus. An exemplary CRISPR/Cas system comprises (a) a Cas (e.g., Cas9) or Cpf1 polypeptide or a nucleic acid encoding said polypeptide, and (b) an sgRNA that hybridizes specifically to IL2RG, or a nucleic acid encoding said guide RNA. In some instances, the nuclease systems described herein, further comprises a donor template as described herein. In particular embodiments, the CRISPR/Cas system comprises an RNP comprising an sgRNA targeting IL2RG and a Cas protein such as Cas9. In some embodiments, the Cas9 is a high fidelity (HiFi) Cas9 (see, e.g., Vakulskas, C. A. et al. A high-fidelity Cas9 mutant delivered as a ribonucleoprotein complex enables efficient gene editing in human hematopoietic stem and progenitor cells. Nat. Med. 24, 1216-1224 (2018)).

In addition to the CRISPR/Cas9 platform (which is a type II CRISPR/Cas system), alternative systems exist including type I CRISPR/Cas systems, type III CRISPR/Cas systems, and type V CRISPR/Cas systems. Various CRISPR/Cas9 systems have been disclosed, including *Streptococcus pyogenes* Cas9 (SpCas9), *Streptococcus thermophilus* Cas9

(StCas9), *Campylobacter jejuni* Cas9 (CjCas9) and *Neisseria cinerea* Cas9 (NcCas9) to name a few. Alternatives to the Cas system include the *Francisella novicida* Cpf1 (FnCpf1), *Acidaminococcus* sp. Cpf1 (AsCpf1), and *Lachnospiraceae* bacterium ND2006 Cpf1 (LbCpf1) systems. Any of the above CRISPR systems may be used to induce a single or double stranded break at the IL2RG locus to carry out the methods disclosed herein.

Introducing the sgRNA and Cas Protein into Cells

The sgRNA and nuclease can be introduced into a cell using any suitable method, e.g., by introducing one or more polynucleotides encoding the sgRNA and the nuclease into the cell, e.g., using a vector such as a viral vector or delivered as naked DNA or RNA, such that the sgRNA and nuclease are expressed in the cell. In some embodiments, one or more polynucleotides encoding the sgRNA, the nuclease or a combination thereof are included in an expression cassette. In some embodiments, the sgRNA, the nuclease, or both sgRNA and nuclease are expressed in the cell from an expression cassette. In some embodiments, the sgRNA, the nuclease, or both sgRNA and nuclease are expressed in the cell under the control of a heterologous promoter. In some embodiments, one or more polynucleotides encoding the sgRNA and the nuclease are operatively linked to a heterologous promoter. In particular embodiments, the sgRNA and nuclease are assembled into ribonucleoproteins (RNPs) prior to delivery to the cells, and the RNPs are introduced into the cell by, e.g., electroporation. RNPs are complexes of RNA and RNA-binding proteins. In the context of the present methods, the RNPs comprise the RNA-binding nuclease (e.g., Cas9) assembled with the guide RNA (e.g., sgRNA), such that the RNPs are capable of binding to the target DNA (through the gRNA component of the RNP) and cleaving it (via the protein nuclease component of the RNP). As used herein, an RNP for use in the present methods can comprise any of the herein-described guide RNAs and any of the herein-described RNA-guided nucleases.

Animal cells, mammalian cells, preferably human cells, modified ex vivo, in vitro, or in vivo are contemplated. Also included are cells of other primates; mammals, including commercially relevant mammals, such as cattle, pigs, horses, sheep, cats, dogs, mice, rats; birds, including commercially relevant birds such as poultry, chickens, ducks, geese, and/or turkeys.

In some embodiments, the cell is an embryonic stem cell, a stem cell, a progenitor cell, a pluripotent stem cell, an induced pluripotent stem (iPS) cell, a somatic stem cell, a differentiated cell, a mesenchymal stem cell or a mesenchymal stromal cell, a neural stem cell, a hematopoietic stem cell or a hematopoietic progenitor cell, an adipose stem cell, a keratinocyte, a skeletal stem cell, a muscle stem cell, a fibroblast, an NK cell, a B-cell, a T cell, or a peripheral blood mononuclear cell (PBMC). In particular embodiments, the cells are hematopoietic stem and progenitor cells (HSPCs), e.g., cord blood-derived (CB), adult peripheral blood-derived (PB), or bone marrow derived HSPCs.

To avoid immune rejection of the modified cells when administered to a subject, the cells to be modified are preferably derived from the subject's own cells. Thus, preferably the mammalian cells are autologous cells from the subject to be treated with the modified cells. In some embodiments, however, the cells are allogeneic, i.e., isolated from an HLA-matched or HLA-compatible, or otherwise suitable, donor.

In some embodiments, cells are harvested from the subject and modified according to the methods disclosed herein, which can include selecting certain cell types, optionally expanding the cells and optionally culturing the cells, and which can additionally include selecting cells that contain the transgene integrated into the IL2RG locus. In particular embodiments, such modified cells are then reintroduced into the subject.

Further disclosed herein are methods of using said nuclease systems to produce the modified host cells described herein, comprising introducing into the cell (a) an RNP of the present disclosure that targets and cleaves DNA at the IL2RG locus, and (b) a homologous donor template or vector as described herein. Each component can be introduced into the cell directly or can be expressed in the cell by introducing a nucleic acid encoding the components of said one or more nuclease systems.

Such methods will target integration of the functional IL2RG cDNA at the endogenous IL2RG locus in a host cell ex vivo. Such methods can further comprise (a) introducing a donor template or vector into the cell, optionally after expanding said cells, or optionally before expanding said cells, and (b) optionally culturing the cell.

In some embodiments, the disclosure herein contemplates a method of producing a modified mammalian host cell, the method comprising introducing into a mammalian cell: (a) an RNP comprising a Cas nuclease such as Cas9 and an sgRNA specific to the IL2RG locus, and (b) a homologous donor template or vector as described herein. The disclosure further contemplates a mammalian host cell composition, wherein the mammalian host cell comprises: (a) an RNP comprising a Cas nuclease such as Cas9 and an sgRNA specific to the IL2RG locus, and (b) a homologous donor template or vector as described herein.

In any of these methods, the nuclease can produce one or more single stranded breaks within the IL2RG locus, or a double stranded break within the IL2RG locus. In these methods, the IL2RG locus is modified by homologous recombination with said donor template or vector to result in insertion of the transgene into the locus. The methods can further comprise (c) selecting cells that contain the transgene integrated into the IL2RG locus.

Techniques for insertion of transgenes, including large transgenes, capable of expressing functional proteins, including enzymes, cytokines, antibodies, and cell surface receptors are known in the art (See, e.g. Bak and Porteus, Cell Rep. 2017 Jul. 18; 20(3): 750-756 (integration of EGFR); Kanojia et al., Stem Cells. 2015 October; 33(10): 2985-94 (expression of anti-Her2 antibody); Eyquem et al., Nature. 2017 Mar. 2; 543(7643):113-117 (site-specific integration of a CAR); O'Connell et al., 2010 PLoS ONE 5(8): e12009 (expression of human IL-7); Tuszynski et al., Nat Med. 2005 May; 11(5):551-5 (expression of NGF in fibroblasts); Sessa et al., Lancet. 2016 Jul. 30; 388(10043):476-87 (expression of arylsulfatase A in ex vivo gene therapy to treat MLD); Rocca et al., Science Translational Medicine 25 Oct. 2017: Vol. 9, Issue 413, eaaj2347 (expression of frataxin); Bak and Porteus, Cell Reports, Vol. 20, Issue 3, 18 Jul. 2017, Pages 750-756 (integrating large transgene cassettes into a single locus), Dever et al., Nature 17 Nov. 2016: 539, 384-389 (adding tNGFR into hematopoietic stem cells (HSC) and HSPCs to select and enrich for modified cells); each of which is herein incorporated by reference in its entirety.

Homologous Repair Templates

The IL2RG cDNA to be integrated, which is comprised of a polynucleotide or donor construct, can be any functional, codon-optimized IL2RG cDNA whose expression in cells can restore or improve protein levels in SCID-X1 patients and thereby allow normal, or clinically beneficial, T and NK cell development and function. In particular embodiments, the cDNA is integrated at the translational start site of the endogenous IL2RG locus, such that the cDNA is expressed under the control of the endogenous IL2RG promoter and other regulatory elements.

In particular embodiments, the IL2RG cDNA in the homologous repair template is codon-optimized, e.g., comprises at least 70%, 75%, 80%, 85%, 90%, 95%, or more homology to the wild-type IL2RG cDNA. In a particular embodiment, the IL2RG cDNA comprises about 75%, 76%, 77%, 78%, 79%, or 80%, homology to the wild-type IL2RG cDNA. In a particular embodiment, the IL2RG cDNA comprises the codon-optimized sequence shown as SEQ ID NO:11, or a derivative or fragment of SEQ ID NO:11, e.g., a sequence having about 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.7%, 99.9% or greater identity to SEQ ID NO:11 or to a fragment thereof. In particular embodiments, the template further comprises a polyA sequence or signal, e.g., a bovine growth hormone polyA sequence, at the 3' end of the cDNA.

In particular embodiments, the cDNA (or cDNA and polyA signal) is flanked in the template by IL2RG homology regions. For example, an exemplary template can comprise, in linear order: a first IL2RG homology region, an IL2RG cDNA, a polyA sequence such as a bovine growth hormone polyadenylation sequence (bGH-PolyA), and a second IL2RG homology region, where the first and second homology regions are homologous to the genomic sequences extending in either direction from the sgRNA target site. In particular embodiments, one of the homology regions comprises the sequence of SEQ ID NO:1, or a fragment thereof, or to a sequence having 80%, 85%, 90%, 95%, 96%, 97%, 98%, 99%, 99.5%, 99.7%, 99.9% or greater identity to SEQ ID NO:1, or a fragment thereof. In particular embodiments, the other homology region comprises the sequence of SEQ ID NO:2, or a fragment thereof, or to a sequence having 80%, 85%, 90%, 95%, 96%, 97%, 98%, 99%, 99.5%, 99.7%, 99.9%, or greater identity to SEQ ID NO:2, or a fragment thereof. The homology regions can be of any size, e.g., 100-1000 bp, 300-800 bp, 400-600 bp, or about 100, 200, 300, 400, 500, 600, 700, 800, 900, 1000, or more bp. In particular embodiments, the homology regions are about 400-500 bp in size.

In particular embodiments, the homologous repair template comprises the sequence shown as SEQ ID NO:12. In other embodiments, the homologous repair template comprises a sequence having 80%, 85%, 90%, 95%, 96%, 97%, 98%, 99%, 99.5%, 99.7%, 99.9% or greater identity to SEQ ID NO:12, or a fragment thereof.

Any suitable method can be used to introduce the polynucleotide, or donor construct, into the cell. In particular embodiments, the polynucleotide is introduced using a recombinant adeno-associated viral vector (rAAV). For example, the rAAV can be from serotype 1 (e.g., an rAAV1 vector), 2 (e.g., an rAAV2 vector), 3 (e.g., an rAAV3 vector), 4 (e.g., an rAAV4 vector), 5 (e.g., an rAAV5 vector), 6 (e.g., an rAAV6 vector), 7 (e.g., an rAAV7 vector), 8 (e.g., an rAAV8 vector), 9 (e.g., an rAAV9 vector), 10 (e.g., an rAAV10 vector), or 11 (e.g., an rAAV11 vector). In particular embodiments, the vector is an rAAV6 vector. In some instances, the donor template is single stranded, double stranded, a plasmid or a DNA fragment. In some instances, plasmids comprise elements necessary for replication, including a promoter and optionally a 3' UTR.

Further disclosed herein are vectors comprising (a) one or more nucleotide sequences homologous to the IL2RG locus, and (b) an IL2RG cDNA as described herein. The vector can be a viral vector, such as a retroviral, lentiviral (both integration competent and integration defective lentiviral vectors), adenoviral, adeno-associated viral or herpes simplex viral vector. Viral vectors may further comprise genes necessary for replication of the viral vector.

In some embodiments, the targeting construct comprises: (1) a viral vector backbone, e.g. an AAV backbone, to generate virus; (2) arms of homology to the target site of at least 200 bp but ideally at least 400 bp on each side to assure high levels of reproducible targeting to the site (see, Porteus, Annual Review of Pharmacology and Toxicology, Vol. 56:163-190 (2016); which is hereby incorporated by reference in its entirety); (3) an IL2RG cDNA encoding a functional protein and capable of expressing the functional protein; and optionally (4) an additional marker gene to allow for enrichment and/or monitoring of the modified host cells. Any AAV known in the art can be used. In some embodiments the primary AAV serotype is AAV6.

Suitable marker genes are known in the art and include Myc, HA, FLAG, GFP, truncated NGFR, truncated EGFR, truncated CD20, truncated CD19, as well as antibiotic resistance genes. In some embodiments, the homologous repair template and/or vector (e.g., AAV6) comprises an expression cassette comprising a coding sequence for truncated nerve growth factor receptor (tNGFR), operably linked to a promoter such as the Ubiquitin C promoter.

In any of the preceding embodiments, the donor template or vector comprises a nucleotide sequence homologous to a fragment of the IL2RG locus, optionally to the sequences shown as SEQ ID NO:1 and/or SEQ ID NO:2 or fragments thereof, wherein the nucleotide sequence is at least 85%, 88%, 90%, 92%, 95%, 98%, 99%, 99.5%, 99.7%, or 99.9% identical to at least 200, 250, 300, 350, 400, 450, 500, or more consecutive nucleotides of the IL2RG locus, e.g., of SEQ ID NO:1 and/or SEQ ID NO:2.

The inserted construct can also include other safety switches, such as a standard suicide gene into the locus (e.g. iCasp9) in circumstances where rapid removal of cells might be required due to acute toxicity. The present disclosure provides a robust safety switch so that any engineered cell transplanted into a body can be eliminated, e.g., by removal of an auxotrophic factor. This is especially important if the engineered cell has transformed into a cancerous cell.

5. Methods of Treatment

Following the integration of the cDNA into the genome of the cell, e.g., HSPC, and confirming expression of the encoded protein, a plurality of modified cells can be reintroduced into the subject, such that they can repopulate and differentiate into, e.g., T cells or NK cells, and due to the expression of the integrated cDNA, can improve one or more abnormalities or symptoms in the subject with SCID-X1. In some embodiments, the cells are expanded, selected, and/or induced to undergo differentiation, prior to reintroduction into the subject.

Disclosed herein, in some embodiments, are methods of treating SCID-X1 in an individual in need thereof, the method comprising providing to the individual a protein replacement therapy using the genome modification methods disclosed herein. In some instances, the method comprises administering to the individual a modified host cell comprising a functional IL2RG cDNA, integrated at the IL2RG locus, wherein said modified host cell expresses the encoded protein which is otherwise deficient in the individual, thereby treating the SCID-X1 in the individual. In some embodiments, the modified host cell is modified ex vivo.

Pharmaceutical Compositions

Disclosed herein, in some embodiments, are methods, compositions and kits for use of the modified cells, including pharmaceutical compositions, therapeutic methods, and methods of administration. Although the descriptions of pharmaceutical compositions provided herein are principally directed to pharmaceutical compositions which are suitable for administration to humans, it will be understood by the skilled artisan that such compositions are generally suitable for administration to any animals. In some embodiments, the modified cells of the pharmaceutical composition are autologous to the individual in need thereof. In other embodiments, the modified cells of the pharmaceutical composition are allogeneic to the individual in need thereof.

In some embodiments, a pharmaceutical composition comprising a modified host cell as described herein is provided. The modified host cell is genetically engineered to comprise an integrated IL2RG cDNA at the IL2RG locus. In particular embodiments, a functional codon-optimized IL2RG cDNA is integrated into the translational start site of the endogenous IL2RG locus. In particular embodiments, the functional codon-optimized IL2RG cDNA that is integrated into the host cell genome is expressed under control of the native IL2RG promoter sequence. In some embodiments, the pharmaceutical composition comprises a plurality of the modified host cells, and further comprises unmodified host cells and/or host cells that have undergone nuclease cleavage resulting in INDELS at the IL2RG locus but not integration of the IL2RG cDNA. In some embodiments, the pharmaceutical composition is comprised of at least 5% of the modified host cells comprising an integrated IL2RG cDNA. In some embodiments, the pharmaceutical composition is comprised of about 9% to 50% of the modified host cells comprising an integrated IL2RG cDNA. In some embodiments, the pharmaceutical composition is comprised of about 5% to 80% of the modified host cells comprising an integrated IL2RG cDNA, or 5% to 75%, 5% to 70%, 5% to 65%, 5% to 60%, 5% to 55%, or 5% to 50% of the modified host cells comprising an integrated IL2RG cDNA. In some embodiments, the pharmaceutical composition is comprised of about 10% to 80% of the modified host cells comprising an integrated IL2RG cDNA, or 10% to 75%, 10% to 70%, 10% to 65%, 10% to 60%, 10% to 55%, or 10% to 50% of the modified host cells comprising an integrated IL2RG cDNA. In some embodiments, the pharmaceutical composition is comprised of at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50% or more of the modified host cells comprising an integrated IL2RG cDNA. The pharmaceutical compositions described herein may be formulated using one or more excipients to, e.g.: (1) increase stability; (2) alter the biodistribution (e.g., target the cells to specific tissues or cell types); (3) alter the release profile.

Formulations of the present disclosure can include, without limitation, saline, liposomes, lipid nanoparticles, polymers, peptides, proteins, and combinations thereof. Formulations of the pharmaceutical compositions described herein may be prepared by any method known or hereafter developed in the art of pharmacology. As used herein the term "pharmaceutical composition" refers to compositions including at least one active ingredient (e.g., a modified host cell) and optionally one or more pharmaceutically acceptable excipients. Pharmaceutical compositions of the present disclosure may be sterile.

Relative amounts of the active ingredient (e.g. the modified host cell), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, or at least 80% (w/w) active ingredient.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

Dosing and Administration

The modified host cells of the present disclosure included in the pharmaceutical compositions described above may be administered by any delivery route, systemic delivery or local delivery, which results in a therapeutically effective outcome. These include, but are not limited to, enteral, gastroenteral, epidural, oral, transdermal, intracerebral, intracerebroventricular, epicutaneous, intradermal, subcutaneous, nasal, intravenous, intra-arterial, intramuscular, intracardiac, intraosseous, intrathecal, intraparenchymal, intraperitoneal, intravesical, intravitreal, intracavernous), interstitial, intra-abdominal, intralymphatic, intramedullary, intrapulmonary, intraspinal, intrasynovial, intrathecal, intratubular, parenteral, percutaneous, periarticular, peridural, perineural, periodontal, rectal, soft tissue, and topical. In particular embodiments, the cells are administered intravenously. In certain embodiments, the composition may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

In some embodiments, a subject will undergo a conditioning regimen before cell transplantation. For example, before hematopoietic stem cell transplantation, a subject may undergo myeloablative therapy, non-myeloablative therapy or reduced intensity conditioning to prevent rejection of the stem cell transplant even if the stem cell originated from the same subject. The conditioning regime may involve administration of cytotoxic agents. The conditioning regime may also include immunosuppression, antibodies, and irradiation. Other possible conditioning regimens include antibody-mediated conditioning (see, e.g., Czechowicz et al., 318(5854) Science 1296-9 (2007); Palchaudari et al., 34(7) Nature Biotechnology 738-745 (2016); Chhabra et al., 10:8(351) Science Translational Medicine 351ra105 (2016)) and CAR T-mediated conditioning (see, e.g., Arai et al., 26(5) Molecular Therapy 1181-1197 (2018); each of which is hereby incorporated by reference in its entirety). For example, conditioning needs to be used to create space in the brain for microglia derived from engineered hematopoietic stem cells (HSCs) to migrate in to deliver the protein of interest (as in recent gene therapy trials for ALD and MLD). The conditioning regimen is also designed to create niche "space" to allow the transplanted cells to have a place in the body to engraft and proliferate. In HSC transplantation, for example, the conditioning regimen creates niche space in the bone marrow for the transplanted HSCs to engraft. Without a conditioning regimen, the transplanted HSCs cannot engraft.

Certain aspects of the present disclosure are directed to methods of providing pharmaceutical compositions including the modified host cell of the present disclosure to target tissues of mammalian subjects, by contacting target tissues with pharmaceutical compositions including the modified host cell under conditions such that they are substantially retained in such target tissues. In some embodiments, pharmaceutical compositions including the modified host cell include one or more cell penetration agents, although "naked" formulations (such as without cell penetration agents or other agents) are also contemplated, with or without pharmaceutically acceptable excipients.

The present disclosure additionally provides methods of administering modified host cells in accordance with the disclosure to a subject in need thereof. The pharmaceutical compositions including the modified host cell, and compositions of the present disclosure may be administered to a subject using any amount and any route of administration effective for preventing, treating, or managing the SCID-X1. The exact amount required will vary from subject to subject, depending on the species, age, and general condition of the subject, the severity of the disease, the particular composition, its mode of administration, its mode of activity, and the like. The subject may be a human, a mammal, or an animal. The specific therapeutically or prophylactically effective dose level for any particular individual will depend upon a variety of factors including the disorder being treated and the severity of the disorder; the activity of the specific payload employed; the specific composition employed; the age, body weight, general health, sex and diet of the patient; the time of administration, route of administration; the duration of the treatment; drugs used in combination or coincidental with the specific modified host cell employed; and like factors well known in the medical arts.

In certain embodiments, modified host cell pharmaceutical compositions in accordance with the present disclosure may be administered at dosage levels sufficient to deliver from, e.g., about $1\times10^4$ to $1\times10^5$, $1\times10^5$ to $1\times10^6$, $1\times10^6$ to $1\times10^7$, or more cells to the subject, or any amount sufficient to obtain the desired therapeutic or prophylactic, effect. The desired dosage of the modified host cell pharmaceutical compositions of the present disclosure may be administered one time or multiple times. In some embodiments, delivery of the modified host cell to a subject provides a therapeutic effect for at least 1 day, 2 days, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 20 months, 21 months, 22 months, 23 months, 2 years, 3 years, 4 years, 5 years, 6 years, 7 years, 8 years, 9 years, 10 years or more than 10 years.

The modified host cells may be used in combination with one or more other therapeutic, prophylactic, research or diagnostic agents, or medical procedures, either sequentially or concurrently. In general, each agent will be administered at a dose and/or on a time schedule determined for that agent.

Use of a modified mammalian host cell according to the present disclosure for treatment of SCID-X1 is also encompassed by the disclosure.

The present disclosure also contemplates kits comprising compositions or components of the present disclosure, e.g., sgRNA, Cas9, RNPs, and/or homologous templates, as well as, optionally, reagents for, e.g., the introduction of the components into cells. The kits can also comprise one or more containers or vials, as well as instructions for using the compositions in order to modify cells and treat subjects according to the methods described herein.

6. Examples

The present methods and compositions will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results.

Example 1. Gene Correction for SCID-X1 in Long-Term Hematopoietic Stem Cells Abstract Gene correction in human long-term hematopoietic stem cells (LT-HSCs) could be an effective therapy for monogenic diseases of the blood and immune system. Here we describe an approach for X-linked sSevere cCombined iImmunodeficiency (SCID-X1) using targeted integration of a cDNA into the endogenous start codon to functionally correct disease-causing mutations throughout the gene. Using a CRISPR-Cas9/AAV6 based strategy, we achieve up to 20% targeted integration frequencies in LT-HSCs. As measures of the lack of toxicity we observe no evidence of abnormal hematopoiesis following transplantation and no evidence of off-target mutations using a high-fidelity Cas9 as a ribonucleoprotein complex. We achieve high levels of targeting frequencies (median 45%) in $CD34^+$ HSPCs from six SCID- X1 patients and demonstrate rescue of lymphopoietic defect in a patient derived HSPC population in vitro and In vivo. In sum, our study provides specificity, toxicity and efficacy data supportive of clinical development of genome editing to treat SCID-X1.

Introduction

The present example describes a clinically relevant, selection-free "universal" CRISPR-Cas9-rAAV6 GE methodology that could potentially correct >97% of known IL2RG pathogenic mutations. We call this approach "functional gene correction" because it is not directly correcting a mutation but instead is doing so by using the targeted integration of cDNA to functionally correct downstream mutations. Approximately 2-3% of patients with deletions of the gene could not be functionally corrected using this strategy. We demonstrate that a functional, codon-optimized IL2RG cDNA can be precisely and efficiently integrated at the endogenous translational start site in $CD34^+$ HSPCs of healthy male donors (HD, n=13) or SCID-X1 patients (n=6) at comparable frequencies (median HR=45%) in both peripheral blood (PB)-derived and umbilical cord blood (CB)-derived $CD34^+$ HSPCs. We demonstrate the functionality of the full-length codon-optimized IL2RG cDNA by showing that T cells with the cDNA knock-in (KI) retain normal proliferation and signaling response to cytokines. Using transplantation into immunodeficient (NSG) mice, we show that process is both effective (with functional correction of 10-20% of LT-HSCs) and safe (no evidence of abnormal hematopoiesis). The In vivo functional results are based on transplantation of ~21 million IL2RG targeted healthy donor $CD34^+$ HSPCs and ~7 million IL2RG targeted SCID-X1-HSPCs. We demonstrate high levels of $CD34^+$ LT-HSC targeted cDNA integration (10-20%) by showing multi-lineage hematopoiesis derived from these cells using serial transplantation in immunodeficient mice. These results match and exceed the predicted therapeutic threshold determined through a mouse model (19). Finally, we show no evidence of significant genotoxicity as demonstrated by next-generation sequencing (NGS) and karyotype analysis. Together, this study establishes a pre-clinical proof-of-concept for a safe, precise, and highly efficient GE strategy to potentially cure SCID-X1.

Results

Gene Correction Strategy for IL2RG Locus in $CD34^+$ HSPCs

SCID-X1 is caused by pathogenic mutations spanning the entire IL2RG gene. Therefore, we developed a gene-targeting strategy by integrating a complete cDNA at the endogenous IL2RG translational start site (FIG. 1A, central panel) that would correct the vast majority (~97%) of known SCID-X1 pathogenic mutations and ensure regulated endogenous expression in $CD34^+$ HSPCs derived progeny. By achieving efficient integration frequencies in the genome of $CD34^+$ LT-HSCs, our approach could ensure life-long therapeutic benefits for the patient (FIG. 1A, right schematic).

Figure 7:
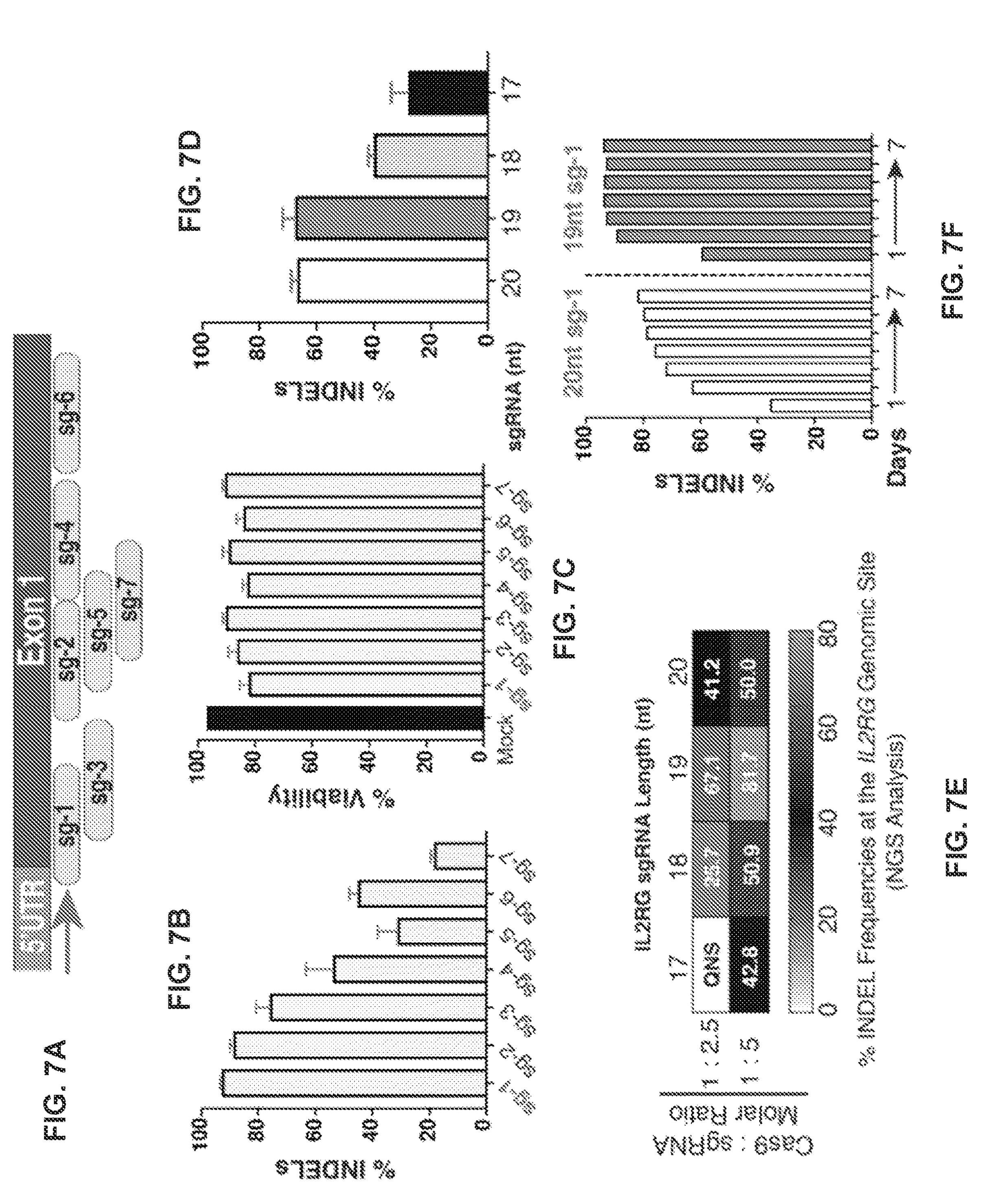
FIGS. 7A-7F. Screening and characterization of IL2RG sgRNA guides.
Figure 8:
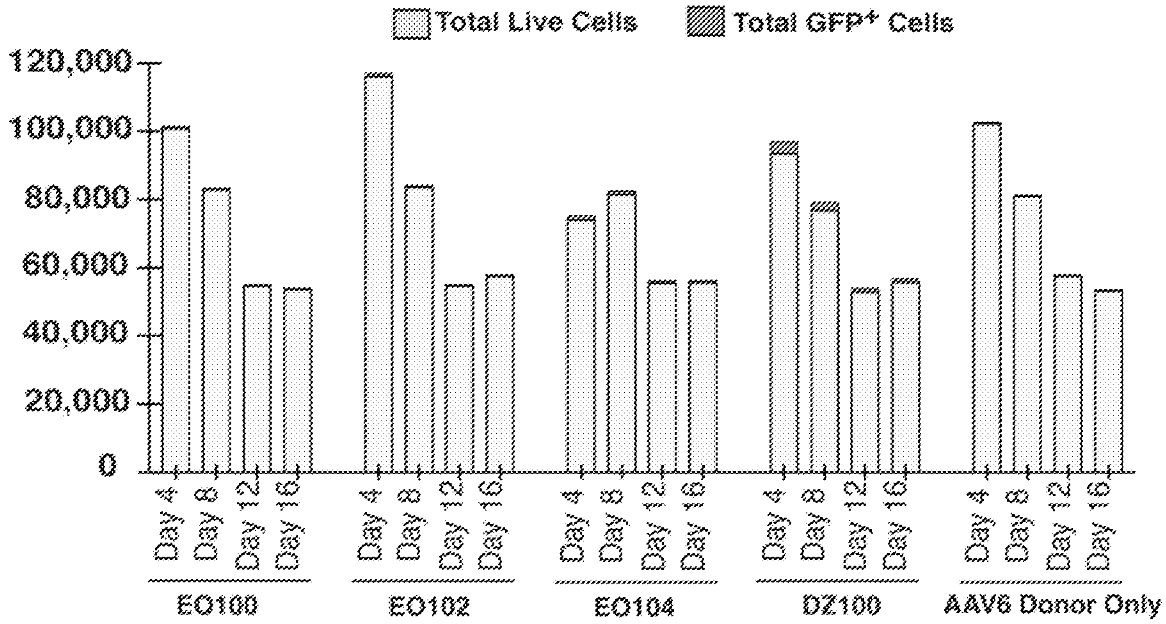
FIG. 8. Screening Lonza 4d nucleofection programs in human CD34$^+$ HSPCs. $1\times10^5$ cord blood derived CD34$^+$ HSPCs nucleofected with RNP at 1:2.5 molar ratio and transduced with AAV6 donor DNA virus for CCR5 locus at an MOI of 100,000, as determined by q-PCR. Total live cells as determined by trypan blue staining and % GFP$^+$ cells by flow cytometry (FACS).
Figure 9A:
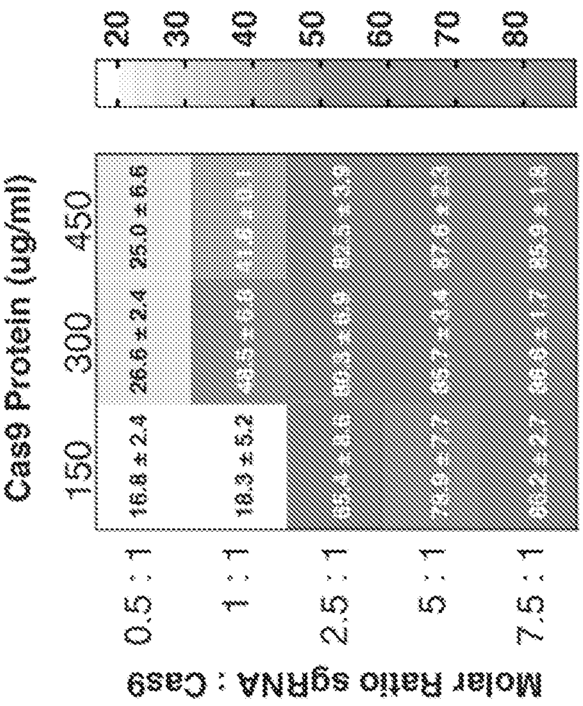
FIGS. 9A-9B. IL2RG sgRNA: WT Cas9 protein (RNP) molar ratios in mobilized PB CD34$^+$ HSPCs.
Figure 9B:
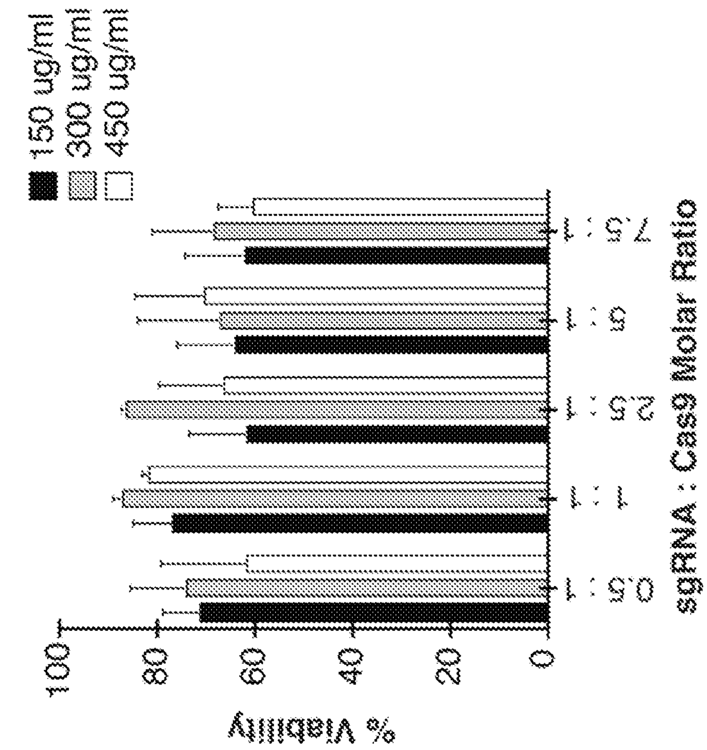

We screened seven different sgRNAs (single guide RNAs) for activity in exon 1 of the IL2RG gene (FIG. 7A) and selected sg-1, previously described (30), as the best candidate because of the location of the DSB it creates (one nucleotide downstream from the translational start site), on-target INDEL frequencies (92.9%±0.6, mean±s.e.m) (FIG. 7B) and for high cellular viability >80% (FIG. 7C). We found that a truncated sgRNA (33) of 19 nucleotides (19 nt) gave >90% INDEL frequencies (equivalent to the full 20 nt sgRNA) (FIGS. 7-9). NGS (FIG. 7E) further corroborated the INDELs obtained by TIDE analysis (34). We used the 19 nt gRNA at a medium scale process (1 million cells per electroporation) throughout the remaining experiments.

Figure 10B:
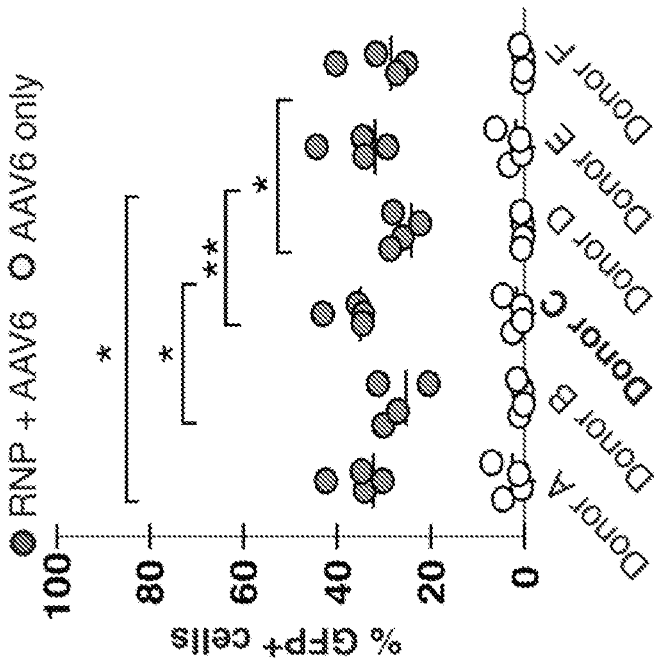
FIGS. 10A-10B. IL2RG homology arms length characterization.
Figure 10A:
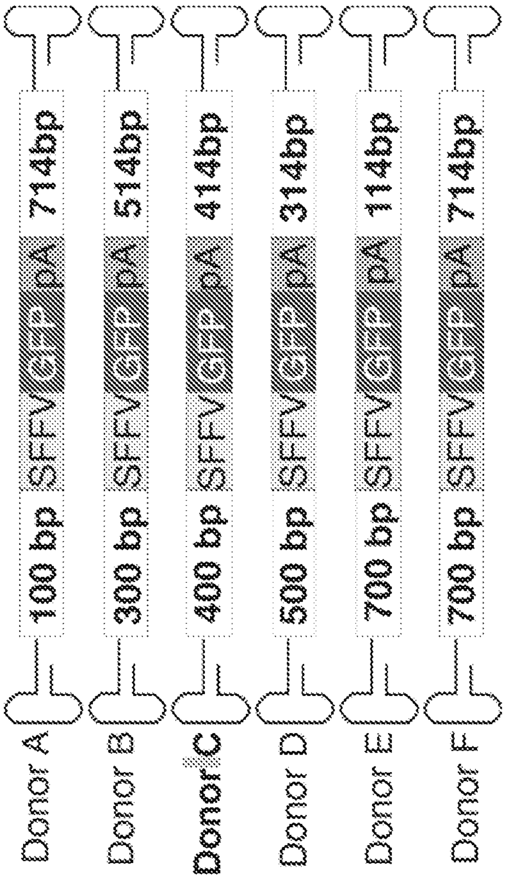

We designed a codon-optimized IL2RG cDNA functional correction donor with homology arms centered on the sg-1 guide sequence and cloned into an AAV6 vector both with and without a selectable marker (truncated nerve growth factor receptor (tNGFR) driven by the Ubiquitin C promoter (FIGS. 10A-10B) (FIG. 1B, top panel). The efficiency of genome targeting integration was determined in both frozen mobilized PB (mPB) and in freshly isolated CB-derived $CD34^+$ HSPCs from healthy male donors (FIG. 1B). We observed a median gene-targeting frequency of 23.2% (range 9.9-45.0%) for theINGFR donor and 45.0% (range 24.7-60.0%) for the –tNGFR IL2RG donor (FIG. 1B, bottom panel), as measured by Digital Droplet Droplet Digital PCR (ddPCR) (FIGS. 11A-11F). As the selection-free cassette gave high frequencies of targeted integration, we concluded that a selection marker was not necessary because it would create a simpler cell manufacturing process for cells that would also have a selective advantage.

Figure 12A:
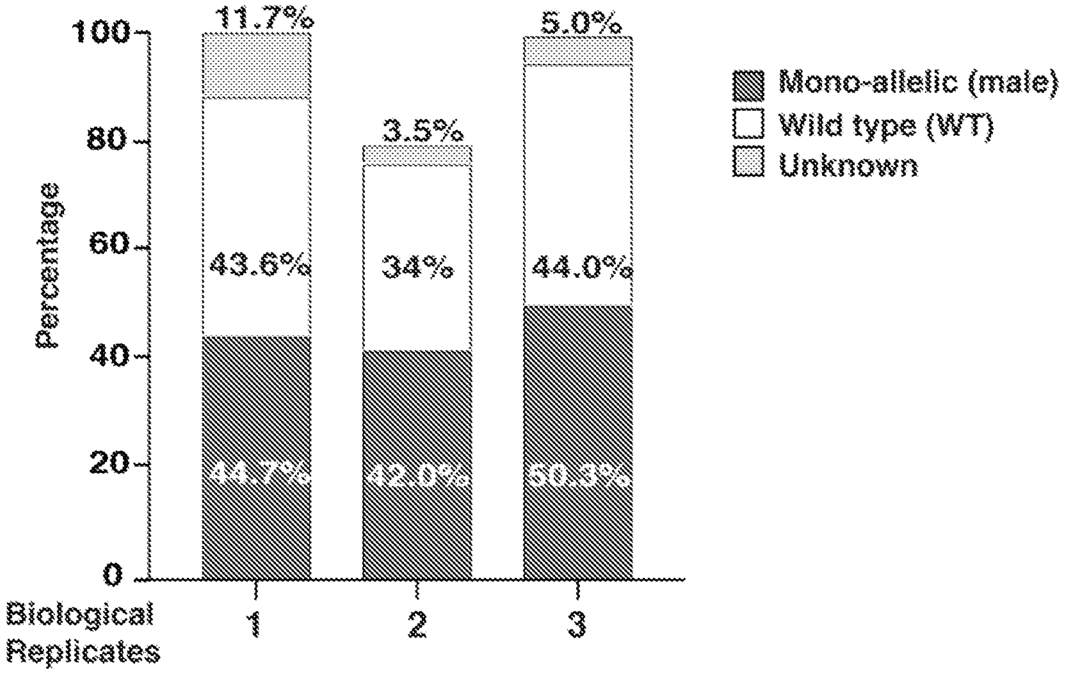
FIGS. 12A-12B. Methylcellulose derived colonies and genotyping analysis of IL2RG cDNA targeted CD34$^+$ HSPC single cells.
Figure 12B:
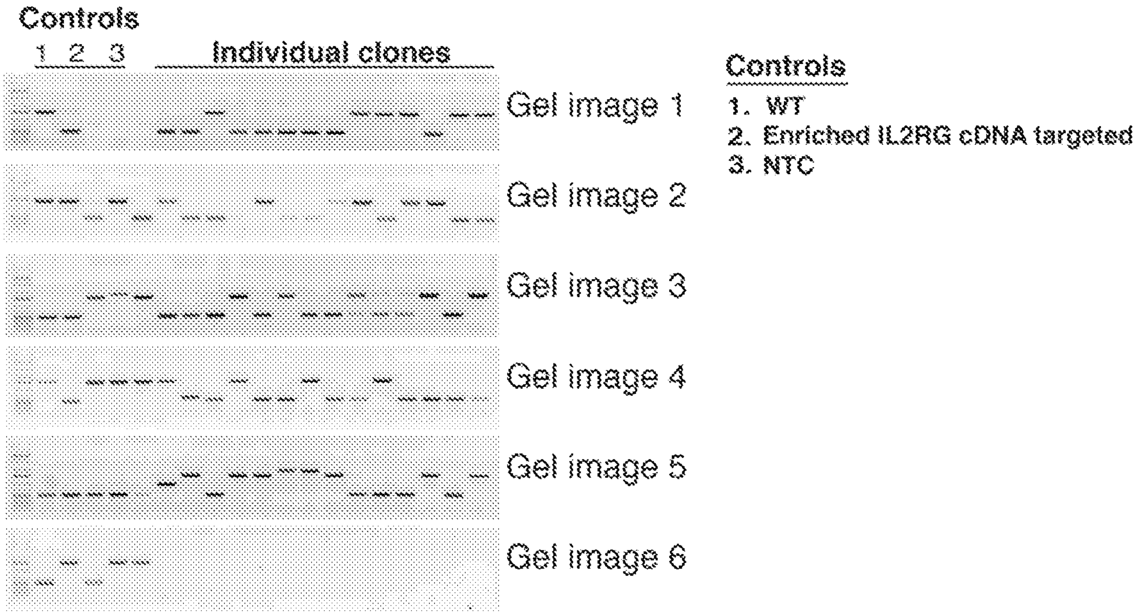

To determine the myeloerythroid differentiation potential of IL2RG cDNA genome targeted $CD34^+$ HSPCs, we performed methylcellulose assays. After Cas9/gRNA-rAAV6-CRISPR-Cas9-AAV6 based IL2RG cDNA targeting, HSPCs were single-cell plated in a 96-well methylcellulose plates and scored for colony formation at day 14. Although the number of colonies was reduced by ~35% in IL2RG cDNA targeted samples compared with mock-targeted HSPCs (where neither the sgRNA nor the donor were introduced) (FIG. 1C), the distribution of types of colony-forming units (CFUs) was the same from IL2RG cDNA targeted HSPCs and mock-targeted HSPCs, including CFU-GEMMs (granulocytes, erythrocytes, monocytes, megakaryocytes), without any lineage skewing (FIG. 1D). Genotyping of colonies confirmed that IL2RG cDNA targeted derived-colonies (n=344) showed an overall targeting frequency of 45.7%±2.4 (mean±s.e.m.) (FIG. 12). Bi-allelic modification is not relevant as the cells were derived from male donors and have a single X chromosome. In sum, the In vitro differentiation assay of targeted IL2RG cDNA $CD34^+$ HSPCs demonstrated no perturbation of the myeloerythroid differentiation potential.

Figure 13:
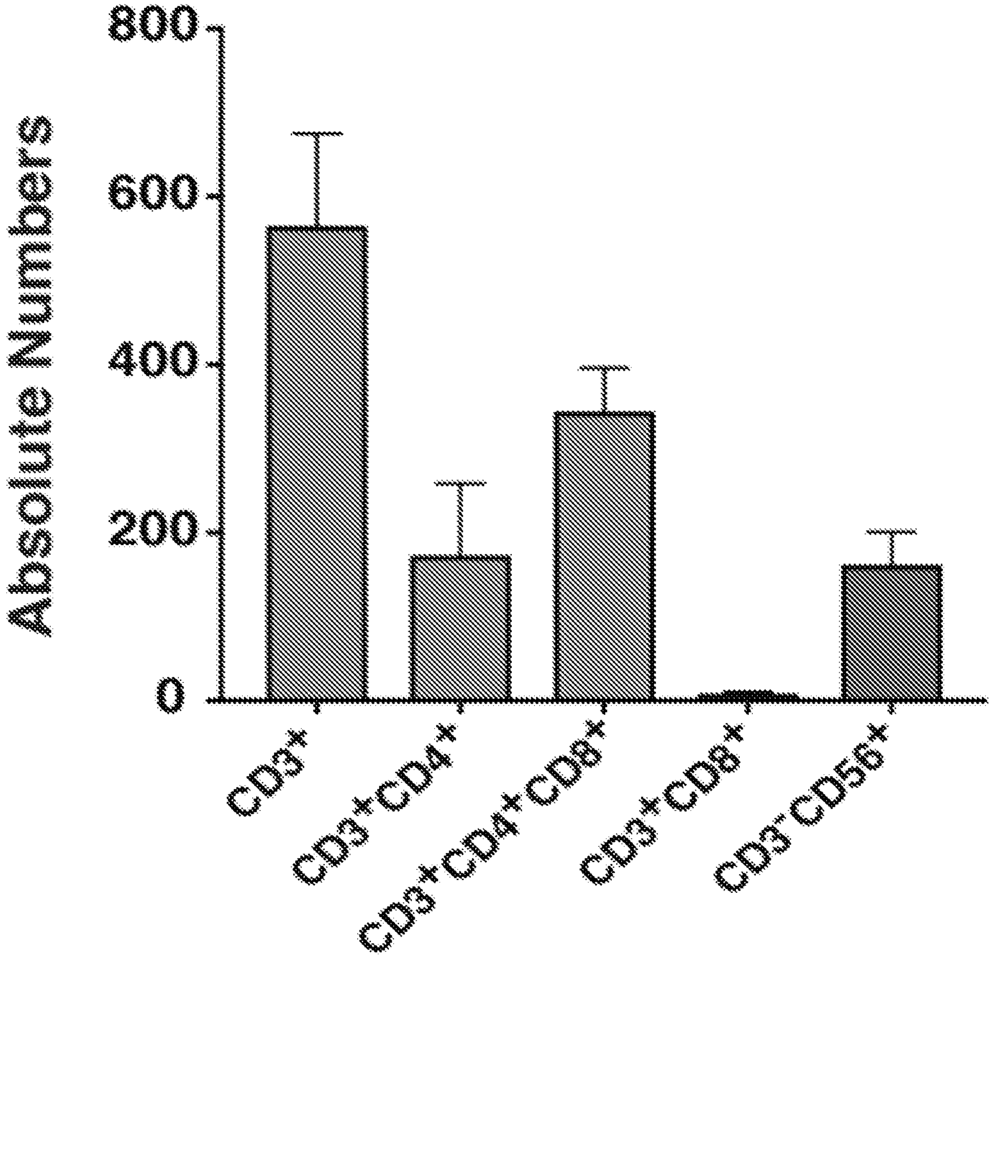
FIG. 13. In vitro IL2RG gene correction of SCID-X1 derived CD34$^+$ HSPCs. Shown are absolute numbers of pre-T cells, T-cells and NK cells derived at week one following induction of delta like 1 ligand (dll1) using doxycycline, from FIG. 1E. n=23 wells, mean±s.e.m.

To assess the hematopoietic differentiation potential of the codon-optimized IL2RG cDNA donor, we used the OP9-idll1 stromal cell line In vitro system. In this system, a lentiviral vector confers the doxycycline (DOX)-inducible expression of the Notch ligand Dll (35). In the presence of a cocktail of cytokines permissive for myeloerythroid and lymphoid differentiation, multi-potent human $CD34^+$ HSPCs will generate only myeloerythroid and B-cell lineage before induction of dill expression, but becomes permissive for T and NK-cell generation in the same well after addition of DOX to induce dill expression. $CD34^+$ HSPCs derived from frozen mPB of SCID-X1 patient (delA; M145fs—patient 2) were gene targeted (functionally corrected) using the CRISPR-Cas9-AAV6 platform. The total number of cells per well derived from the IL2RG cDNA targeted cells was markedly increased, compared with that of mutant cells, indicating a growth dependence on functional IL-7 and IL-15 receptors, for which IL2RG is an essential subunit (36). Following DOX-mediated dll1 expression, no further growth of mutant $CD34^+$ HSPCs was detected on OP9-idll1 stromal cells. In contrast, the IL2RG cDNA targeted cells continued to expand in myeloerythroid compartment in addition to the development of B ($CD19^+$), T ($CD3^+CD56^-$), NK ($CD3^-CD56^+$), and TNK ($CD3^+CD56^+$) progeny progenitors (FIG. 1E, FIG. 13). The OP9-idll1 In vitro system is known to generate more $CD3^+CD4^+$ over $CD3^+CD8^+$ cells expressing cell surface markers (37). A $CD3^+CD56^+$ (TNK cell) population was generated from our genome corrected SCID-X1 patient-derived $CD34^+$ HSPCs further demonstrating the range of lymphoid reconstition that can arise following ex vivo gene editing correction of the IL2RG gene from patient-derived cells (38). These experiments demonstrate the functional correction of the IL2RG gene from patient-derived $CD34^+$ HSPCs necessary for lymphoid development.

Hematopoietic Reconstitution from IL2RG cDNA Targeted HSPCs

Figure 14:
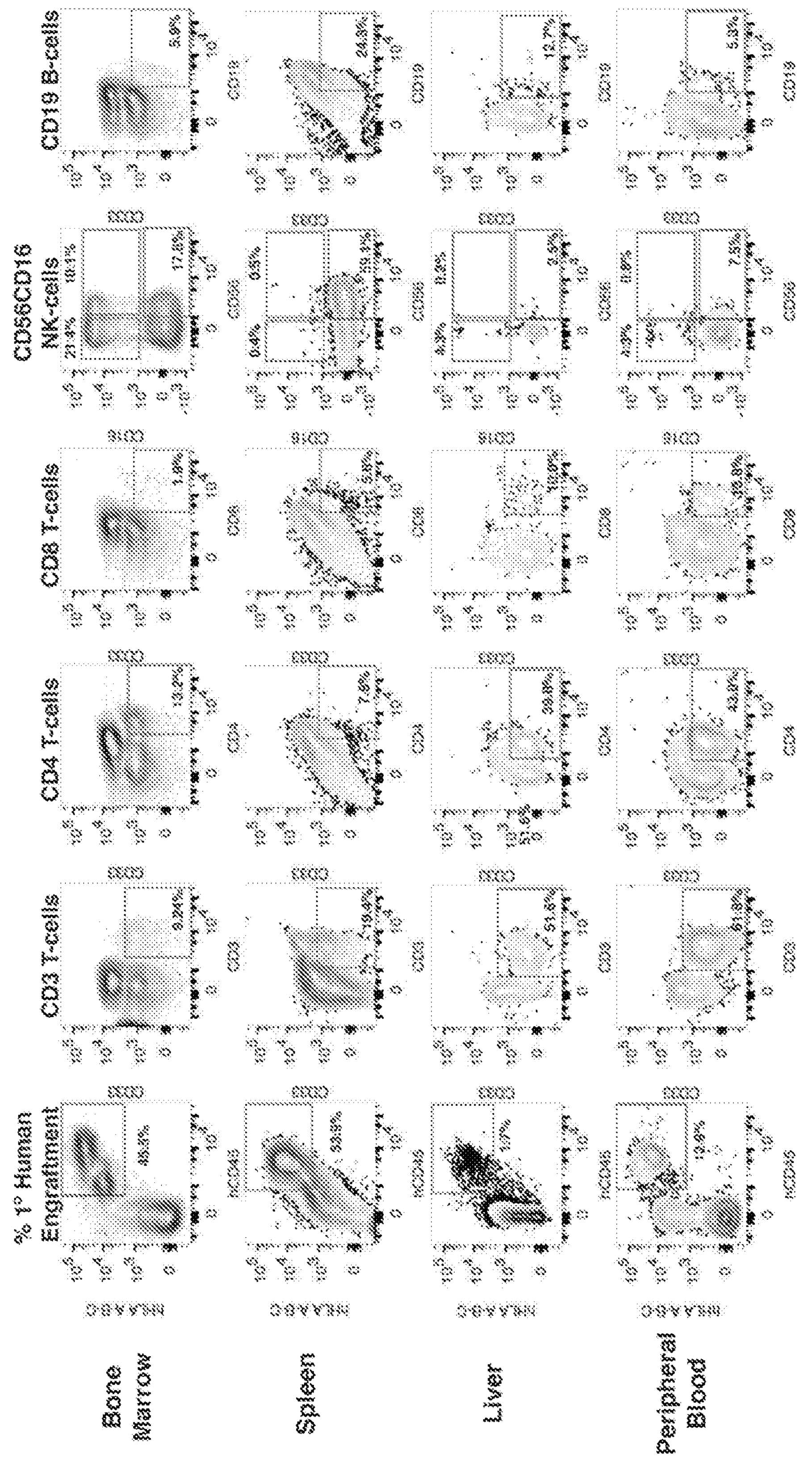
FIG. 14. Representative FACS plots for lymphoid lineage analysis at week 16 post intra-hepatic (IH) primary (1°) engraftment of IL2RG targeted CD34$^+$ HSPCs into new born NSG mice. Analysis is shown from a mouse with high (45.5%) human engraftment levels (hCD45$^+$ hHLA-ABC$^+$).
Figure 15:
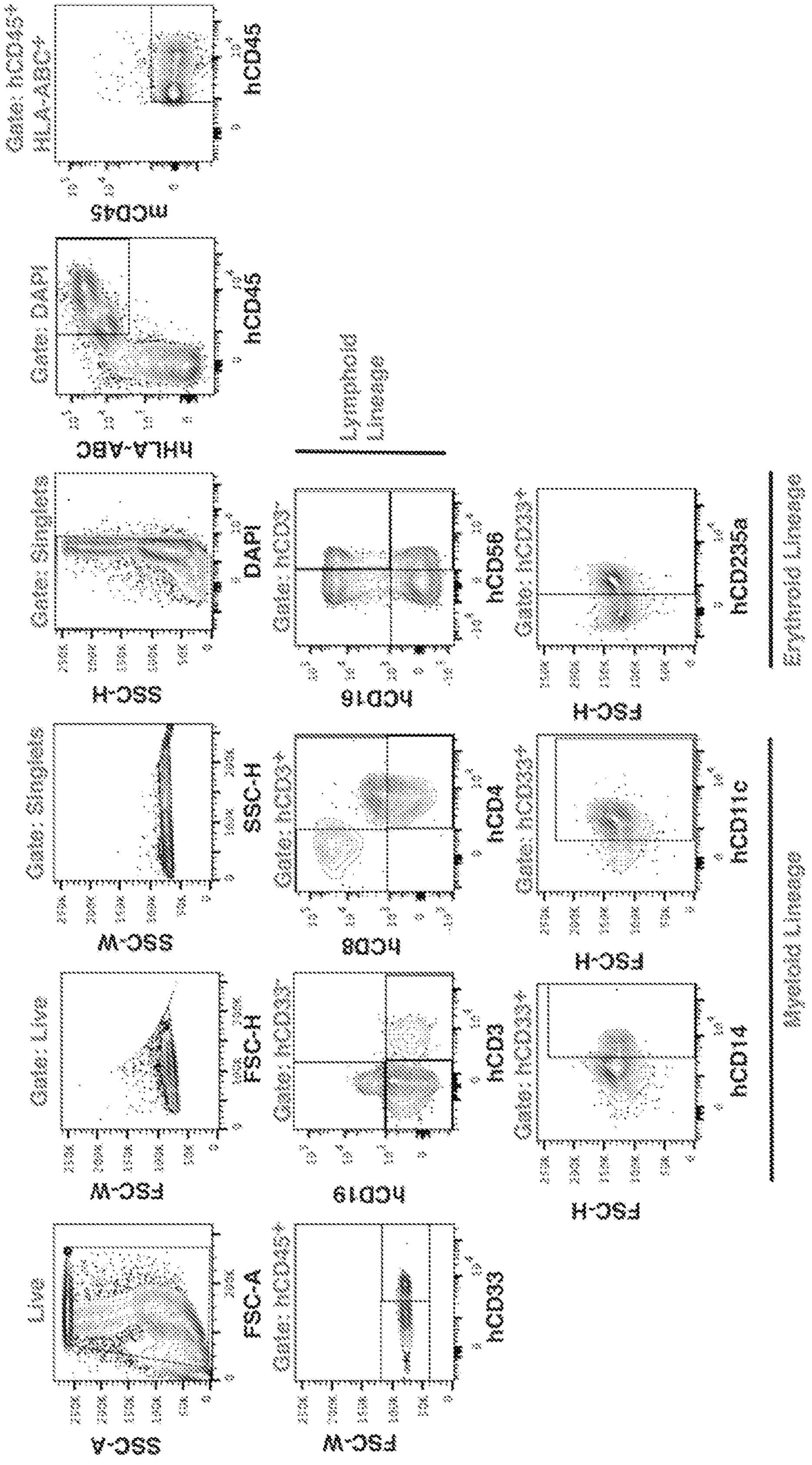
FIG. 15. Gating strategy for multilineage analysis. The following gating strategy was used to analyze multilineage development in vitro (FIG. 1E) and in vivo (FIGS. 2C-2E, FIGS. 3A-3C, FIGS. 4E-4F, FIGS. 17-20).

To further assess the toxicity and efficacy of our HR-GE system, we evaluated the In vivo engraftment and multilineage hematopoietic reconstitution of IL2RG cDNA targeted HSPCs in immunodeficient NSG mice. Following ~4 days of ex vivo manufacturing, IL2RG cDNA targeted and different control cells were transplanted either by intrahepatic (IH) injection into sub-lethally irradiated 3- to 4-day-old NSG pups or by intra-femoral (IF) injection into 6- to 8-week-old NSG mice. The IH system has previously been shown to be superior for assessment of human lymphopoiesis (39). An experimental schema is shown (FIG. 2A, primary engraftment panel). For primary engraftment studies, a total of 19.3 million cells, derived from three different healthy male CB $CD34^+$ HSPCs were transplanted into a total of 47 mice (FIG. 2B). The kinetics of primary human engraftment was monitored at weeks 8 and 12 in bone marrow (BM) aspirates and PB samples. At week 16, end point analysis was carried out on total BM, spleen (SP), and PB samples. High human engraftment levels—as shown by $hCD45^+$ $HLA\text{-}ABC^+$ double positive staining, blue/black circles—were obtained with no statistical difference between the IL2RG cDNA targeted and control cells—WT, mock, or RNP (FIG. 2B, FIGS. 14, 15). Transplanted IL2RG targeted HSPCs showed a median human engraftment level of 45% in BM (n=24), 28% in SP (n=24), and 6% in PB (n=24) (FIG. 2B). The targeted integration frequency of the IL2RG cDNA was 25.5% in BM (n=24), 44.8% in SP (n=24), and 56% in PB (n=6) at week 16 post engraftment (FIG. 2C). Multi-lineage reconstitution was achieved from both mock and IL2RG cDNA targeted cells in both the BM and SP samples of transplanted mice (FIG. 3A).

Figure 16A:
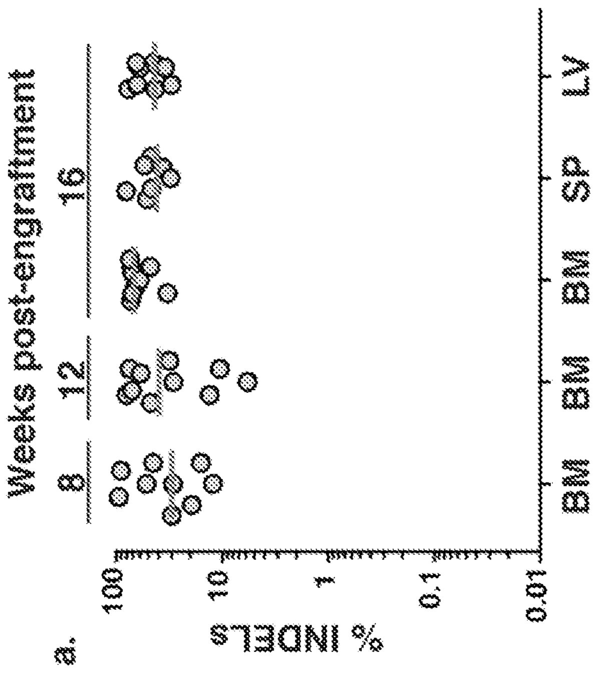
FIGS. 16A-16B. On-target INDEL spectrum analysis of truncated (19 nt) IL2RG sg-1 in CD34$^+$ HSPCs.
Figure 16B:
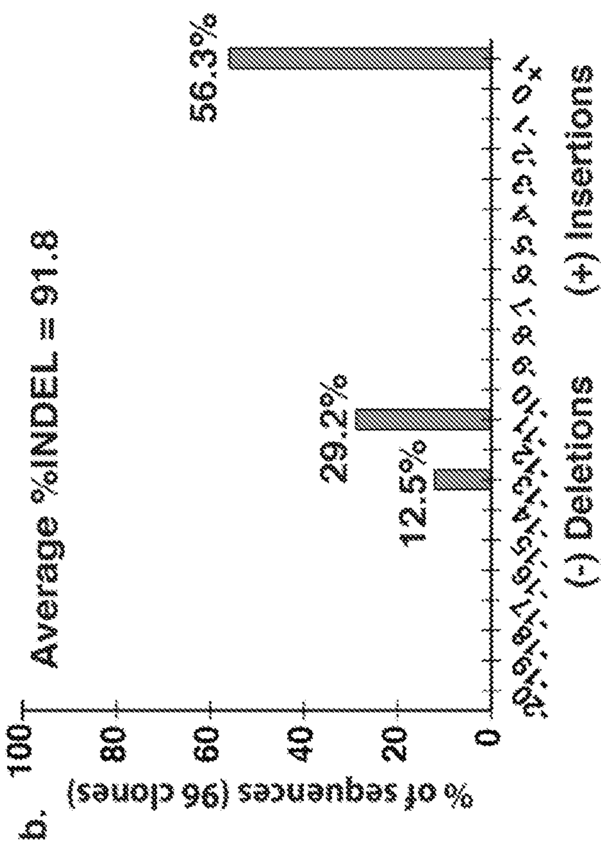

In human cells not targeted with the cDNA correction cassette, the frequency of INDELs was >90% in the IH engrafted IL2RG targeted cells at weeks 8, 12, and 16 with an INDEL spectrum of +1, −11, and −13 (all inactivating mutations) (FIG. 16). In sum, the engraftment of selection-free IL2RG cDNA targeted $CD34^+$ HSPCs derived from healthy male donors demonstrate the ability to give rise to normal hematopoiesis. As >90% of the non-gene targeted human cells have inactivating INDELs in the Il2RG gene, it is likely that the T and NK cells seen in the mice are derived from gene targeted $CD34^+$ HSPCs. The paucity of these cells in the mice, however, precluded definitive molecular analysis.

IL2RG cDNA Genome Targeting of LT-HSCs

Figure 17:
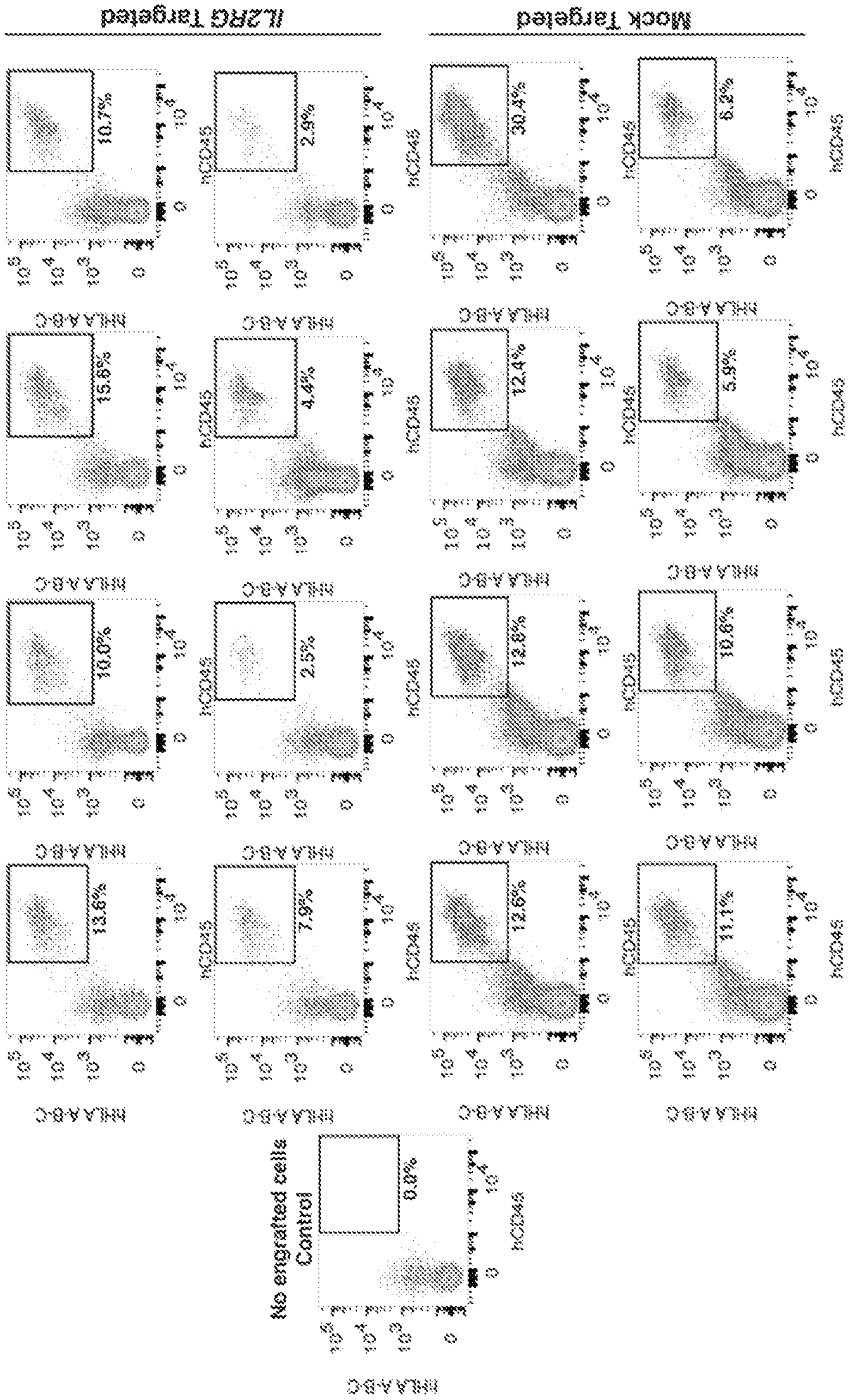
FIG. 17. FACS plots of secondary (2°) human engraftment levels ($hCD45^+$ $hHLA\text{-}ABC^+$). Secondary engraftment was carried out from total BM derived from primary (1°) IH IL2RG and mock targeted $CD34^+$ HSPCs. BM, bone marrow.
Figure 18:
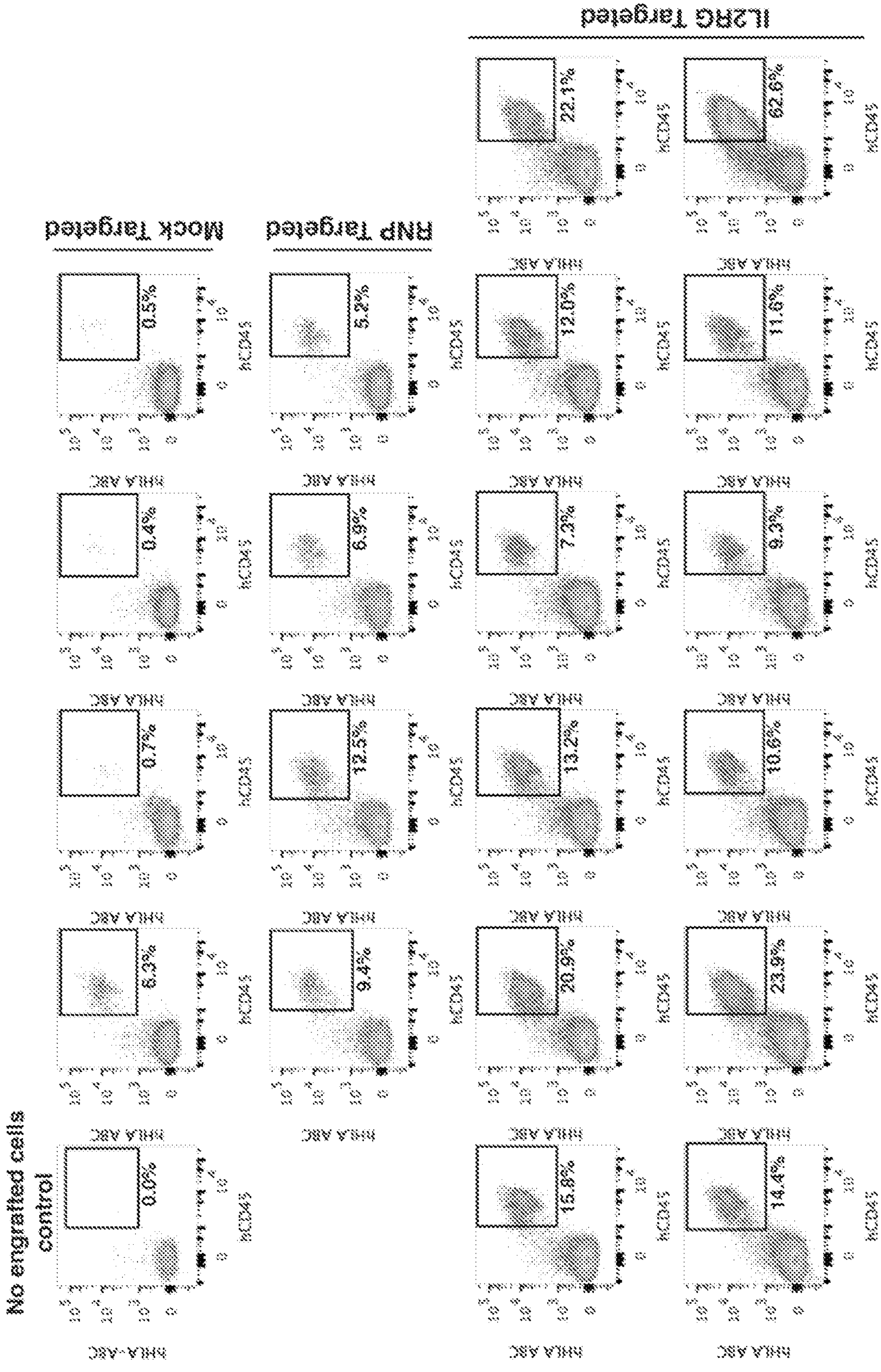
FIG. 18. FACS plots of 2° human engraftment levels ($hCD45^+$ $hHLA\text{-}ABC^+$) from total BM of mice injected IF with IL2RG or mock targeted $CD34^+$ HSPCs. $5\times10^5$ purified $CD34^+$ HSPCs from total BM of mock or IL2RG targeted engrafted mice were injected IF into sub-lethally irradiated adult NSG mice. The observed low levels of engraftment in 3 out of 4 mice that received mock treated cells were due to fluid backflow during the IF injection procedure. IF: intra-femoral.

The editing of LT-HSCs would provide the long-term maintenance of T-cell function in patients. We performed secondary transplantation studies to assess the robustness of our CRISPR-Cas9-AAV6 genome targeting platform in editing LT-HSCs. $CD34^+$ HSPCs were isolated from total BM of IL2RG cDNA targeted HSPCs (from both primary IH or IF engraftments at week 16). Following overnight culturing, secondary transplants were carried out in sub-lethally irradiated 6- to 8-week-old NSG mice (FIG. 2A). At 16 weeks following the secondary transplant, end point analysis—totaling 32 weeks of engraftment into immunodeficient mice—a median human chimerism level ($hCD45^+/HLA\text{-}ABC^+$ double positive cells) of IL2RG cDNA targeted cells ranged from 7.7% to 13.8% (BM) and 6.1% to 11.4% (SP) (FIG. 2D). The median targeted integration frequencies of the IL2RG cDNA donor was 9.5% or 20% (BM) and 16.4% or 21.7% (SP) (FIG. 2E). Fluorescence-activated cell sorting (FACS) plots showing BM human engraftment levels from mice injected with cells derived from both conditions are shown (FIGS. 17, 18). Analysis in secondary transplants showed multi-lineage hematopoietic reconstitution with no evidence of abnormal hematopoiesis thus providing further evidence of efficacy and safety (FIG. 3C).

A summary of the IL2RG cDNA targeted engrafted cells is shown in Tables 1 and 2. We report that 20 and 9.5% of human cells in the BM derived from IH-IF and IF-IF secondary xenotransplantation experiments, respectively, retain the codon-optimized IL2RG cDNA donor integration, demonstrating a clinically significant level of correction of $CD34^+$ LT-HSCs. Moreover, our median frequencies of IL2RG cDNA targeted in LT-HSCs significantly exceeds those reported by other groups, notably Genovese et al. (20) (ZFNs), Schiroli et al. (19) (ZFNs), and Dever et al. (25) (Cas9 RNP) where the percent of HR-GE cells was <5% of the human cells engrafted. These results, therefore, represent the first evidence of high frequencies of HR-GE in LT-HSCs using the CRISPR-Cas9 system. No tumors or abnormal hematopoiesis were observed in any mice that were transplanted with genome-modified cells (RNP or IL2RG cDNA targeted). Collectively, our primary and secondary transplantation results validate the robustness, effectiveness and lack of genotoxicity of our IL2RG cDNA genome targeting approach and strongly supports its advancement towards clinical translation.

TABLE 1

Summary of total number of cells and mice injected per condition for primary (1°) and secondary (2°) transplants.

| Genome editing condition transplanted into NSG mice | 1° Human transplant studies total nr. of cells injected per condition | 1° Human transplant studies total nr. of mice per condition (end point) | 2° Human transplant studies total nr. of cells injected per condition | 2° Human transplant studies total nr. of mice per condition (end point) |
|---|---|---|---|---|
| WT | $2.0 \times 10^6$ | 4 | n/a | n/a |
| Mock targeted | $5.7 \times 10^6$ | 15 | $4.3 \times 10^6$ | 12 |
| RNP only targeted | $2.0 \times 10^6$ | 4 | $1.5 \times 10^6$ | 4 |
| IL2RG cDNA targeted | $9.7 \times 10^6$ | 24 | $8.0 \times 10^6$ | 20 |
| Total | $19.3 \times 10^6$ | 47 | $13.8 \times 10^6$ | 36 |

TABLE 2

IL2RG cDNA genome targeted frequencies pre- and post-transplant.

| Time of genome editing quantification (ddPCR) | % Functionally corrected cells (BM) IH engraftment | % Functionally corrected cells (BM) IF engraftment |
|---|---|---|
| Prior to 1° transplant | 55% of $CD34^+$ HSPCs | 44% $CD34^+$ HSPCs |
| Prior to 1° transplant (16 weeks) | 28% of $CD34^+$ HSPCs | 26% of $CD34^+$ HSPCs |
| 2° Transplant (32 weeks) | 20% of $CD34^+$ HSPCs | 9.5% of $CD34^+$ HSPCs |

In Vivo Rescue of Lymphopoiesis

Figures 19A, 19B, 19C, 19D, 19E, 19F:
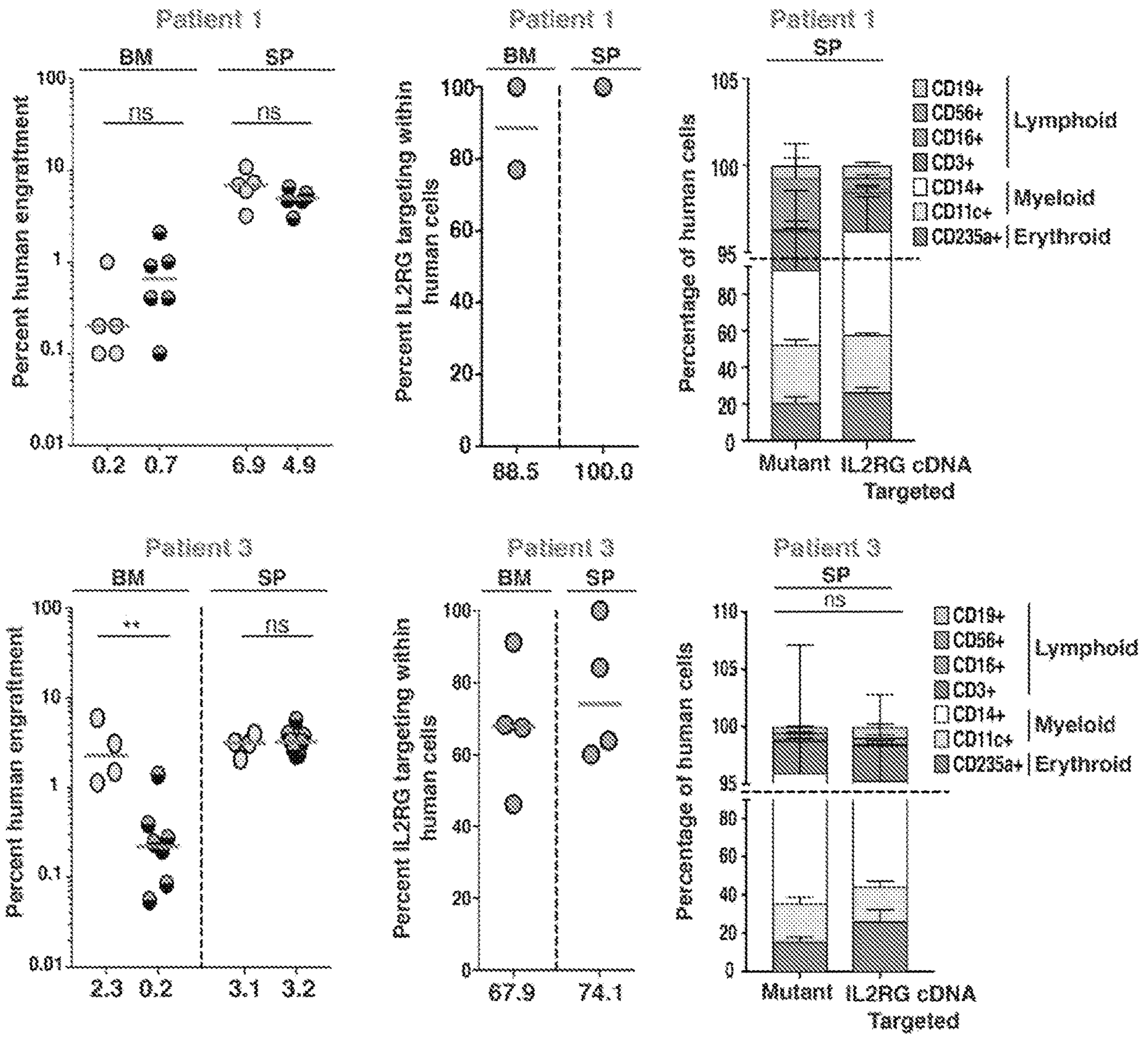
FIGS. 19A-19F. Primary human engraftment of SCID-X1 patient derived $CD34^+$ HSPCs.
Figure 20:
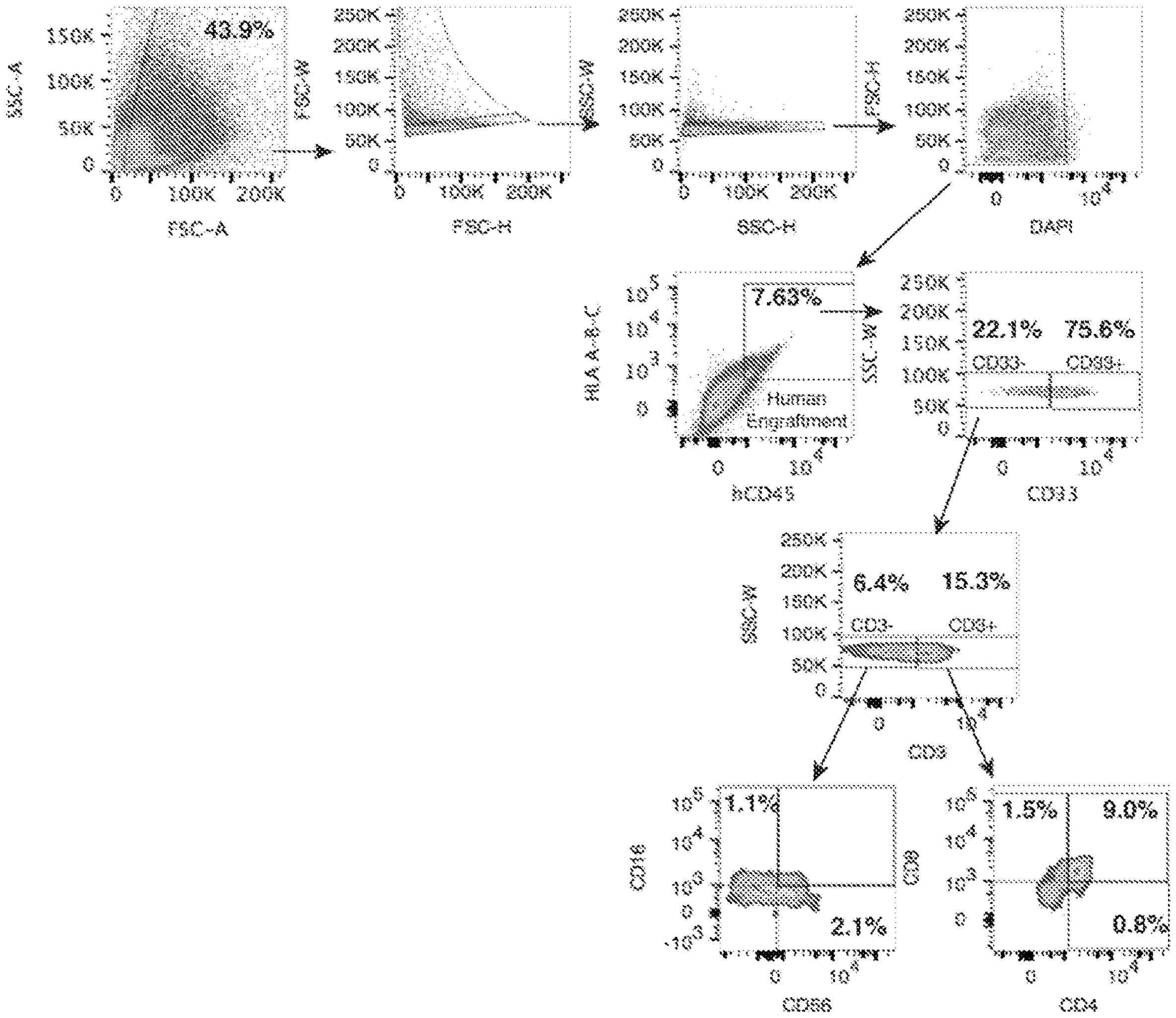
FIG. 20. Lymphoid lineage analysis of IL2RG cDNA targeted SCID-X1 patient 2 derived $CD34^+$ HSPCs. Representative FACS analysis of spleen sample derived from one NSG mouse at week 16 post engraftment with IL2RG cDNA targeted mobilized PB $CD34^+$ HSPCs. PB, peripheral blood.

We investigated whether our gene-targeting approach was reproducible and efficient in SCID-X1 patient-derived $CD34^+$ HSPCs. We edited $CD34^+$ HSPCs from six different SCID-X1 patients with a variety of different pathologic mutations (FIG. 4A). Five of the six samples were PB-derived $CD34^+$ HSPCs. We achieved high viability (>80%, n=5) with the CRISPR-Cas9-AAV6 system in the patient-derived cells and high gene-targeting (median 44.5 with range of 30.1— 47.0%, n=6), a frequency comparable to healthy donor $CD34^+$ HSPCs (45%, n=13) (FIGS. 4B-4C). A total of 7.3 million edited $CD34^+$ HSPCs derived from patients 1, 2, and 3 were engrafted into 29 NSG pups. Human chimerism was measured at week 16 following IH engraftment, with no statistically significant differences between unmodified and IL2RG cDNA targeted cells, both in the BM and SP samples obtained from mice transplanted with SCID-X1 patients 1 and 2 derived $CD34^+$ HSPCs (FIGS. 4E, 19). A statistically significant difference was observed only in BM samples derived from SCID-X1 patient 3 engraftment (p=0.0073, Holm-Sidak test) (FIG. 19). Importantly, only the codon-optimized IL2RG cDNA (not mutant allele) was detected in the SP of mice (n=8) engrafted with SCID-X1 patient 2 corrected $CD34^+$ HSPCs (Table 3), consistent with the survival advantage that a cell with a corrected IL2RG gene has. Multi-lineage analysis of SP samples derived from mice engrafted with IL2RG cDNA targeted SCID-X1 mPB $CD34^+$ HSPCs derived from patient 2 showed that significant levels of erythroid, myeloid, and lymphoid lineages were established (FIGS. 4E-4F). Gene corrected cells from both patients 1 and 3 showed high levels of engraftment following transplantation in both BM and SP (FIG. 19**). This work is the first to show in vivo rescue of the lymphoid lineage in a SCID-X1 patient-derived $CD34^+$ HSPCs. In sum, these transplantation studies demonstrated that IL2RG cDNA targeted $CD34^+$ HSPCs can engraft and rescue the SCID-X1 phenotype, as demonstrated by multi-lineage reconstitution both in vitro and in vivo. We observed no abnormal hematopoiesis in mice transplanted with HR-GE patient-derived cells providing further evidence for the safety of the process.

TABLE 3

Summary of SCID-X1 patients' derived $CD34^+$ HSPCs transplants.

| SCID-X1 patients 1-3 | Total nr. of cells injected per condition | Total nr. of mice per group |
|---|---|---|
| SCID-X1 mutant $CD34^+$ HSPCs | $3.25 \times 10^6$ | 13 |
| IL2RG cDNA targeted $CD34^+$ HSPCs | $7.25 \times 10^6$ | 29 |

Signaling and Proliferation of IL2RG cDNA Targeted T Cells

To assess the receptor function and signaling in progenitor cells in which the gene is expressed through the targeted integration of a codon-optimized cDNA into the translational start site of the endogenous locus, we evaluated the proliferation and signaling activity of HR-GE human T lymphocytes derived from adult healthy male donors. Mature T cells depend on proper IL2RG expression and signaling through IL2RG-containing receptors, e.g., IL-2R, to promote proliferation and differentiation (40). Activation of T cells by CD3/CD28 antibodies leads to a rapid induction of IL-2 cytokine, which in turn signals though the IL-2R. Subsequent phosphorylation of tyrosine residues on the cytoplasmic domains of the receptors initiates a cascade of events that phosphorylate and activate the signaling transducers and activators of transcription 5 (STAT5) proteins. Therefore, we assessed the levels of pSTAT5 in IL2RG cDNA targeted T cells, where the IL2RG cDNA donor contained tNGFR selectable marker (FIG. 5A). Intracellular staining for pSTAT5 from IL2RG cDNA targeted T cells (FIG. 5B) and levels of pSTAT5 (ratio of $tNGFR^+pSTAT5^+$ double-positive cells to that of $tNGFR^+$ only cells, marked red) was demonstrated to be comparable to that of unmodified normal T cells 69.3±7.0 vs 67.7±4.4 (mean±s.e.m.), respectively (FIG. 5C). As expected, knocking-out (KO) the IL2RG locus with an IL2RG targeted donor expressing only tNGFR, significantly reduced the levels of pSTAT5 (12.7±5.6; mean±s.e.m.) (FIG. 5B). We analyzed the MFI of the pSTAT5 level in WT, KI, and KO cells (FIG. 5C) and found that the KO cells had an extremely low pSTAT5 MFI (as expected), whereas the KI cells had pSTAT5 MFI (mean fluorescence intensity) that was ~50% of the wild-type cells. This lower signaling did not compromise lymphocyte development (FIGS. 1-4) nor proliferation (FIG. 5D). The KI cells did not have higher signaling, which has been hypothesized as a risk factor for transformation.

To demonstrate that the genome edited IL-2R is permissive for proliferation upon engagement of IL-2 cytokine, we quantified the levels of proliferation of IL2RG cDNA targeted T-cell following T-cell receptor (TCR) stimulation. A carboxyfluorescein succinimidyl ester (CFSE) dilution assay was used to measure whether targeted insertion of the codon-optimized cDNA could support T-cell proliferation. Loss of CFSE signal occurs when cells proliferate as the dye dilutes from cell division. An overview of the assay is shown (FIG. 5A). In our experimental settings, we observed similar proliferation profile in $tNGFR^+$ T cells (marking cells in which the IL2RG cDNA had been KI) compared with mock-targeted cells (FIG. 5E). We note that the "unmodified" cells had not undergone prior bead stimulation and so remained quiescent while the targeted and mock cells had undergone prior bead stimulation and thus there was residual proliferation without re-stimulation in those cells giving the broader peak. Overall, our data demonstrate that the genomic integration of an IL2RG codon diverged cDNA at the start site of the endogenous locus preserves normal signaling and proliferation of human T cells.

Off-Target and Karyotype Analysis

We investigated the specificity of the dsDNA break generated by the CRISPR-Cas9 RNP complex, which could be a potential source of genotoxicity. The off-target activity of the full-length 20 nt and three truncated versions (19 nt, 18 nt, and 17 nt) of sg-1 guide were assessed at 54 different potential sites predicted by either Guide-Seq in U20S cells 41 or bioinformatically COSMID42 (FIG. 6A). The analysis was performed in both healthy (FIG. 6B) and patient-derived $CD34^+$ HSPCs (FIG. 6B) to assess the specificity of the sg-1 gRNA. At the three sites identified by Guide-Seq analysis, there was no evidence of off-target INDELs. In the 51 sites identified by COSMID, only two showed evidence of off-target INDELs, both at levels <1% (FIG. 6A). We detected INDEL frequencies using the 20 nt sg-1 of 0.59%, in an intron of myelin protein zero-like 1(MPZL1), a cell surface receptor gene involved in signal transduction processes. The 19 nt sg-1 induced a lower frequency of off-target INDELs 0.11% (FIG. 6A and Table 4). We also analyzed the INDEL frequencies of potential off-target sites in genome edited $CD34^+$ HSPCs derived from SCID-X1 patient 1 in which the cells were edited using the 19 nt sg-1 (FIG. 6B). We found INDEL frequencies of 0.08% at MPZL1 and 0.27% at the ZNF330 site (intergenic and >9 kb from the nearby gene, respectively) (Table 4). Off-target activities of sg-1 guides, WT (20 nt) and truncated (19 nt), were further assessed in the context of a high-fidelity (HiFi) Cas943 in SCID-X1 $CD34^+$ HSPCs. The viability, INDELs, and IL2RG cDNA targeting frequency (% HR) were all equivalent (FIG. 6C) and editing frequencies (% INDELs) (FIG. 6D) were comparable between WT and HiFi Cas9 (FIGS. 6C-6F). Using the 20 nt and 19 nt gRNA combined with the HiFi Cas9, however, resulted in no detectable INDELs ("background" Table 4) at the two sites for which there was low but detectable INDEL frequency using WT Cas9.

RNP+AAV6). The analysis confirms absence of any chromosomal abnormalities in 20 out of 20 untreated or mock treated cells, 40 out of 40 RNP only or RNP treated with rAAV6 cells, and from 40 out of 40 cells treated with rAAV6 only (FIG. 21). Finally, we performed γH2AX and relative survival assays in K562 and 293T cells lines, respectively, to determine and compare the levels of DNA damage and toxicity induced by ZFN, TALEN, and CRISPR-Cas9 nucleases that all target the IL2RG gene (FIG. 22). The CCR5 ZFNs were first described in Perez et al. (45) and subsequently used to clinically and to modify $CD34^+$ HSPCs (24, 46, 47). The nucleases targeting the IL2RG gene were described previously in Urnov et al. (26) (ZFNs) and Hendel et al. (48) (ZFNs, TALENs, and CRISPR-Cas9). The CRISPR-Cas9 nuclease generated the lowest levels of toxicity by showing fewer γH2AX foci and higher percent survival of human cells overexpressing each nuclease (49) highlighting the notion that standard TALEN and ZFN nuclease platforms are less specific than CRISPR-Cas9.

In conclusion, our off-target analysis confirms that high specificity and activity is achieved using the IL2RG CRISPR-Cas9-AAV6 HR-GE system described here.

DISCUSSION

Currently there are numerous GE-based clinical trials in USA and China, none of which are for the treatment of PIDs (clinicaltrials.gov). There have been a number of proof-of-concept GE studies to explore the feasibility and safety of using a HR-mediated approach to correcting pathologic mutations in the IL2RG gene as a path to developing an auto-HSPC-based therapy for SCID-X1 (19, 20, 26, 50-54). In particular, a recent study by Schiroli et al. (19), in the process of developing a clinical translation GE for SCID-X1 in $CD34^+$ HSPCs, designed a ZFN GE-based platform to integrate a full IL2RG cDNA at intron 1 delivered by integration-defective lentiviral vector or rAAV6. They were able to generate ~40% INDELs and ~10% HR frequencies in WT $CD34^+$ HSPCs, with targeted integration frequencies of ~25% in one SCID-X1 patient-derived CB $CD34^+$ HSPCs. Notably, Schiroli et al. (19) performed only one experiment combining CRISPR-Cas9 with AAV6 and almost all of their data, including the engraftment data were from ZFN-modified cells. Our work represents significant progress for CRISPR-Cas9-based approaches as we not only demonstrate high levels of engraftment of targeted cells in LT-HSCs (up to 20%), we also demonstrate targeting efficiencies and engraftment of efficiencies in patient-derived $CD34^+$ HSPCs that exceed the LT-HSC threshold of 10%.

TABLE 4

Summary of IL2RGsgRNA off-target INDEL frequency analysis.

| Gene name | Guide Seq | COSMID | Chromosome location | Features | Expression in HSCs[a] | U2OS (plasmid) | WT $CD34^+$ 20 nt RNP (WT Cas9) | SCID-X1 $CD34^+$ 19 nt RNP (WT Cas9) | SCID-X1 $CD34^+$ 20 nt RNP (HiFi Cas9) | SCID-X1 CD34 19 nt RNP (HiFi Cas9) |
|---|---|---|---|---|---|---|---|---|---|---|
| L2RG | | | X | Exon | Yes | 81.1% | 81.7% | 91.7% | 94.1% | 97.6% |
| LIN01287 | ✓ | | 7 | Intergenic | Data not available | Background | Background | Background | Not sequenced | Not sequenced |
| MPZL1 | | ✓ | 1 | Intron | Yes | 1.1% | 0.1% | 0.1% | Background | Background |
| SHQ1 | ✓ | ✓ | 3 | Intron | Yes | 1.5% | Background | Background | Not sequenced | Not sequenced |
| SMYD3 | ✓ | | 1 | Intron | Yes | 4.2% | Background | Background | Not sequenced | Not Sequenced |
| ZNF330 | | ✓ | 4 | Intergenic | Data not available | Background | 0.23% | 0.27% | Background | Background |

To further assess whether genomic instabilities, particularly translocations, were generated by the—CRISPR-Cas9-AAV6 based process, we performed karyotype analysis on CB-derived $CD34^+$ HSPCs from healthy male donors. We chose to run karyotype analysis over PCR-based translocation assays because we have previously found that the frequency of translocations in $CD34^+$ HSPCs when two on-target breaks (with INDEL frequencies of >80%) was 0.2-0.5% 44. The probability that there is a translocation between the on-target break and break that has an INDEL frequency of <0.1% is exceedingly low. Whole chromosomal analysis was performed on ≥20 cells from the different conditions (WT, mock only, RNP only, AAV6 only and These high levels of genomic editing of LT-HSCs has not been previously reported and demonstrates with advances in technology, significant biologic improvements are possible with clinically relevant quantitative metrics being met. This level of correction is likely to be curative based on both animal studies (19), from patients who had spontaneous reversion mutations in progenitor cells and from human gene therapy clinical trials. In the gene therapy clinical trials for SCID-X1, immune reconstitution was achieved with as little as 1% of the cells having gene transfer 3 or from vector copy numbers of only 0.1 in the blood (2). Our results also show a lack of functional toxicity from the CRISPR-Cas9-AAV6 procedure because LT-HSCs were preserved and because normal human hematopoiesis was obtained from the genome-edited cells.

In contrast to Dever et al. (25), who also used a CRISPR-Cas9-AAV6 system, in this work we were not simply making a single-nucleotide correction but instead inserting a therapeutic transgene in $CD34^+$ HSPCs and up to 20% in LT-HSCs). This targeted cDNA integration therapeutic approach has the benefit of not only being able to correct >97% of known SCID-X1 pathogenic mutations due to the "universal" strategy design and thus should have broader application as most genetic diseases are caused by mutations throughout the gene.

The safety of the approach is further supported by the lack of karyotypic abnormalities generated in RNP exposed $CD34^+$ HSPCs and by INDEL frequencies below the limit of detection using a high-fidelity version of Cas9 at 54 potential off-target sites identified by bioinformatics and cell-based methods. Even using wild-type Cas9, off-target INDELs were only detected at two sites (both at low frequencies (<0.3%)), which were at sites of no known functional significance and did not result in any measurable perturbations in the cell population in all the assays used in this work the most important of which was no evidence of abnormal hematopoiesis in RNP-treated cells. In the course of these studies, we transplanted a full human dose for an infant (the target age that we are planning to treat in a phase I/II clinical trial) into NSG mice (28.4 million $CD34^+$ HSPCs), a functional safety standard that the Food and Drug Administration (FDA) has used prior to approving a phase I clinical trial of ZFN editing of $CD34^+$ HSPCs (24). The persistence of IL2RG gene corrected cells for 8 months (16 weeks in the primary followed by 16 weeks in the secondary recipient) following transplantation into NSG mice with multi-lineage hematopoiesis and without evidence of abnormal hematopoiesis also highlights the general lack of toxicity of the approach. An important aspect of our studies is that we achieved a median correction frequency of 44.5% without selection in PB patient-derived $CD34^+$ HSPCs, a cell source that is being used in lentiviral-based gene therapy trials. These functionally gene corrected $CD34^+$ HSPCs showed equivalent engraftment following transplantation into NSG mice as unmanipulated patient-derived $CD34^+$ HSPCs, again providing data that the GE manufacturing process was not damaging the cells in a significant way.

We also demonstrated that the "universal" strategy of knocking a codon-optimized wild-type cDNA into the endogenous start site functionally rescues gene function using both In vitro and In vivo assays of T and NK-cell development and function. These results include the rescue of T and NK-cell development and function from patient-derived $CD34^+$ HSPCs. While the ultimate test of the safety and efficacy of our approach will be established during a gene therapy clinical phase I/II trial, we believe that we have shown strong evidence using state-of-the-art, gold standard methods of the safety and efficacy of the CRISPR-Cas9-AAV6 approach to targeting a cDNA to the endogenous translational start site to functionally correct diseases causing mutations throughout a gene. It is likely, however, that specific details of the cDNA targeting strategy will have to be tailored to each gene in order to achieve the safe and effective levels of expression that are needed.

Our rationale for developing a GE-based gene therapy for SCID-X1 is to provide a safe, efficient, precise, and effective treatment option for patients. Although it is encouraging that improved methods for allo-HSCT are being developed and that the results using lentiviral-based gene therapy for SCID has been shown to be safe and effective, the long-term safety, efficacy, and limitations of these approaches remains to be determined. Thus, it is important to continue develop alternative strategies for curing patients with SCID-X1 using approaches that are less genotoxic (the mutational burden from GE is >1000-fold less than for lentiviral-based modification strategies by comparing the frequency of off-target INDELs to the frequency of uncontrolled lentiviral insertions). Ideally, multiple effective options will be available for patients, their families, and their treating physicians in the future thus giving them the opportunity to choose the approach that best fits their needs and circumstances. In sum, the safety and efficacy data presented in this study provides strong support for the clinical development of functional gene correction using the CRISPR-Cas9-AAV6 GE methodology to establish a long lasting therapeutic, potentially curative, strategy beneficial to >97% of SCID-X1 patients.

Methods

CRISPR-Cas9 sgRNA

Seven IL2RG, exon 1 specific, 20 nt length oligomer sequences, used in the initial screen, were identified using the online CRISPOR software (crispor.terof.net) and synthesized (Synthego, Redwood City, CA, USA) as part of a chimeric 100 nt sgRNA. Chemically modified sgRNA oligomers were manufactured using a proprietary synthesizer by Synthego Corp. (Redwood City, CA, USA) on controlled-pore glass (AM Chemicals, Carlsbad, CA, USA) using 2'-O-t-butyldimethylsilyl-protected and 2'-O-methyl ribonucleotide amidites (ChemGenes, Wilmington, MA) according to established procedures. Standard ancillary reagents for oxidation, capping and detritylation were used (EMD Millipore, Cincinatti, OH). Formation of internucleotide phosphorothioate linkages was performed using ((dimethylaminomethylidene) amino-3H-1,2,4-dithiazoline-3-thione (DDTT, ChemGenes, Wilmington, MA).

A set of 2'-O-methyl 3'phosphorothioate MS[30] modified full-length 20 nt and three additional versions having 1, 2, and 3 nt removed from the 5' end of the complementary region of the IL2RG sgRNA guide #1 were synthesized (TriLink Biotechnologies, San Diego, CA, USA) and purified using reverse phase high-performance liquid chromatography. Purity analysis was confirmed by liquid chromatography-mass spectrometry.

AAV6-Based DNA Donor Design and Vector Production

All homology based AAV6 vector plasmids were cloned into pAAV-MCS plasmid containing AAV2-specific inverted terminal repeats (ITRs) (Stratagene now part of Agilent Technologies, Santa Clara, CA, USA) using Gibson Assembly cloning kit according to the instructions in the commercial kit (New England Biolabs, cat #E5510S). Corrective, codon diverged IL2RG cDNA was designed to contain silent mutations that generated 78% sequence homology to the endogenous, wild-type gene. All AAV6 viruses were produced in 293T in the presence of 1 ng/ml sodium butyrate (Sigma-Aldrich, cat. no. 303410) cells and purified 48 h later using an iodixanol gradient approach as previously described 5. The following provides additional detail: all AAV6 viruses were produced in 293T seeded at 14×106 cells per dish in 10 15-cm dishes 1 day before transfection. In all, 6 μg ITR-containing plasmid and 22 μg pDGM6 (gift from Dr. David Russell, University of Washington, Seattle, WA, USA), containing the AAV6 cap genes, AAV2 rep genes, and adenovirus helper genes were transfected per one 15-cm dish using PEI at a 4:1 ratio (PEI to DNA). Forty-eight hours post transfection, AAV6 were harvested from cells by three freeze-thaw cycles, followed by a 45-min incubation with TurboNuclease at 250 U/mL (Abnova, Heidelberg, Germany). AAV vectors were purified using Iodixanol density gradient and ultracentrifugation at 48,000 rpms for 2 h at 18° C. AAV6 particles were extracted from the 40 to 60% gradient interface and dialyzed, three times, in PBS (phosphate-buffered saline) containing 5% sorbitol. A 10 K MWCO slide-a-lyzer G2 dialysis cassette (Thermo Fisher, Santa Clara, CA, USA) was used for dialyses. Pluronic acid was added to the purified AAV6 at a final concentration of 0.001%, aliquot and stored at −80° C.

CD34$^+$ HSPCs

Mobilized peripheral blood (mPB) and bone marow (BM) CD34$^+$ HSPCs cells were purchased from AllCells (Alameda, CA, USA). Cells were thawed using published protocol (55). Freshly purified CB-derived CD34$^+$ HSPCs, of male origin, were obtained through the Binns Program for Cord Blood Research at Stanford University, under informed consent. Mononuclear cells (MNCs) isolation was carried out by density gradient centrifugation using Ficoll Paque Plus (400×g for 30 min without brake). Following two platelet washes (200×g, 10-15 min with brake) HSPCs were labeled and positively selected using the CD34$^+$ Microbead Kit Ultrapure (Miltenyi Biotec, San Diego, CA, USA) according to manufacturer's protocol. Enriched cells were stained with Allophycocyanin (APC) anti-human CD34 (clone 561; Biolegend, San Jose, CA, USA) and sample purity was assessed on an Accuri C6 flow cytometer (BD Biosciences, San Jose, CA, USA). Following purification or thawing, CD34$^+$ HSCPs were cultured for 36-48 h at 37° C., 5% $CO_2$ and 5% O2, at a density of $2.5\times10^5$ cells/ml in StemSpan SFEM II (Stemcell Technologies, Vancouver, Canada) supplemented with Stem Cell Factor (SCF) (100 ng/ml), Thrombopoietin (TPO) (100 ng/ml), Fms-like tyrosine kinase 3 ligand (Flt3-Ligand) (100 ng/ml), Interleukin 6 (IL-6) (100 ng/ml), StemRegenin 1 (SR1) (0.75 mM), and UM171 (35 nM, Stemcell Technologies).

For secondary engraftment studies, CD34$^+$ HSPCs were purified from total BM of NSG mice at end point analysis. Sufficiently pure samples (≥80% CD34$^+$) were pooled and cultured at 37° C., 5% $CO_2$, and 5% $O_2$ for 12 h prior to secondary transplant.

T-Cell Purification

Primary human T cells were obtained from healthy male donors from Stanford University School of Medicine Blood Center after informed consent was obtained and purified by Ficoll density gradient centrifugation followed by red blood cell lysis in ammonium chloride solution (Stemcell Technologies,Vancouver, Canada) and magnetic negative selection using a Pan T-cell isolation kit (Miltenyi Biotec, San Diego, CA, USA) according to manufacturer's instructions. Cells were cultured at 37° C., 20% $O_2$ and 5% $CO_2$ in X-Vivo 15 (Lonza, Walkersville, MD, USA) supplemented with 5% human serum (Sigma-Aldrich, St. Louis, MO, USA) and 100 IU/ml human recombinant IL-2 (Peprotech, Rocky Hill, NJ, USA) and 10 ng/ml human recombinant IL-7 (BD Biosciences, San Jose, CA, USA). Cells were stimulated with immobilized anti-CD3 (OKT3, Tonbo Biosciences, San Diego, CA, USA) and with soluble anti-CD28 (CD28.2, Tonbo Biosciences) for three days prior to electroporation.

GE and INDEL Quantification

Editing of all primary cells was carried out using a ribonucleic protein (RNP) system at a molar ratio of either 1:2.5 or 1:5 (Cas9: sgRNA), unless otherwise stated. Recombinant *S. pyogenes* Cas9 protein was purchased from IDT (Integrated DNA Technologies, Coralville, Iowa, USA). Nucleofection was performed in P3 nucleofection solution (Lonza) and Lonza Nucleofector 4d (program DZ-100). Cells were plated at a concentration of $1.0\times10^5$-$2.5\times10^5$ cells/ml. For T cells editing, electroporation was performed using Lonza Nucleofector 4d (program EO-115) with an RNP composition as used for CD34$^+$ HSPCs editing. INDEL frequencies were quantified using TIDE online software on genomic DNA extracted using Quick Extract (Epicentre, an Illumina Company, cat no. QE09050) according to manufacturing specifications.

Genome Targeting and Quantification

CD34$^+$ HSPCs nucleofected with the IL2RG-specific RNP system were plated at a density of $5.0\times10^5$ cells/ml and transduced with the AAV6 donor at an multiplicity of infection (MOI) of 200,000 vg/μl within 15 min of nucleofection. Cells were cultured at 37° C., 5% $CO_2$, 5% $O_2$ for 36 h to 48 h after which they were either re-plated in fresh media, at a density of $2.5\times10^5$ cells/ml or prepared for xenotransplantation studies.

Absolute quantification of the levels of genomic integration was carried out using Digital Droplet PCR™ (ddPCR™, Bio-Rad, Hercules, CA, USA). Genomic DNA was extracted as described in previous section. In all, 1 μg of genomic DNA was digested with EcoRV-HF (20U) in Cutsmart buffer at 37° C. for 1 h. ddPCR reaction contains 1× reference primer/probe mix synthesized at a 3.6 ratio (900 nM primer and 250 nM FAM labeled probe), 1× target primer/probe mix synthesized at a 3.6 ratio (HEX labeled probe), 1×ddPCR Supermix for probe without dUTP, 50 ng of digested DNA and water for a total volume of 25 μl. The primers and probes sequences are detailed in Table 6.

Genomic DNA in the ddPCR mixture was partitioned into individual droplets using QX100 Droplet Generator, transferred to a 96-deep well PCR plate and amplified in a Bio-Rad PCR thermocycler. The following ddPCR program was optimized to amplify a 500-bp amplicon: step 1—95° C. for 10 min, ramp 1° C./s, step 2—94° C. for 30 s, ramp 1° C./s, step 3—60.8° C. for 30 s, ramp 1° C./s, step 4—72° C. for 2 min, ramp 1° C./s, step 5—repeat steps 2-4 for 50 cycles, step 6—98° C. for 10 min, ramp 1° C./s, step 7—4° C., ramp 1° C./s. Bio-Rad Droplet Reader and QuantaSoft Software were used to read and analyzed the experiment following manufacturer's guidelines (Bio-Rad). Absolute quantification as copy of DNA/μl was determined for the reference, endogenous IL2RG gene and for the integrated IL2RG cDNA. Percent targeting in total population was calculated as a ratio of HEX to FAM signal. For all targeting experiments, genomic DNA was derived from male donors.

Quantification of IL2RG cDNA targeted integration frequencies in SCID-X1 patients was assessed based on agarose gel quantification as IL2RG cDNA signal ratio intensity.

Methylcellulose CFU Assay

Two days post genome targeting, single cells were sorted onto 96-well plates coated with MethoCult Optimum (StemCell Technologies, cat no H4034). Fourteen days later, colonies derived from targeted and mock-treated cells were counted and scored based on morphological features pertaining to Colony Forming Units-erytroid (CFU-E), erythroid burst forming units (BFU-E), Colony Forminig Unit-Granulocytes, Monocytes (CFU-GM), and CFU-GEMM. Genotyping analysis was performed to quantify the percent of mono-allelic targeting. A three primer-based IL2RG-specific genotyping PCR-based protocol was established an optimized as follows: IL2RG WT-F1 5'-GGGTGACCAAGTCAAGGAAG-3' (SEQ ID NO: 13); int-IL2RG-R1: 5'-GATGGTGGTATTCAAGCCGACCCCGA-3' (SEQ ID NO: 14); IL2RG WT-R2: 5'-AATGTCCCACAGTATCCCTGG-3' (SEQ ID NO: 15). The PCR reaction contained 0.5 μM of each of the three primer, 1×Phusion Master Mix High Fidelity, 150-200 ng of genomic DNA and water to a final volume of 25 μl. The following PCR program generated an integration band of 543 bp from F1 and R1 primer set and an endogenous band of 1502 bp from F1 and R2 primer set: step 1—98° C. for 30 s, step 2—98° C. for 10 s; step 3—66° C. for 30 s; step 4—72° C. for 30 s, step 5—repeat steps 2-4 for a total of 30 cycles, step 6—72° C. for 7 min; step 7—4° C.

OP9-idll1 System

OP9 cells were generated as previously described (40). Briefly, OP9 stromal cells were infected with two lentiviral constructs, the first containing a TET-ON tetracycline transactivator (rtTA3) under control of a constitutive promoter (EF1a) and linked to turboRFP, and the second containing the Dll1 gene under control of a tet-responsive element (TRE) promoter and linked to turboRFP. In the presence of tetracycline or doxycyline, the rtTA3 rapidly activates expression of Dll1 and turboRFP.

Lymphoid Differentiation of Patient-Derived $CD34^+$ HSPCs

SCID-X1 patient-derived $CD34^+$ HSPCs were targeted with the IL2RG cDNA corrective donor. Forty-eight hours post targeting, 300 cells derived from either un-target or IL2RG cDNA targeted were sorted onto a well of a 96-well plate seeded with 50,000 OP9-idll1 cells 48 h in advance. Cells were incubated at 37° C., 5% $CO_2$, 10% $O_2$ for 1 week in activation media containing: alpha-MEM base media (ThermoFisher, cat no. 32561102), supplied with 10% fetal bovine serum (FBS; GemCell, cat no. 100-500), monothioglycerol (MTG) (100 μM), ascorbic acid (50 μg/ml), 1× penicillin/streptomycin, SCF (10 ng/ml, PeproTech, cat no. AF-300-07), Flt-3L (5 ng/ml, PeproTech, cat no. AF-300-19), IL-7 (5 ng/ml PeproTech, cat no. 200-07), IL-3 (3.3 ng/ml, PeproTech cat no. AF-200-03), Granulocyte-macrophage colony-stimulating factor (10 ng/ml, PeproTech, cat no. AF-300-03), TPO (10 ng/ml, PeproTech cat no. AF-300-18), EPO (2 U/ml, PeproTech, cat no. 100-64), IL-15 (10 ng/ml, PeproTech cat no. AF-200-15), IL-6 (10 ng/ml, PeproTech, cat no. 200-06). After 7 days, half the medium was exchanged and DOX was added at a final concentration of 1 μg/ml.

In Vitro Multi-Lineage Differentiation Analysis

Lymphoid, myeloid, and erythroid differentiation potential was determined using FACS analysis at 1 week post DOX induction. In all, 100% growth was obtained from all wells seeded with 300 targeted or mock-treated cells. Media were removed from all positive wells and cells were washed in 1×PBS. Cells were re-suspended in 50 μl MACS buffer (1×PBS, 2% FBS, 2 mM EDTA), blocked for nonspecific binding (5% vol/vol human FcR blocking reagent, Miltenyi, cat no. 130-059-901), stained for live dead discrimination using Live/Dead blue dead cell staining kit for UV (ThermoFisher Scientific, cat no. L23105) and stained (30 min, 4° C. dark) using CD3 PerCP/Cy5.5 (HiT3A, BioLegend), CD4 BV650 (OKT4, BioLegend), CD8 APC (HiT8a, BioLegend), CD11c BV605 (3.9, BioLegend), CD14 BV510 (M5E2, BioLegend), CD19 FITC (HIB19, BioLegend), CD33 AF-300 (WM53, BD Pharmingen), CD45 BV786 (BD Pharmingen), CD56 PE (MEM-188 BioLegend), CD235a PE-Cy7 (HI264, BioLegend), and CD271 (tNGFR) CF-594 (C40-1457, BD Horizon).

Phosphorylated STAT5 In Vitro Assay

To assess STAT5 phosphorylation in response to cytokine stimulation, purified human T cells were cultured for 7 days post electroporation and starved, overnight, in medium lacking serum and cytokines. Samples were split and either stimulated with IL-2 (100 U/ml) and IL-7 (10 ng/ml) or left unstimulated. Cells were split again, fixed, permeabilized using 4% PFA and methanol and stained with CD3 PE (UCHT1, BioLegend), CD271 (tNGFR) APC (ME20.4, Biolegend). Intracellular antigens were stained with pSTAT5 AF-488 (pY694, BD Bioscience) or isotype control (BD Biosciences). FACS analysis was performed on Accuri C6 (BD Biosciences) or Cytoflex (Beckman Coulter) and data analysis was performed using FlowJo.

CFSE Cellular Proliferation of IL2RG Targeted Human T Cells

Purified human T cells were nucleofected alone (mock treated) or in the presence of the long corrective IL2RG cDNA-tNGFR DNA donor vector. NGFRbright T cells were sorted. NGFRbright or mock-treated cells were labeled with CFSE (BioLegend) according to the manufacturer's protocol and either re-stimulated with anti-CD3/anti-CD28/IL-2/IL-7 as described in previous section or left unstimulated (IL-7 only). Targeting levels were monitored and quantified based on the tNGFR expression and on absolute quantification of the integrated IL2RG cDNA by ddPCR.

Xenotransplantation of Genome Targeted $CD34^+$ HSPCs into Mice

For all human engraftment studies, we used freshly purified CB derived $CD34^+$ HSPCs derived from healthy male donors, under informed consent. Human engraftment studies designed to rescue the disease phenotype were carried out using frozen, mPB $CD34^+$ HSPCs derived from SCID-X1 patients 1-3. SCID-X1 patients were given subcutaneous injections of Granulocytes Colony-Stimulating Factor (G-CSF) (filgrastim, Neupogen®; Amgen, Thousand Oaks, CA) for 5 consecutive days at 10-16 mcg/kg/day and one dose of Pleraxifor for mobilization and apheresis (National Institutes of Allergy and Infectious Disease IRB-approved protocol 94-I-0073). PB $CD34^+$ HSPCs were selected from the leukepheresis product using Miltenyi CliniMACS.

Human engraftment experimental design and mouse handling followed an approved Stanford University Administrative Panel on Lab Animal Care (APLAC). Cells used for engraftment studies were exposed to a maximum of 4 days ex vivo culturing.

IH Primary (1°) Human Engraftment

In all, $1.0\times10^5$ to $2.5\times10^5$ cells derived from IL2RG cDNA targeted cells or mock-treated cells (electroporated in the absence of RNP and never exposed to AAV6) were re-suspended in 25-30 μl of freshly prepared $CD34^+$ complete media with the addition of UM171 and SR1.

Three to 4 days old NSG pups were irradiated with 100 cGy and immediately engrafted IH using an insulin syringe with a 27 gauge×½" needle. A total of $2.15\times10^6$ cells from each condition were injected into 11 pups/condition. In all, 18/22 engrafted pups were analyzed at week 16 post engraftment.

Level of human engraftment was assessed at weeks 8 and 12 using BM aspirates and PB samples. At week 16 or later, end point analysis was done from total BM, SP, liver, and PB. For total BM analysis, mouse bones were harvested from tibiae, femurs, sternum, and spinal cord from each mouse and grinded using a mortar and pestle. MNCs were purified using Ficoll gradient centrifugation (Ficoll-Paque Plus, GE Healthcare, Sunnyvale, CA, USA) for 25 min at 2000×g, at room temperature. SP and liver samples were grinded against a 40 μM mesh, transferred to a FACS tube and spun down at 300×g for 5 min, at 4° C. Red blood cells were lysed following a 10- to 12-min incubation on ice with 500 μl of 1×ACK lysis buffer (ThermoScientific, cat no. A1049201). Reaction was quenched and cells were washed with MACS buffer (2-5% FBS, 2 mM EDTA, and 1×PBS). PB samples were treated with 500 μl of 2% Dextren and incubated at 37 C for 30 min to 1 h. In all, 800 μl to 1 ml of the top layer was transferred to a FACS tube, spun down at 300×g, 5 min and red blood cells lysed as already described.

Cells purified from all four sources were re-suspended in 50 μl MACS buffer, blocked, stained with LIVE/Dead staining solution and stained for 30 min at 4° C., dark with the following antibody panel: CD3 PerCP/Cy5.5 (HiT3A, BioLegend), CD19 FITC (HIB19, BioLegend), mCD45.1 PE-Cy7 (A20, BioLegend), CD16 PE-Cy5 (3G8, BD Pharmingen), CD235a PE (HI264, BioLegend), HLA A-B-C APC-Cy7 (W6/32, BioLegend), CD33 AF-300 (WM53, BD Pharmingen), CD8 APC (HiT8a, BioLegend), CD45 BV786 (HI3a, BD Horizon), CD4 BV650 (OKT4, BioLegend), CD11c BV605 (BioLegend), CD14 BV510 (M5E2, BioLegend), and CD56 Pacific Blue (MEM-188, BioLegend).

IF Primary (1°) Human Engraftment

In all, $5.0\times10^5$ cells derived from WT cells, mock treated, RNP treated, and IL2RG cDNA targeted cells were injected IF into 6-8 weeks old NSG mice. Mice were irradiated with 200 cGy 2-4 h prior to engraftment. Cells were prepared in the same fashion as described in the IH section. A total of $2.0\times10^6$ WT cells were injected into a total of four mice, $3.5\times10^6$ mock-treated cells were injected into seven mice, $2.0\times10^6$ RNP-treated cells were injected into four mice and $7.5\times10^6$ IL2RG cDNA targeted cells were injected into 15 mice. In all, 29/30 injected mice were analyzed at week 16 post engraftment, as described in the IH engraftment assay section.

Secondary (2°) Human Engraftment

Secondary engraftments experiments were derived from both IH and from IF engrafted human cells. From the IH mock and IL2RG cDNA targeted engrafted mice, total BM was collected at week 16 post primary engraftment, MNC were purified using Ficoll gradient centrifugation and $CD34^+$ cells were enriched using $CD34^+$ microbeads (Miltenyi). Enriched cells were pooled from five engrafted mice with mock-treated cells and from seven engrafted mice with IL2RG cDNA targeted cells and cultured overnight in complete $CD34^+$ media containing UM171 and SR1. Following overnight incubation, cellular count and viability was determined for mock-treated cells to be $2.47\times10^6$ cells at 85.5% viability and for IL2RG cDNA targeted cells was $4.8\times10^6$ cells at 84% viability. In all, $3.5\times10^5$ mock-treated cells and $5.0\times10^5$ IL2RG cDNA targeted cells were engrafted IF into eight 6-8 weeks old, irradiated NSG mice (four males and four females).

Secondary engraftment experiments derived from IF primary engraftments were carried on as described above with the following modification: $5.0\times10^5$ $CD34^+$ enriched cells derived from WT, mock and RNP primary engraftment assay were IF injected into four 6-8 weeks old NSG mice, $5.0\times10^5$ $CD34^+$ enriched cells derived from IL2RG cDNA targeted cells were IF injected into 12 6-8 weeks old NSG mice. Equal numbers of male and female mice were used.

IH Primary (1°) Human Engraftment

Frozen mPB $CD34^+$ HSPCs derived from SCID-X1 patients were thawed and genome targeted as described in previous section. In all, $2.5\times10^5$ cells were IH injected into 3-4 days old, irradiated NSG pups.

Guide-Seq sgRNAs were generated by cloning annealed oligos containing the IL2RG target sequence into pX330 (Addgene #42230) (56). In all, 200,000 U2OS cells (ATCC #HTB-96) were nucleofected with 1 μg of pX330 Cas9 and gRNA plasmid and 100 pmol dsODN using SE cell line nucleofection solution and the CA-138 program on a Lonza 4D-nucleofector. The nucleofected cells were seeded in 500 μl of McCoy's 5a Medium Modified (ATCC) in a 24-well plate. Genomic DNA (gDNA) was extracted 3 days post nucleofection using a Quick-DNA Miniprep plus kit (Zymo Research). Successful integration of the dsODN was confirmed by RFLP assay with NdeI. In all, 400 ng of gDNA was sheared using a Covaris LE220 Ultrasonicator to an average length of 500 bp. Samples were prepared for Guide-seq (41) and sequenced on the Illumina Miseq. Briefly, solid-phase reversible immobilization magnetic beads were used to isolate genomic DNA, which was further sheared to an averaged of 500 bp (Covaris S200), end-repaired and ligated to adaptors containing 8-nt random molecular index. Target enrichment was achieved through two rounds of nested PCR using primers complementary to the oligo tag. We analyzed GUIDE-Seq data using the standard pipeline (41) with a reduced gap penalty for better detection of off-target sites containing DNA or RNA bulges.

Bioinformatic Off-Target Identification

Potential off-target sites for the IL2RG gRNA in the human genome (hg19) were identified using the web tool COSMID (42) with up to three mismatches allowed in the 19 PAM (protospacer adjacent motif) proximal bases. After off-target site ranking, 45 sites were selected for off-target screening.

Off-Target Validation

Frozen mPB $CD34^+$ cells (AllCells) were electroporated with 300 μg/ml of Cas9 and 160 μg/ml of sgRNA. sgDNA was extracted 48 h after RNP delivery. Off-target sites were amplified by locus-specific PCR. PCR primers contained adapter sequences to facilitate amplicon barcoding via a second round of PCR as previously described (57). All amplicons were pooled at an equimolar ratio and sequenced on the Illumina Miseq according to manufacturer's instructions using custom sequencing primers for Read 2 and Read Index. Sequencing data were analyzed using a custom INDEL quantification pipeline (58).

Karyotype Analysis

Fresh CB $CD34^+$ HSPCs were purified, genome edited or targeted as previously described. Four days post ex vivo culturing and manipulations, $5\times10^5$ cells from WT untreated, mock, RNP only, RNP and AAV6 or AAV6 only treated cells were processed by Stanford Cytology Labs at Stanford University. Karyotyping analysis was performed on 20 cells derived from each condition.

IL2RG-Specific Genotoxicity Assays in Human Cell Lines

Levels of γH2AX induced by different classes of engineered nucleases were quantified by measuring the phosphorylation of histone H2AX, a marker of DSB formation. K562 cells were nucleofected with the indicated doses of each nuclease expression plasmid, and the percentage of $\gamma H2AX^+$ cells was measured by FACS at 48 h post nucleofection.

293T cells were co-transfected with plasmids expressing GFP and nuclease. GFP-positive cells were analyzed at day 2 and again at day 6 by FACS. Percent survival relative to I-SceI control was calculated as follows:

$$\frac{\text{Nuclease day 6/Nuclease day 2}}{I-SceI\text{ day }6/I-SceI\text{ day }2}\times 100$$

A percent equal to 100 denotes no toxicity while a percentage <100 marks toxicity.

FACS Analysis

All FACS analysis pertaining to OP9-idll1 and human engraftment analysis were done on FACS Aria II SORT instrument part of FACS Facility Core from Stanford University, Institute for Stem Cell Biology and Regenerative Medicine.

Statistical Analysis

Statistical analysis was done with Prism 7 (GraphPad Software).

TABLE 5 sgRNA Guides sequence for IL2RG exon 1.

| sgRNA Guide ID | sgRNA Guide Sequence | PAM sequence |
|---|---|---|
| sgRNA 1 | 5'TGGTAATGATGGCTTCAACA 3' (SEQ ID NO: 3) | TGG |
| sgRNA 2 | 5'GGGCAGCTGCAGGAATAAGA 3' (SEQ ID NO: 5) | GGG |
| sgRNA 3 | 5'AGGGATGTGAATGGTAATGA 3' (SEQ ID NO: 6) | TGG |
| sgRNA 4 | 5'TTCAGCCCCACTCCCAGCAG 3' (SEQ ID NO: 7) | GGG |
| sgRNA 5 | 5'ATTCCTGCAGCTGCCCCTGC 3' (SEQ ID NO: 8) | TGG |
| sgRNA 6 | 5'CGACAATTCTGACGCCCAAT 3' (SEQ ID NO: 9) | GGG |
| sgRNA 7 | 5'AGCTGCCCCTGCTGGGAGTG 3' (SEQ ID NO: 10) | GGG |

REFERENCES

1. Pai, S. Y. et al. Transplantation outcomes for severe combined immunodeficiency, 2000-2009. N. Engl. J. Med. 371, 434-446 (2014).
2. De Ravin, S. S. et al. Lentiviral hematopoietic stem cell gene therapy for X-linked severe combined immunodeficiency. Sci. Transl. Med. 8, 335ra357 (2016).
3. Stephan, V. et al. Atypical X-linked severe combined immunodeficiency due to possible spontaneous reversion of the genetic defect in T cells. N. Engl. J. Med. 335, 1563-1567 (1996).
4. Hacein-Bey-Abina, S. et al. LMO2-associated clonal T cell proliferation in two patients after gene therapy for SCID-X1. Science 302, 415-419 (2003).
5. Woods, N. B., Bottero, V., Schmidt, M., von Kalle, C. & Verma, I. M. Gene therapy: therapeutic gene causing lymphoma. Nature 440, 1123 (2006).
6. Hacein-Bey-Abina, S. et al. Insertional oncogenesis in 4 patients after retrovirus-mediated gene therapy of SCID-X1. J. Clin. Invest. 118, 3132-3142 (2008).
7. Six, E., et al. in ASGCT 20$^{th}$ Meeting, Washington DC, Abstract #753 (2017).
8. Wu, C. & Dunbar, C. E. Stem cell gene therapy: the risks of insertional mutagenesis and approaches to minimize genotoxicity. Front. Med. 5, 356-371 (2011).
9. Aiuti, A. & Roncarolo, M. G. Ten years of gene therapy for primary immune deficiencies. Hematol. Am. Soc. Hematol. Educ. Prog. doi.org/10.118 2/asheducation-2009.1.682 (2009).
10. Fischer, A., Hacein-Bey-Abina, S. & Cavazzana-Calvo, M. 20 years of gene therapy for SCID. Nat. Immunol. 11, 457-460 (2010).
11. Smogorzewska, E. M., Weinberg, K. I. & Kohn, D. B. [Transplantation of genetically modified cells in the treatment of children with SCID: great hopes and recent disappointments]. Med. Wieku. Rozwoj. 7, 27-34 (2003).
12. Ott, M. G. et al. Correction of X-linked chronic granulomatous disease by gene therapy, augmented by inser-

TABLE 6

Primers and probes for ddPCR based assay.

| Primer Name | Primer Sequence | Amplicon size (bp) |
|---|---|---|
| ddPCR-cDNA-F | 5' GGGTGACCAAGTCAAGGAAG 3' (SEQ ID NO: 16) | 499 |
| ddPCR-cDNA-R | 5' GATGGTGGTATTCAAGCCGA 3' (SEQ ID NO: 17) | |
| ddPCR-cDNA-Probe | 5' CAAGCGCCATGTTGAAACCCAGCCTGCCC 3' (SEQ ID NO: 18) | |
| ddPCR-Reference-F | 5' GGGAAGGTAAAACTGGCAAC 3' (SEQ ID NO: 19) | 483 |
| ddPCR-Reference-R | 5' GGGCACATATACAGCTGTCT 3' (SEQ ID NO: 20) | |
| ddPCR-Reference-Probe | 5' CCTCGCCAGTCTCAACAGGGACCCAGC 3' (SEQ ID NO: 21) | |
| ddPCR-GFP-F | 5' AAGGGGGAGGATTGGGAAG 3' (SEQ ID NO: 22) | 502 |
| ddPCR-GFP-R | 5' TCAGAAGGAGGAGGCCAAG 3' (SEQ ID NO: 23) | |
| ddPCR-GFP-Probe | 5' GCATGCTGGGGATGCGGTGGGC 3' (SEQ ID NO: 24) | |

tional activation of MDS1-EVI1, PRDM16 or SETBP1. Nat. Med. 12, 401-409 (2006).
13. Kang, E. M. et al. Retrovirus gene therapy for X-linked chronic granulomatous disease can achieve stable long-term correction of oxidase activity in peripheral blood neutrophils. Blood 115, 783-791 (2010).
14. Bortug, K. et al. Stem-cell gene therapy for the Wiskott-Aldrich syndrome. N. Engl. J. Med. 363, 1918-1927 (2010).
15. Cavazzana, M., Six, E., Lagresle-Peyrou, C., Andre-Schmutz, I. & Hacein-Bey-Abina, S. Gene therapy for X-linked severe combined immunodeficiency: where do we stand? Hum. Gene Ther. 27, 108-116 (2016).
16. Hacein-Bey-Abina, S. et al. A modified gamma-retrovirus vector for X-linked severe combined immunodeficiency. N. Engl. J. Med. 371, 1407-1417 (2014).
17. Thornhill, S. I. et al. Self-inactivating gammaretroviral vectors for gene therapy of X-linked severe combined immunodeficiency. Mol. Ther. 16, 590-598 (2008).
18. Voit, R. A., Hendel, A., Pruett-Miller, S. M. & Porteus, M. H. Nuclease-mediated gene editing by homologous recombination of the human globin locus. Nucleic Acids Res. 42, 1365-1378 (2014).
19. Schiroli, G. et al. Preclinical modeling highlights the therapeutic potential of hematopoietic stem cell gene editing for correction of SCID-X1. Sci. Transl . Med. doi.org/10.1126/scitranslmed.aan0820 (2017).
20. Genovese, P. et al. Targeted genome editing in human repopulating haematopoietic stem cells. Nature 510, 235-240 (2014).
21. Porteus, M. H. & Baltimore, D. Chimeric nucleases stimulate gene targeting in human cells. Science 300, 763 (2003).
22. Porteus, M. H., Cathomen, T., Weitzman, M. D. & Baltimore, D. Efficient gene targeting mediated by adeno-associated virus and DNA double-strand breaks. Mol. Cell. Biol. 23, 3558-3565 (2003).
23. Shalem, O. et al. Genome-scale CRISPR-Cas9 knockout screening in human cells. Science 343, 84-87 (2014).
24. DiGiusto, D. L. et al. Preclinical development and qualification of ZFN-mediated CCR5 disruption in human hematopoietic stem/progenitor cells. Mol. Ther. Methods Clin. Dev. 3, 16067 (2016).
25. Dever, D. P. et al. CRISPR/Cas9 beta-globin gene targeting in human haematopoietic stem cells. Nature 539, 384-389 (2016).
26. Urnov, F. D. et al. Highly efficient endogenous human gene correction using designed zinc-finger nucleases. Nature 435, 646-651 (2005).
27. Connelly, J. P., Barker, J. C., Pruett-Miller, S. & Porteus, M. H. Gene correction by homologous recombination with zinc finger nucleases in primary cells from a mouse model of a generic recessive genetic disease. Mol. Ther. 18, 1103-1110 (2010).
28. Li, T. et al. TAL nucleases (TALNs): hybrid proteins composed of TAL effectors and FokI DNA-cleavage domain. Nucleic Acids Res. 39, 359-372 (2011).
29. Jinek, M. et al. A programmable dual-RNA-guided DNA endonuclease in adaptive bacterial immunity. Science 337, 816-821 (2012).
30. Hendel, A. et al. Chemically modified guide RNAs enhance CRISPR-Cas genome editing in human primary cells. Nat. Biotechnol. 33, 985-989 (2015).
31. De Ravin, S. S. et al. CRISPR-Cas9 gene repair of hematopoietic stem cells from patients with X-linked chronic granulomatous disease. Sci. Transl. Med. doi.org/10.1126/scitranslmed.aah3480 (2017).
32. Eyquem, J. et al. Targeting a CAR to the TRAC locus with CRISPR/Cas9 enhances tumour rejection. Nature 543, 113-117 (2017).
33. Fu, Y., Sander, J. D., Reyon, D., Cascio, V. M. & Joung, J. K. Improving CRISPR-Cas nuclease specificity using truncated guide RNAs. Nat. Biotechnol. 32, 279-284 (2014).
34. Sentmanat, M. F., Peters, S. T., Florian, C. P., Connelly, J. P. & Pruett-Miller, S. M. A survey of validation strategies for CRISPR-Cas9 editing. Sci. Rep. 8, 888 (2018).
35. Inlay, M. A. et al. Identification of multipotent progenitors that emerge prior to hematopoietic stem cells in embryonic development. Stem Cell. Rep. 2, 457-472 (2014).
36. Hong, C., Luckey, M. A. & Park, J. H. Intrathymic IL-7: the where, when, and why of IL-7 signaling during T cell development. Semin. Immunol. 24, 151-158 (2012).
37. Seet, C. S. et al. Generation of mature T cells from human hematopoietic stem and progenitor cells in artificial thymic organoids. Nat. Methods 14, 521-530 (2017).
38. Lu, P. H. & Negrin, R. S. A novel population of expanded human CD3+CD56+cells derived from T cells with potent In vivo antitumor activity in mice with severe combined immunodeficiency. J. Immunol. 153, 1687-1696 (1994).
39. Traggiai, E. et al. Development of a human adaptive immune system in cord blood cell-transplanted mice. Science 304, 104-107 (2004).
40. Orr, S. J. et al. Implications for gene therapy-limiting expression of IL-2R gamma c delineate differences in signaling thresholds required for lymphocyte development and maintenance. J. Immunol. 185, 1393-1403 (2010).
41. Tsai, S. Q. et al. GUIDE-seq enables genome-wide profiling of off-target cleavage by CRISPR-Cas nucleases. Nat. Biotechnol. 33, 187-197 (2015).
42. Cradick, T. J., Qiu, P., Lee, C. M., Fine, E. J. & Bao, G. COSMID: a web-based tool for identifying and validating CRISPR/Cas off-target sites. Mol. Ther. Nucleic Acids 3, e214 (2014).
43. Vakulskas, C. A. et al. A high-fidelity Cas9 mutant delivered as a ribonucleoprotein complex enables efficient gene editing in human hematopoietic stem and progenitor cells. Nat. Med. 24, 1216-1224 (2018).
44. Bak, R. O. et al. Multiplexed genetic engineering of human hematopoietic stem and progenitor cells using CRISPR/Cas9 and AAV6. Elife doi.org/10.7554/eLife.27873 (2017).
45. Perez, E. E. et al. Establishment of HIV-1 resistance in CD4+T cells by genome editing using zinc-finger nucleases. Nat. Biotechnol. 26, 808-816 (2008).
46. Tebas, P. et al. Gene editing of CCR5 in autologous CD4 T cells of persons infected with HIV. N. Engl. J. Med. 370, 901-910 (2014).
47. Holt, N. et al. Human hematopoietic stem/progenitor cells modified by zinc-finger nucleases targeted to CCR5 control HIV-1 In vivo. Nat. Biotechnol. 28, 839-847 (2010).
48. Hendel, A. et al. Quantifying genome-editing outcomes at endogenous loci with SMRT sequencing. Cell Rep. 7, 293-305 (2014).
49. Pruett-Miller, S. M., Reading, D. W., Porter, S. N. & Porteus, M. H. Attenuation of zinc finger nuclease toxicity by small-molecule regulation of protein levels. PLoS. Genet. 5, e1000376 (2009).
50. Menon, T. et al. Lymphoid regeneration from gene-corrected SCID-X1 subject-derived iPSCs. Cell. Stem. Cell. 16, 367-372 (2015).

51. Matsubara, Y. et al. Transcription activator-like effector nuclease-mediated transduction of exogenous gene into IL2RG locus. Sci. Rep. 4, 5043 (2014).
52. Hoban, M. D. et al. Correction of the sickle cell disease mutation in human hematopoietic stem/progenitor cells. Blood 125, 2597-2604 (2015).
53. Ishikawa, F. et al. Development of functional human blood and immune systems in NOD/SCID/IL2 receptor {gamma} chain(null) mice. Blood 106, 1565-1573 (2005).
54. McDermott, S. P., Eppert, K., Lechman, E. R., Doedens, M. & Dick, J. E. Comparison of human cord blood engraftment between immunocompromised mouse strains. Blood 116, 193-200 (2010).
55. Denning, S. M., Tuck, D. T., Singer, K. H. & Haynes, B. F. Human thymic epithelial cells function as accessory cells for autologous mature thymocyte activation. J. Immunol. 138, 680-686 (1987).
56. Cong, L. et al. Multiplex genome engineering using CRISPR/Cas systems. Science 339, 819-823 (2013).
57. Lee, C. M., Cradick, T. J. & Bao, G. The *Neisseria meningitidis* CRISPR-Cas9 system enables specific genome editing in mammalian cells. Mol. Ther. 24, 645-654 (2016).
58. Lin, Y. et al. CRISPR/Cas9 systems have off-target activity with insertions or deletions between target DNA and guide RNA sequences. Nucleic Acids Res. 42, 7473-7485 (2014).

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

```
Informal Sequence Listing
Left homology arm of IL2RG constructs:
                                                        SEQ ID NO: 1
GCATGGCATAGAACGGTGATGTCGGGGGTGGGGGTTCAGAACTTCCATTATAGA

AGGTAATGATTTAGAGGAGAAGGTGGTTGAGAATGGTGCTAGTGGTAGTGAACA

GATCCTTCCCAGGATCTAGGTGGGCTGAGGATTTTTGAGTCTGTGACACTATTGT

ATATCCAGCTTTAGTTTCTGTTTACCACCTTACAGCAGCACCTAATCTCCTAGAGG

ACTTAGCCCGTGTCACACAGCACATATTTGCCACACCCTCTGTAAAGCCCTGGTT

TATAAGGTTCTTTCCACCGGAAGCTATGACAGAGGAAACGTGTGGGTGGGGAGG

GGTAGTGGGTGAGGGACCCAGGTTCCTGACACAGACAGACTACACCCAGGGAAT

GAAGAGCAAGCGCCATGT

Right homology arm of IL2RG constructs:
                                                        SEQ ID NO: 2
TGAAGCCATCATTACCATTCACATCCCTCTTATTCCTGCAGCTGCCCCTGCTGGGA

GTGGGGCTGAACACGACAATTCTGACGCCCAATGGGAATGAAGACACCACAGCT

GGTGGGAAATCTGGGACTGGAGGGGGCTGGTGAGAAGGGTGGCTGTGGGAAGG

GGCCGTACAGAGATCTGGTGCCTGCCACTGGCCATTACAATCATGTGGGCAGAAT

TGAAAAGTGGAGTGGGAAGGGCAAGGGGGAGGGTTCCCTGCCTCACGCTACTTC

TTCTTTCTTTCTTGTTTGTTTGTTTCTTTCTTTCTTTTGAGGCAGGGTCTCACTATGT

TGCCTAGGCTGGTCTCAAACTCCTGGCCTCTAGTGATCCTCCTGCCTCAGCCTTTC

AAAGCACCAGGATTACAGACATGAGCCA

IL2RG sgRNA target sequence (NP108/MPD-1)-full length sg-1
                                                        SEQ ID NO: 3
TGGTAATGATGGCTTCAACA

IL2RG sgRNA target sequence (NP108/MPD-1)-truncated sg-1
                                                        SEQ ID NO: 4
GGTAATGATGGCTTCAACA

IL2RG sgRNA target sequence (MPD-2)
                                                        SEQ ID NO: 5
5' GGGCAGCTGCAGGAATAAGA 3'

IL2RG sgRNA target sequence (MPD-3)
                                                        SEQ ID NO: 6
5' AGGGATGTGAATGGTAATGA 3'

IL2RG sgRNA target sequence (MPD-4)
                                                        SEQ ID NO: 7
5' TTCAGCCCCACTCCCAGCAG 3'

IL2RG sgRNA target sequence (MPD-5)
```

-continued

SEQ ID NO: 8

5' ATTCCTGCAGCTGCCCCTGC 3'

IL2RG sgRNA target sequence (MPD-6)

SEQ ID NO: 9

5' CGACAATTCTGACGCCCAAT 3'

IL2RG sgRNA target sequence (MPD-7)

SEQ ID NO: 10

5' AGCTGCCCCTGCTGGGAGTG 3'

Codon optimized IL2RG cDNA sequence

SEQ ID NO: 11

ATGTGAAACCCAGCCTGCCCTTTACTAGTCTGCTGTTTCTCCAACTCCCTCTGCTC

GGGGTCGGCTTGAATACCACCATCCTCACCCCTAACGGAAACGAGGATACTACC

GCCGATTTCTTTCTGACCACCATGCCAACCGATAGCCTGTCTGTCTCAACCCTGCC

CCTGCCTGAAGTCCAGTGCTTTGTCTTCAATGTGGAGTATATGAACTGCACCTGG

AATAGCTCCTCTGAACCACAGCCCACCAACCTGACACTGCACTACTGGTATAAGA

ACAGCGACAATGATAAGGTGCAGAAATGCTCCCATTATCTGTTCTCTGAGGAAAT

CACCAGTGGGTGTCAGCTGCAGAAGAAAGAGATTCACCTGTACCAGACATTTGT

GGTCCAGCTGCAGGACCCTCGGGAACCACGGAGACAGGCCACTCAGATGCTGAA

GCTGCAGAACCTGGTCATCCCCTGGGCTCCTGAGAATCTGACCCTGCATAAACTG

AGTGAGTCACAGCTGGAACTGAACTGGAACAATAGGTTCCTGAATCACTGTCTG

GAGCATCTGGTGCAGTACCGCACAGACTGGGATCACTCATGGACTGAACAGAGC

GTCGACTATCGACATAAGTTTAGCCTGCCATCCGTGGATGGACAGAAAAGGTAC

ACCTTCCGGGTGCGGAGCCGGTTCAACCCACTGTGCGGATCCGCCCAGCACTGGT

CTGAGTGGAGTCACCCCATCCATTGGGGGTCAAACACTAGCAAGGAGAATCCTTT

CCTGTTTGCCCTGGAAGCTGTGGTCATTTCCGTGGGATCTATGGGCCTGATCATTT

CCCTGCTGTGCGTGTACTTCTGGCTGGAGCGGACTATGCCACGAATTCCCACCCT

GAAGAACCTGGAGGACCTGGTGACAGAATATCACGGCAACTTCTCCGCCTGGTC

AGGGGTCAGCAAAGGACTGGCAGAGTCCCTGCAGCCTGATTACTCTGAGCGGCT

GTGCCTGGTGTCCGAAATTCCCCCTAAAGGAGGGGCACTGGGAGAAGGACCTGG

AGCCTCTCCATGTAACCAGCACTCTCCTTATTGGGCTCCACCTTGTTATACTCTGA

AACCCGAAACCTGA

Exemplary construct for knocking in codon optimized IL2RG cDNA into Exon 1 of the IL2RG gene to restore gene expression.

(5'HA) Left homology arm: 400 bp (187 bp-586 bp in AAV6 vector)

ATG (start site) is part of the 5'HA

IL2RG cDNA: 1106 bp (587 bp-1692 bp in AAV6 vector)

GGCGCGCC: AscI RE site (1693 bp-1700 bp in AAV6 vector)

*BgH Poly A*: 227 bp (1701 bp-1927 bp in AAV6 vector)

CCTGCAGG: SbfI RE site (1928 bp-1935 bp in AAV6 vector)

(3' HA) Right homology arm: 414 bp (1936 bp-2349 bp in AAV6 vector)

SEQ ID NO: 12

GCATGGCATAGAACGGTGATGTCGGGGGTGGGGGTTCAGAACTTCCATTATAGA

AGGTAATGATTTAGAGGAGAAGGTGGTTGAGAATGGTGCTAGTGGTAGTGAACA

GATCCTTCCCAGGATCTAGGTGGGCTGAGGATTTTTGAGTCTGTGACACTATTGT

ATATCCAGCTTTAGTTTCTGTTTACCACCTTACAGCAGCACCTAATCTCCTAGAGG

ACTTAGCCCGTGTCACACAGCACATATTTGCCACACCCTCTGTAAAGCCCTGGTT

TATAAGGTTCTTTCCACCGGAAGCTATGACAGAGGAAACGTGTGGGTGGGGAGG

GGTAGTGGGTGAGGGACCCAGGTTCCTGACACAGACAGACTACACCCAGGGAAT

GAAGAGCAAGCGCCATGTTGAAACCCAGCCTGCCCTTTACTAGTCTGCTGTTT

-continued

CTCCAACTCCCTCTGCTCGGGGTCGGCTTGAATACCACCATCCTCACCCCTA

ACGGAAACGAGGATACTACCGCCGATTTCTTTCTGACCACCATGCCAACCGA

TAGCCTGTCTGTCTCAACCCTGCCCCTGCCTGAAGTCCAGTGCTTTGTCTTC

AATGTGGAGTATATGAACTGCACCTGGAATAGCTCCTCTGAACCACAGCCCA

CCAACCTGACACTGCACTACTGGTATAAGAACAGCGACAATGATAAGGTGC

AGAAATGCTCCCATTATCTGTTCTCTGAGGAAATCACCAGTGGGTGTCAGCT

GCAGAAGAAAGAGATTCACCTGTACCAGACATTTGTGGTCCAGCTGCAGGA

CCCTCGGGAACCACGGAGACAGGCCACTCAGATGCTGAAGCTGCAGAACCT

GGTCATCCCCTGGGCTCCTGAGAATCTGACCCTGCATAAACTGAGTGAGTCA

CAGCTGGAACTGAACTGGAACAATAGGTTCCTGAATCACTGTCTGGAGCATC

TGGTGCAGTACCGCACAGACTGGGATCACTCATGGACTGAACAGAGCGTCG

ACTATCGACATAAGTTTAGCCTGCCATCCGTGGATGGACAGAAAAGGTACAC

CTTCCGGGTGCGGAGCCGGTTCAACCCACTGTGCGGATCCGCCCAGCACTG

GTCTGAGTGGAGTCACCCCATCCATTGGGGGTCAAACACTAGCAAGGAGAA

TCCTTTCCTGTTTGCCCTGGAAGCTGTGGTCATTTCCGTGGGATCTATGGGC

CTGATCATTTCCCTGCTGTGCGTGTACTTCTGGCTGGAGCGGACTATGCCAC

GAATTCCCACCCTGAAGAACCTGGAGGACCTGGTGACAGAATATCACGGCA

ACTTCTCCGCCTGGTCAGGGGTCAGCAAAGGACTGGCAGAGTCCCTGCAGC

CTGATTACTCTGAGCGGCTGTGCCTGGTGTCCGAAATTCCCCCTAAAGGAG

GGGCACTGGGAGAAGGACCTGGAGCCTCTCCATGTAACCAGCACTCTCCTT

ATTGGGCTCCACCTTGTTATACTCTGAAACCCGAAACCTGAGGCGCGCC*AGCC*

*TCGACTGTGCCTTCTAGTTGCCAGCCATCTGTTGTTTGCCCCTCCCCCGTGCCTTCCTT*

*GACCCTGGAAGGTGCCACTCCCACTGTCCTTTCCTAATAAAATGAGGAAATTGCATCGC*

*ATTGTCTGAGTAGGTGTCATTCTATTCTGGGGGGTGGGGTGGGGCAGGACAGCAAGG*

*GGGAGGATTGGGAAGACAATAGCAGGCATGCTGGGGATGCGGTGGGCT*CCTGCAGG

TGAAGCCATCATTACCATTCACATCCCTCTTATTCCTGCAGCTGCCCCTGCTGGGA

GTGGGGCTGAACACGACAATTCTGACGCCCAATGGGAATGAAGACACCACAGCT

GGTGGGAAATCTGGGACTGGAGGGGGCTGGTGAGAAGGGTGGCTGTGGGAAGG

GGCCGTACAGAGATCTGGTGCCTGCCACTGGCCATTACAATCATGTGGGCAGAAT

TGAAAAGTGGAGTGGGAAGGGCAAGGGGGAGGGTTCCCTGCCTCACGCTACTTC

TTCTTTCTTTCTTGTTTGTTTGTTTCTTTCTTTCTTTTGAGGCAGGGTCTCACTATGT

TGCCTAGGCTGGTCTCAAACTCCTGGCCTCTAGTGATCCTCCTGCCTCAGCCTTTC

AAAGCACCAGGATTACAGACATGAGCCA

What is claimed is:

1. A method of genetically modifying a cell from a subject with X-linked Severe Combined Immunodeficiency (SCID-X1), the method comprising:

introducing into a cell isolated from the subject a single guide RNA (sgRNA) targeting the interleukin 2 receptor subunit gamma (IL2RG) gene, an RNA-guided nuclease, and a homologous donor template comprising an IL2RG cDNA comprising a nucleotide sequence having 95% or greater identity to SEQ ID NO: 11, flanked by a first and a second IL2RG homology region; wherein:

the sgRNA binds to the nuclease and directs it to a target sequence within exon 1 of the IL2RG gene, whereupon the nuclease cleaves the gene at the target sequence, and wherein:

the cDNA is integrated by homology directed recombination (HDR) at the site of the cleaved IL2RG locus, such that the cDNA replaces the translational start site of the endogenous IL2RG gene and is expressed under the control of the endogenous IL2RG promoter, thereby providing functional IL2RG protein product in the cell.

2. The method of claim 1, wherein the sgRNA comprises a nucleotide sequence complementary to a sequence having 95% or greater identity to a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO: 10.

3. The method of claim 2, wherein the sgRNA comprises a nucleotide sequence complementary to SEQ ID NO:4.

4. The method of claim 1, wherein the sgRNA comprises 2'-O-methyl-3'-phosphorothioate (MS) modifications at one or more nucleotides.

5. The method of claim 1, wherein the RNA-guided nuclease is Cas9.

6. The method of claim 1, wherein the sgRNA and the RNA-guided nuclease are introduced into the cell as a ribonucleoprotein (RNP).

7. The method of claim 1, wherein the first and/or second IL2RG homology region comprises a nucleotide sequence having 95% or greater identity to SEQ ID NO:1 or SEQ ID NO:2.

8. The method of claim 7, wherein the first and second IL2RG homology regions comprise the nucleotide sequences of SEQ ID NO: 1 and SEQ ID NO:2.

9. The method of claim 8, wherein the homologous donor template comprises a sequence having 95% or greater identity to SEQ ID NO:12.

10. The method of claim 1, wherein the homologous donor template is introduced into the cells using a recombinant adeno-associated virus (rAAV) serotype 6 vector.

11. The method of claim 1, wherein the homologous donor template further comprises a selectable marker.

12. The method of claim 11, wherein the selectable marker is nerve growth factor receptor (NGFR) or a truncated form thereof (tNGFR).

13. The method of claim 1, wherein the cell is a $CD34^+$ hematopoietic stem and progenitor cell (HSPC).

14. A method of treating a subject with SCID-X1, comprising (i) genetically modifying a cell from the subject using the method of claim 1, and (ii) reintroducing the cell into the subject.

* * * * *

SEQUENCE LISTING

<160> NUMBER OF SEQ ID NOS: 24

<210> SEQ ID NO 1
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 1

```
gcatggcata gaacggtgat gtcgggggtg ggggttcaga acttccatta tagaaggtaa     60

tgatttagag gagaaggtgg ttgagaatgg tgctagtggt agtgaacaga tccttcccag    120

gatctaggtg ggctgaggat ttttgagtct gtgacactat tgtatatcca gctttagttt    180

ctgtttacca ccttacagca gcacctaatc tcctagagga cttagcccgt gtcacacagc    240

acatatttgc cacaccctct gtaaagccct ggtttataag gttctttcca ccggaagcta    300

tgacagagga aacgtgtggg tggggagggg tagtgggtga gggacccagg ttcctgacac    360

agacagacta cacccaggga atgaagagca agcgccatgt                          400
```

<210> SEQ ID NO 2
<211> LENGTH: 414
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 2

```
tgaagccatc attaccattc acatccctct tattcctgca gctgcccctg ctgggagtgg     60

ggctgaacac gacaattctg acgcccaatg ggaatgaaga caccacagct ggtgggaaat    120

ctgggactgg agggggctgg tgagaagggt ggctgtggga aggggccgta cagagatctg    180

gtgcctgcca ctggccatta caatcatgtg ggcagaattg aaaagtggag tgggaagggc    240

aagggggagg gttccctgcc tcacgctact tcttctttct ttcttgtttg tttgtttctt    300

tctttctttt gaggcagggt ctcactatgt tgcctaggct ggtctcaaac tcctggcctc    360

tagtgatcct cctgcctcag cctttcaaag caccaggatt acagacatga gcca          414
```

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 3

```
tggtaatgat ggcttcaaca                                                 20
```

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 4

```
ggtaatgatg gcttcaaca                                                  19
```

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gggcagctgc aggaataaga 20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
agggatgtga atggtaatga 20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ttcagcccca ctcccagcag 20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
attcctgcag ctgcccctgc 20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgacaattct gacgcccaat 20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
agctgcccct gctgggagtg 20

<210> SEQ ID NO 11

<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
atgtgaaacc cagcctgccc tttactagtc tgctgtttct ccaactccct ctgctcgggg     60
tcggcttgaa taccaccatc ctcaccccta acggaaacga ggatactacc gccgatttct    120
ttctgaccac catgccaacc gatagcctgt ctgtctcaac cctgcccctg cctgaagtcc    180
agtgctttgt cttcaatgtg gagtatatga actgcacctg gaatagctcc tctgaaccac    240
agcccaccaa cctgacactg cactactggt ataagaacag cgacaatgat aaggtgcaga    300
aatgctccca ttatctgttc tctgaggaaa tcaccagtgg gtgtcagctg cagaagaaag    360
agattcacct gtaccagaca tttgtggtcc agctgcagga ccctcgggaa ccacggagac    420
aggccactca gatgctgaag ctgcagaacc tggtcatccc ctgggctcct gagaatctga    480
ccctgcataa actgagtgag tcacagctgg aactgaactg gaacaatagg ttcctgaatc    540
actgtctgga gcatctggtg cagtaccgca cagactggga tcactcatgg actgaacaga    600
gcgtcgacta tcgacataag tttagcctgc catccgtgga tggacagaaa aggtacacct    660
tccgggtgcg gagccggttc aacccactgt gcggatccgc ccagcactgg tctgagtgga    720
gtcaccccat ccattggggg tcaaacacta gcaaggagaa tcctttcctg tttgccctgg    780
aagctgtggt catttccgtg ggatctatgg gcctgatcat ttccctgctg tgcgtgtact    840
tctggctgga gcggactatg ccacgaattc ccaccctgaa gaacctggag gacctggtga    900
cagaatatca cggcaacttc tccgcctggt caggggtcag caaaggactg gcagagtccc    960
tgcagcctga ttactctgag cggctgtgcc tggtgtccga aattccccct aaaggagggg   1020
cactgggaga aggacctgga gcctctccat gtaaccagca ctctccttat tgggctccac   1080
cttgttatac tctgaaaccc gaaacctga                                     1109
```

<210> SEQ ID NO 12
<211> LENGTH: 2163
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
gcatggcata gaacggtgat gtcgggggtg ggggttcaga acttccatta tagaaggtaa     60
tgatttagag gagaaggtgg ttgagaatgg tgctagtggt agtgaacaga tccttcccag    120
gatctaggtg ggctgaggat ttttgagtct gtgacactat tgtatatcca gctttagttt    180
ctgtttacca ccttacagca gcacctaatc tcctagagga cttagcccgt gtcacacagc    240
acatatttgc cacaccctct gtaaagccct ggtttataag gttctttcca ccggaagcta    300
tgacagagga aacgtgtggg tggggagggg tagtgggtga gggacccagg ttcctgacac    360
agacagacta cacccaggga atgaagagca agcgccatgt tgaaacccag cctgcccttt    420
actagtctgc tgtttctcca actccctctg ctcggggtcg gcttgaatac caccatcctc    480
acccctaacg gaaacgagga tactaccgcc gatttctttc tgaccaccat gccaaccgat    540
agcctgtctg tctcaaccct gcccctgcct gaagtccagt gctttgtctt caatgtggag    600
```

```
tatatgaact gcacctggaa tagctcctct gaaccacagc ccaccaacct gacactgcac    660
tactggtata agaacagcga caatgataag gtgcagaaat gctcccatta tctgttctct    720
gaggaaatca ccagtgggtg tcagctgcag aagaaagaga ttcacctgta ccagacattt    780
gtggtccagc tgcaggaccc tcgggaacca cggagacagg ccactcagat gctgaagctg    840
cagaacctgg tcatcccctg ggctcctgag aatctgaccc tgcataaact gagtgagtca    900
cagctggaac tgaactggaa caataggttc ctgaatcact gtctggagca tctggtgcag    960
taccgcacag actgggatca ctcatggact gaacagagcg tcgactatcg acataagttt   1020
agcctgccat ccgtggatgg acagaaaagg tacaccttcc gggtgcggag ccggttcaac   1080
ccactgtgcg gatccgccca gcactggtct gagtggagtc accccatcca ttgggggtca   1140
aacactagca aggagaatcc tttcctgttt gccctggaag ctgtggtcat ttccgtggga   1200
tctatgggcc tgatcatttc cctgctgtgc gtgtacttct ggctggagcg gactatgcca   1260
cgaattccca ccctgaagaa cctggaggac ctggtgacag aatatcacgg caacttctcc   1320
gcctggtcag gggtcagcaa aggactggca gagtccctgc agcctgatta ctctgagcgg   1380
ctgtgcctgg tgtccgaaat tcccccctaaa ggaggggcac tgggagaagg acctggagcc   1440
tctccatgta accagcactc tccttattgg gctccacctt gttatactct gaaacccgaa   1500
acctgaggcg cgccagcctc gactgtgcct tctagttgcc agccatctgt tgtttgcccc   1560
tcccccgtgc cttccttgac cctggaaggt gccactccca ctgtcctttc ctaataaaat   1620
gaggaaattg catcgcattg tctgagtagg tgtcattcta ttctgggggg tggggtgggg   1680
caggacagca agggggagga ttgggaagac aatagcaggc atgctgggga tgcggtgggc   1740
tcctgcaggt gaagccatca ttaccattca catccctctt attcctgcag ctgcccctgc   1800
tgggagtggg gctgaacacg acaattctga cgcccaatgg gaatgaagac accacagctg   1860
gtgggaaatc tgggactgga gggggctggt gagaagggtg gctgtgggaa ggggccgtac   1920
agagatctgg tgcctgccac tggccattac aatcatgtgg gcagaattga aaagtggagt   1980
gggaagggca agggggaggg ttccctgcct cacgctactt cttctttctt tcttgtttgt   2040
ttgtttcttt ctttcttttg aggcagggtc tcactatgtt gcctaggctg gtctcaaact   2100
cctggcctct agtgatcctc ctgcctcagc ctttcaaagc accaggatta cagacatgag   2160
cca                                                                 2163
```

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13

```
gggtgaccaa gtcaaggaag                                                 20
```

<210> SEQ ID NO 14
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
gatggtggta ttcaagccga ccccga 26

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 15
aatgtcccac agtatccctg g 21

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 16
gggtgaccaa gtcaaggaag 20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 17
gatggtggta ttcaagccga 20

<210> SEQ ID NO 18
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic probe"

<400> SEQUENCE: 18
caagcgccat gttgaaaccc agcctgccc 29

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 19
gggaaggtaa aactggcaac 20

<210> SEQ ID NO 20
<211> LENGTH: 20
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 20

gggcacatat acagctgtct                                              20


<210> SEQ ID NO 21
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 21

cctcgccagt ctcaacaggg acccagc                                      27


<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22

aagggggagg attgggaag                                               19


<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23

tcagaaggag gaggccaag                                               19


<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 24

gcatgctggg gatgcggtgg gc                                           22
```